(12) United States Patent
Grotjahn et al.

(10) Patent No.: US 9,708,236 B2
(45) Date of Patent: Jul. 18, 2017

(54) TERMINAL ALKENE MONOISOMERIZATION CATALYSTS AND METHODS

(71) Applicant: San Diego State University Research Foundation, San Diego, CA (US)

(72) Inventors: Douglas Grotjahn, San Diego, CA (US); Casey Larsen, Bolingbrook, IL (US); Gulin Erdogan, La Mesa, CA (US); Erik Paulson, San Diego, CA (US)

(73) Assignee: San Diego State University Research Foundation, San Diego, CA (US)

( * ) Notice: Subject to any disclaimer, the term of this patent is extended or adjusted under 35 U.S.C. 154(b) by 211 days.

(21) Appl. No.: 14/593,924

(22) Filed: Jan. 9, 2015

(65) Prior Publication Data

US 2015/0231621 A1 Aug. 20, 2015

Related U.S. Application Data

(60) Provisional application No. 61/925,582, filed on Jan. 9, 2014.

(51) Int. Cl.

| | | |
|---|---|---|
| *C07F 15/00* | (2006.01) | |
| *C07C 29/56* | (2006.01) | |
| *C07F 7/18* | (2006.01) | |
| *C07F 9/6506* | (2006.01) | |
| *C07C 5/25* | (2006.01) | |
| *B01J 31/18* | (2006.01) | |
| *B01J 31/22* | (2006.01) | |

(52) U.S. Cl.
CPC .............. *C07C 29/56* (2013.01); *B01J 31/189* (2013.01); *B01J 31/2295* (2013.01); *C07C 5/2593* (2013.01); *C07F 7/1852* (2013.01); *C07F 7/1892* (2013.01); *C07F 9/65066* (2013.01); *C07F 15/0046* (2013.01); *B01J 2231/50* (2013.01); *B01J 2531/821* (2013.01)

(58) Field of Classification Search
CPC .................................................. C07F 15/0046
See application file for complete search history.

(56) References Cited

U.S. PATENT DOCUMENTS

| | | | |
|---|---|---|---|
| 6,348,132 | B1 | 2/2002 | Zhang et al. |
| 6,355,855 | B1 | 3/2002 | Nguyen et al. |
| 2004/0106836 | A1 | 6/2004 | Hasenberg et al. |
| 2006/0084831 | A1 | 4/2006 | Zhang |
| 2010/0228031 | A1 | 9/2010 | Grotjahn |
| 2014/0228579 | A1 | 8/2014 | Nikonov et al. |

OTHER PUBLICATIONS

Grotjahn et al. "Extensive Isomerization of Alkenes Using a Bifunctional Catalyst: An Alkene Zipper" Journal of the American Chemical Society, 2007, vol. 129, pp. 9592-9593.*

Aleman et al. "New reactions of anticancer-platinum complexes and their intriguing behavior under various experimental conditions," Dalton Transactions, 2010. 39: pp. 10601-10607.

Bouziane et al., "Pentamethylcyclopentadienyl ruthenium: an efficient catalyst for the redox isomerization of functionalized allylic alcohols into carbonyl compounds," Elsevier, Oct. 8, 2008. pp. 11745-11750.

Chen et al. "Z-Selective Alkene Isomerization by High-Spin Cobalt(II) Complexes," Journal of the American Chemical Society, Jan. 3, 2014. 136: pp. 945-955.

Chianese et al., "Iridium Complexes of Bulky CCC-Pincer N-Heterocyclic Carbene Ligands: Steric Control of Coordination Number and Catalytic Alkene Isomerization," American Chemical Society, 2012.

Erdogan et al. "Mild and Selective Deuteration and Isomerization of Alkenes by a Bifunctional Catalyst and Deuterium Oxide," American Chemical Society, 2009.

Grotjahn et al., "Bifunctional Catalyst Control of Alkene Isomerization," Springer Science+Business, Sep. 13, 2014. pp. 1483-1489.

Jennerjahn et al, "Benign Catalysis with Iron: Unique Selectivity in Catalytic Isomerization Reactions of Olefins" ChemSusChem, 2012. 5: pp. 734-739.

Kobayashi et al. "Cobalt-Catalyzed Isomerization of 1-Alkenes to (e)-2-Alkenese with Dimethylphenylsilylmethylmagnesium Chloride and Its Application to the Steroselective Synthesis of (E)-Alkenylsilanes," Chem Asian J., 2009. 4: pp. 1078-1083.

Krompeic et al., "Highly Active Ruthenium Catalyst for Double Bond Migration," Pol. J. Chem. 1996. 70: pp. 813-818.

Larsen et al. "Correction to Stereoselective Alkene Isomerization Over One Position," Journal of American Chemical Society, Sep. 10, 2012. 134: pp. 15604.

Larsen et al. "General Catalyst Control of the Monoisomerization of 1-Alkenes to trans-2-Alkenes," Journal of the American Chemical Society, Jan. 14, 2014. 136: pp. 1226-1229.

Larsen et al. "Steroselective Alkene Isomerization over One Position," Journal of American Chemical Society, 2012.

Lee et al., "Six-, Five-, and Four-Coordinate Ruthenium(II) Hydride Complexes Supported by N-Heterocyclic Carbene Ligands: Synthesis, Characterization, Fundamental Reactivity, and Catalytic Hydrogenation of Olefins, Aldehydes, and Ketones," American Chemical Society, Feb. 20, 2009. 28: pp. 1758-1775.

Lim et al. "Facile Pd(II)- and Ni(II)-Catalyzed Isomerization of Terminal Alkenes into 2-Alkenes," Journal of Organic Chemistry, May 14, 2009. 74: pp. 4565-4572.

(Continued)

*Primary Examiner* — Joseph Kosack
(74) *Attorney, Agent, or Firm* — Haukaas Fortius PLLC; Michael H. Haukaas

(57) ABSTRACT

The invention provides novel catalysts and methods of using catalysts for controlling the position of a double bond and cis/trans-selectivity in isomerization of terminal alkenes to their 2-isomers. Catalysts such as (pentamethylcyclopentadienyl)Ru formulas 1 and 3 having a bifunctional phosphine can be used in the methods. A catalyst loading of 1 mol % of formulas 1+3 can be employed for the production of (E)-2-alkenes at 40-70° C.; lower temperatures can be used with higher catalyst loading. Acetonitrile-free catalysts can be used at lower loadings, room temperature, and in less than a day to accomplish the same results as catalysts 1+3. The novel catalyst systems minimize thermodynamic equilibration of alkene isomers, so that the trans-2-alkenes of both non-functionalized and functionalized alkenes can be generated.

22 Claims, 22 Drawing Sheets

(56) References Cited

OTHER PUBLICATIONS

MacHin et al., "Ruthenium-Catalyzed Nucleophilic Ring-Opening Reactions of a 3-Aza-2-oxabicyclo[2.2.1]hept-5-ene with Alcohols," American Chemical Society, Apr. 1, 2009. pp. 2077-2080.

Mayer et al., "Iron-Catalyzed Isomerizations of Olefins," ChemCatChem, 2001. 3: pp. 1567-1571.

McGowan et al., "Trianionic NCN3 Pincer Complexes of Chromium in Four Oxidation States (CrII, CrIII, CrIV, CrV): Determination of the Active Catalyst in Selective 1-Alkene to 2-Alkene Isomerization," American Chemical Society, Aug. 29, 2011. 30: pp. 4949-4957.

Morrill et al. "Efficient Hydride-Assisted Isomerization of Alkenes via Rhodium Catalysis," American Chemical Society, Aug. 3, 2003. 22: pp. 1626-1629.

Severa et al., "Air-tolerant C—C bond formation via organometallic ruthenium catalysis: diverse catalytic pathways involving (C5Me5)Ru or (C5H5)Ru are robust to molecular oxygen," Elsevier, May 27, 2009. 50: pp. 5426-4528.

Sivaramakrishna et al., "Selective isomerization of 1-alkenes by binary metal carbonyl compounds," Elsevier, Apr. 9, 2008. 27: pp. 1911-1916.

Varela et al. "Ru-Catalyzed Cyclization of Terminal Alkynals to Cycloalkenes," J Am Chem Soc, 2006.

Yamamoto et al., "Tandem Ruthenium-Catalyzed Transfer-Hydrogenative Cyclization/Intramolecular Diels-Alder Reaction of Enediynes Affording Dihydrocoumarin-Fused Polycycles," American Chemical Society, Mar. 5, 2014. 16: pp. 1806-1809.

\* cited by examiner $^1$H NMR spectrum of 1 + 3 at -20 °C (500 MHz, acetone-$d_6$).

$^{13}$C{$^1$H} NMR spectrum 1 + 3 at -20 °C (125.7 MHz, acetone-$d_6$).

$^{31}$P{$^{1}$H} NMR spectrum of 1 + 3 at -20 °C (202.4 MHz, acetone-$d_6$).

Major Species - Catalyst X

Ionized Species - Catalyst Y

1H NMR spectrum – Catalyst Y in acetone-$d_6$:

13C NMR spectrum – Catalyst Y in acetone-$d_6$:

X-Ray Crystal Structure – Catalyst Y:

TERMINAL ALKENE MONOISOMERIZATION CATALYSTS AND METHODS

RELATED APPLICATIONS

This application claims priority under 35 U.S.C. §119(e) to U.S. Provisional Patent Application No. 61/925,582, filed Jan. 9, 2014, which is incorporated herein by reference.

GOVERNMENT SUPPORT

This invention was made with government support under Grant No. CHE-1059107 awarded by the National Science Foundation. The government has certain rights in the invention.

BACKGROUND OF THE INVENTION

Alkenes are fundamental chemical feedstocks used on massive industrial scales. Plotkin, J. S. *Catal. Today* (2005), 106, 10-14. The alkene functional group is important to fine chemical synthesis (e.g., synthesizing pharmaceuticals or other high value compounds), including multistep natural product synthesis. Otsuka, S.; Tani, K. In *Transition Metals for Organic Synthesis (2nd Edition)*; Beller, M., Bolm, C., Eds.; Wiley-VCH: Weinheim, Germany, (2004); Vol. 1, p 199-209. The ability to control the formation and chemistry of alkenes is of central importance to organic synthesis in both industry and academia.

Alkene isomerization has been studied extensively in the literature. An examination of SciFinder revealed 6,405 hits using the search term "alkene isomerization" (7 Nov. 2013). Notwithstanding all the research and development of alkene syntheses, there remains a need today to better control both regiochemistry and stereochemistry of the alkene, particularly in the case of converting a 1-alkene to a trans-2-alkene, without either forming the cis-2-alkene or isomerizing further down the chain. The challenge is especially acute and unmet when the alkene contains no branching or substituents to control over isomerization. What one would like to have is a similar degree of control as that demanded and achieved routinely in asymmetric synthesis, where many reactions are optimized to exceed 90% e.e., corresponding to a product ratio of >20 to 1. Walsh, P. J.; Kozlowski, M. C. *Fundamentals of Asymmetric Catalysis;* University Science Books: Mill Valley, Calif., (2009); Jacobsen, E. N.; Pfaltz, A.; Yamamoto, H. *Comprehensive Asymmetric Catalysis;* Springer-Verlag: Berlin, (1999).

For example, one known alkene isomerization catalyst is selective for making and reacting with trans alkenes from terminal alkenes, but it is so active that it would not stop after one isomerization, unless the structure of the alkene substrate was such that the catalyst was impeded (a situation known as substrate control). What is needed is a new catalyst to control the reaction even in the case of a terminal alkene without special structural features.

In the more challenging case of unbranched alkenes or alkenes with remote branching, several known alkene isomerization catalysts have succeeded at regiocontrol at a >20 to 1 level, but did not offer significant stereocontrol, giving E/Z ratios in the range of 2 to 5, which essentially amounts to only thermodynamic control by substrate. Conventional catalysts that manage to achieve regiocontrol generally suffer from a lack of stereocontrol, and in most cases, are used at greater loadings or significantly higher temperatures. Veige's Cr(NCN)-pincer complex (10 mol %) offers some selectivity of 2-alkenes versus 3-alkenes (for hexene 95:5, octene 88:12) over 48 h at 85° C., however, the product cis:trans ratios were not specified. McGowan et al., *Organometallics* (2011), 30, 4949-4957.

Full conversion of 1-alkenes to 2-alkenes occurred using an unknown amount of $Ru_3(CO)_{12}$ as a catalyst provided a cis:trans ratio of product 2-octenes of 86:14. Sivaramakrishna et al., *Polyhedron* (2008), 27, 1911-1916. Recently, the isomerization of 1-octene to 2-octene (E/Z=65:26) has been reported, with small amounts of 3- and 4-octene, using a bulky Ir pincer complex (1 mol %) in 24 hours at high temperatures of 150° C., where NaOtBu was required as an additive. Chianese et al., *Organometallics* (2012), 31, 7359-7367. A slightly higher selectivity for the trans-2-alkene was observed using $Fe(acac)_3$ (5 mol %) in 10 hours at RT, where 50 mol % PhMgBr as additive was required, affording 97% 2-octene (E/Z=5:1, essentially the thermodynamic E/Z ratio), in addition to 3-alkene and unreacted starting 1-octene. Mayer et al., *ChemCatChem* (2011), 3, 1567-1571. Another study isomerized 1-hexene using $Ru(CO)_3(PPh_3)_2$ (0.5 mol %) to form 80% 2-hexene (E/Z=2:1) and 16% 3-hexene in 3 h at 40° C. Krompeic, S.; Suwinski, J.; Grobelny, J. *Pol. J. Chem.* (1996), 70, 813-818. Yet another study used $Fe_3(CO)_{12}$ (1 mol %) and 3 N KOH at 80° C. on 1-octene to make 96% 2-octene (E/Z=3.1:1). Jennerjahn et al., *ChemSusChem* (2012), 5, 734-739.

Although several of the known catalysts gave high positional selectivity, none of them deviated significantly from the thermodynamic E:Z ratio of about 4 to 1, and generally suffered from further isomerization of the 2- to the 3-alkene. One of the more selective conventional protocols used 50° C. and a Co—NHC complex (5 mol %), which generated in situ, giving 81% 2-tetradecene (E/Z=40:1) and 2% 3-alkene, in addition to 3% of 1-alkene. Kobayashi, T.; Yorimitsu, H.; Oshima, K. *Chem. Asian J.* (2009), 4, 1078-1083. The (E)-selectivity makes these results stand above other catalyst systems, but required the use of a specialized Grignard reagent ($Me_2PhSiCH_2MgCl$, 50-100 mol %) to form the selective catalyst, which is incompatible with many functional groups; for example, a normal benzoic acid ester was not suitable, and 2-alkene selectivity was eroded in some cases by polar substituents.

Our previously reported "alkene zipper" catalyst 2a does not generally solve the problem of simultaneous positional and geometric isomer control. (a) Grotjahn, D. B.; Larsen, C. R.; Gustafson, J. L.; Nair, R.; Sharma, A. *J. Am. Chem. Soc.* (2007), 129, 9592-9593; (b) Larsen, C. R.; Grotjahn, D. B. *J. Am. Chem. Soc.* (2012), 134, 10357-10360. Larsen, C. R.; Grotjahn, D. B. *J. Am. Chem. Soc.* (2012), 134, 15604; (c) Erdogan, G.; Grotjahn, D. B. *J. Am. Chem. Soc.* (2009), 131, 10354-10355; (d) Erdogan, G.; Ph.D. Thesis, Univ. of California at San Diego and San Diego State Univ. (2012). This catalyst system required substrate modifications, such as branching or the use of certain functional groups (e.g., an alcohol protecting group), to engineer the reaction conditions to achieve monoisomerization. In addition, many branched substrates cannot be selectively monoisomerized with catalyst 2a. Moreover, catalyst 2a is too active for the monoisomerization of non-functionalized, simple hydrocarbon alkenes, like 1-heptene, and the result is a mixture of trans-alkene isomer products. Finally, increasing the bulk of substituents on the phosphine ligand in 2a while keeping the cyclopentadienyl ligand constant were not successful in creating a catalyst capable of simultaneous positional and geometric isomer control. Erdogan, G.; Ph.D. Thesis, Univ. of California at San Diego and San Diego State Univ. (2012).

Other publications disclose substituted and unsubstituted cyclopentadienyl catalysts, but none of them, alone or together, teach a catalyst that can provide simultaneous positional and geometric isomer control. See e.g., US 2014/0228579 (Nikonov et al.), *Method For The Catalytic Reduction Of Acid Chlorides And Imidoyl Chlorides*; Machin et al., *Org. Lett.* (2009), 11(10), 2077-2080, *Ruthenium-Catalyzed Nucleophilic Ring-Opening Reactions of a 3-Aza-2-oxabicyclo[2.2.1]hept-5-ene with Alcohols*; Varela et al., *J. Am. Chem. Soc.* (2006), 9576-9577, *Ru-Catalyzed Cyclization of Terminal Alkynals to Cycloalkenes*; Yamamoto et al., *Org. Lett.* (2014), 16, 1806-1809, *Tandem Ruthenium-Catalyzed Transfer-Hydrogenative Cyclization/Intramolecular Diels-Alder Reaction of Enediynes Affording Dihydrocoumarin-Fused Polycycles*; and Severa et al., *Tetrahedron Lett.* (2009), Vol. 50, 4526-4528, *Air-tolerant C—C bond formation via organometallic ruthenium catalysis: diverse catalytic pathways involving ($C_5Me_5$)Ru or ($C_5H_5$)Ru are robust to molecular oxygen*. Moreover the above-mentioned publications do not teach that there are significant differences in product yields when substituted and unsubstituted cyclopentadienyl catalysts are used.

Thus, new catalysts and methods that are fast and efficient are needed to overcome the dual challenges of controlling the position of the double bond in a molecule, and controlling molecular shape in the form of cis/trans-selectivity in isomerization of terminal alkenes to their 2-isomers. A suitable catalyst would minimize or avoid thermodynamic equilibration of alkene isomers, for example, to provide trans-2-alkenes, of both non-functionalized and functionalized alkenes.

SUMMARY

The invention provides catalysts and methods to control the monoisomerization of 1-alkenes to trans-2-alkenes. In one embodiment, the invention provides an alkene isomerization catalyst of Formula I, Formula II, Formula III, Formula IV, or a combination thereof:

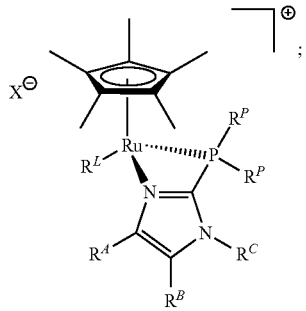
(I)

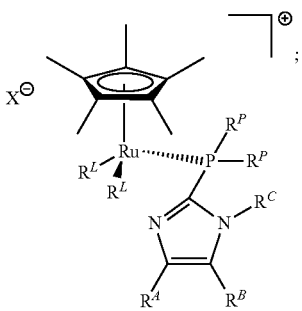
(II)

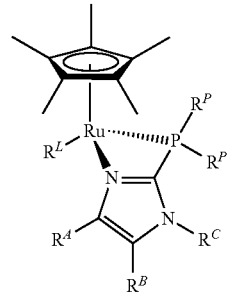
(III)

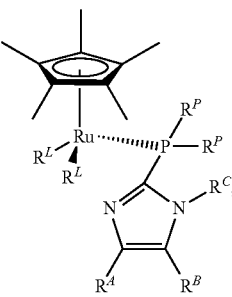
(IV)

wherein each $R^P$ is independently a branched ($C_3$-$C_{10}$)-alkyl, ($C_3$-$C_{10}$)-cycloalkyl, ($C_3$-$C_{15}$)-alkenyl, ($C_2$-$C_{12}$)-alkynyl, heterocyclyl, or an optionally substituted aryl or heteroaryl;

each $R^L$ is independently a neutral or anionic ligand, or is absent;

each $R^A$, $R^B$ and $R^C$ is independently hydrogen, a branched or linear ($C_1$-$C_{20}$)-alkyl, ($C_3$-$C_{10}$)-cycloalkyl, ($C_3$-$C_{15}$)-alkenyl, ($C_2$-$C_{12}$)-alkynyl, heterocyclyl, or an optionally substituted aryl or heteroaryl; and $X^-$ is a suitable counterion.

In one embodiment, one or both $R^P$ is iso-propyl. In another embodiment, one or both $R^P$ is iso-butyl. In still another embodiment, one or both $R^P$ is cyclohexyl. In yet other embodiments, one or both $R^P$ is adamantyl.

In certain embodiments, $R^L$ is alkyl nitrile, cycloalkyl nitrile, aryl nitrile, heteroaryl nitrile, heterocycloalkyl nitrile, alkylcarbonyl, CO, alkylamine, cycloalkylamine, alkenylamine, arylamine, amide, alkanol, cycloalkanol, water, ($C_3$-$C_{15}$)-alkenol, aryl alcohol, ketone, ether, aldehyde, alkene, halo, carboxylate, sulfonyl, sulfonate, phosphonyl, phosphinyl, or $N_2$.

In other embodiments, $R^L$ is nitrile free, for example, $R^L$ is carbonyl (e.g., alkylcarbonyl or arylcarbonyl), CO, alkylamine, cycloalkylamine, alkenylamine, arylamine, amide, alkanol, cycloalkanol, water, ($C_3$-$C_{15}$)-alkenol, aryl alcohol, ketone, ether, aldehyde, alkene, halo, carboxylate, sulfonyl, sulfonate, phosphonyl, phosphinyl, or $N_2$.

In one embodiment, one or both $R^L$ is an alkyl nitrile. In another embodiment, one or both $R^L$ is an aryl nitrile, particularly, an aryl halide substituted with electron withdrawing groups on the aryl moiety to make for a more labile ligand. Examples aryl nitriles having electron withdrawing groups include, but are not limited, to the following: $C_6F_5CN$, 4-$CF_3$—$C_6H_4$—CN, 3,5-($CF_3$)—$C_6H_3$—CN, 2,4-($CF_3$)—$C_6H_3$—CN.

In yet another embodiment, one or both $R^L$ is a neutral ligand such as a solvent molecule, for example, THF or acetone. In yet another embodiment, one or both $R^L$ is an anionic ligand, such as chloride, acetate, triflate, or an analog thereof. In one specific embodiment, one or both $R^L$ is acetonitrile. In another specific embodiment, one or both $R^L$ is THF. In yet another specific embodiment, one or both $R^L$ is acetone. In some embodiments, one or both $R^L$ is $N_2$. In various embodiments, one or both $R^L$ is absent.

In one embodiment, $R^P$ is a branched alkyl group. In one specific embodiment, $R^P$ is iso-propyl.

In one embodiment, $R^A$ is a branched alkyl group. In one specific embodiment, $R^A$ is tert-butyl.

In one embodiment, $R^B$ is an alkyl group or hydrogen. In one specific embodiment, $R^B$ is hydrogen.

In one embodiment, $R^C$ is an alkyl group. In one specific embodiment, $R^C$ is methyl.

In one embodiment, $X^-$ is an inorganic halide. In some embodiments, $X^-$ is $CF_3SO_3^-$, $BF_4^-$, $BPh_4^-$, $B(C_6F_5)_4^-$, or $B[C_6H_3$-$3,5$-$(CF_3)_2]_4^-$. In one specific embodiment, $X^-$ is $PF_6^-$.

In one embodiment, $X^-$ is an organic ion, such as alkoxide, aryl sulfonate, or carboxylate such as acetate.

In one embodiment, the catalyst is a mixture of two or more of Formula (I), Formula (II), Formula (III) and Formula (IV). In certain embodiments, the catalyst is a mixture of Formula (I) and Formula (II) or a mixture of Formula (III) and Formula (IV). In other embodiments, the catalyst is a mixture of Formula (I) and Formula (III) or a mixture of Formula (II) and Formula (IV). In yet other embodiments, the catalyst is a mixture of Formula (I) and Formula (IV) or a mixture of Formula (II) and Formula (III).

In one specific embodiment, the catalyst is formula 1:

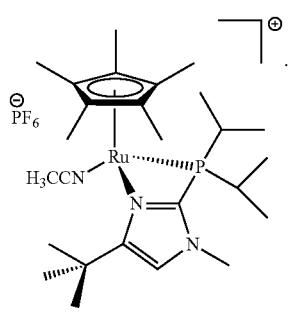

In another specific embodiment, the catalyst is formula 3:

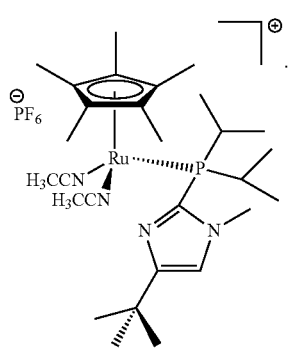

In yet another specific embodiment, the catalyst is a mixture of formulas 1 and 3.

The invention further provides methods of isomerizing a 1-alkene to an E-2-alkene. The methods can include contacting in a reaction mixture the 1-alkene with an effective amount of a catalyst of Formula I, Formula II, Formula III, Formula IV, or a combination thereof:

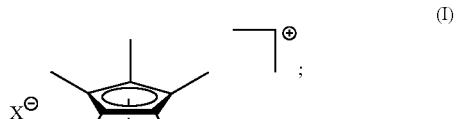

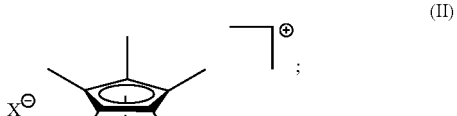

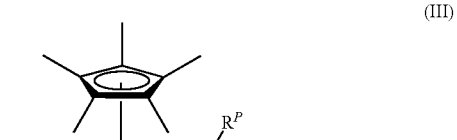

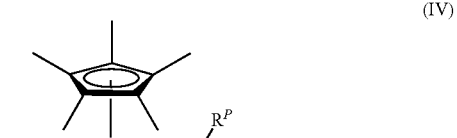

wherein the variables of the formulas are as defined above. The reaction mixture can optionally include a suitable solvent, and the method is carried out for a period of time sufficient to convert at least about 70% of the 1-alkene to an E-2-alkene. The time, selectivity and yield of the method can be as shown in any one or more of the tables in the Examples below.

In one embodiment, the catalyst of Formula I and the catalyst of Formula II are both present. In another embodiment, the catalyst of Formula III and the catalyst of Formula IV are both present. In yet another embodiment, more than one of the catalysts of Formulas I to IV are present.

In one embodiment, the reaction mixture comprises about 0.01 mol % to about 20 mol % of the catalyst of Formula I, or a mixture of the catalysts of Formula I and Formula II. In another embodiment, the reaction mixture comprises about 0.01 mol % to about 20 mol % of the catalyst of Formula III, or a mixture of the catalysts of Formula III and Formula IV.

In one embodiment, the temperature of the reaction mixture is about 0° C. to about 100° C., or about 20° C. to about 80° C. In some embodiments, at least about 75%, at least about 80%, at least about 85%, at least about 90%, or at least about 95% of the 1-alkene is converted to an E-2-alkene during the course of the reaction.

In one embodiment, less than about 5% of (E)-2-alkene products are obtained.

In some embodiments, the 1-alkene is linear.

In some embodiments, the 1-alkene contains one or more functional groups comprising atoms other than carbon and hydrogen. In one specific embodiment, the 1-alkene is an alkenol or an alkene silyl ether.

In one embodiment, a solvent system is present. In certain embodiments, the solvent system comprises acetone, THF or methylene chloride.

In some embodiments, a solvent system is not present; in such embodiments, the reaction mixture can contain only catalyst and alkene reactant.

The invention provides novel compounds of the formulas described herein, intermediates for the synthesis of compounds of the formulas described herein, as well as methods of preparing compounds of the formulas described herein. The invention also provides compounds of the formulas described herein that are useful as intermediates for the synthesis of other useful compounds. The invention also provides catalyst compositions that include a catalyst, an optional solvent system, and a substrate, for preparing trans-2-alkenes.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1A:
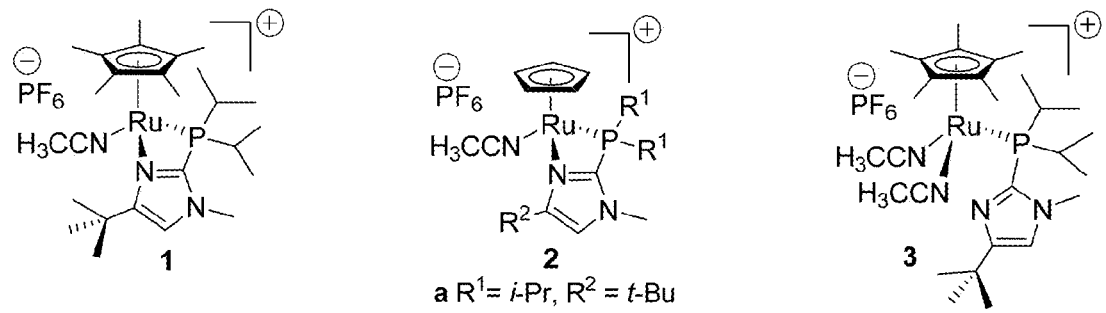
FIG. 1A and FIG. 1B. (A) Bifunctional ruthenium catalysts for control of alkene isomerization; (B) a schematic of alkene isomerization regiocontrol using catalyst 1.

The invention provides fast and efficient catalysts and methods for converting a 1-alkene to a trans-2-alkene, without forming significant amounts of the cis-2-alkene or isomerizing further down the alkene chain. The dual challenges of controlling the position of the double bond in a molecule, and controlling molecular shape in the form of cis/trans-selectivity in isomerization of terminal alkenes to their 2-isomers, is met by the new family of catalysts described herein. The novel catalysts avoid better than conventional catalysts the thermodynamic equilibration of alkene isomers, so that trans-2-alkenes of both non-functionalized and functionalized alkenes can be generated. The novel catalysts control the reaction even in the case of a terminal alkene having no special structural features.

We are not aware of other catalyst systems that offers the same combination of regiocontrol and stereocontrol as the novel catalysts described herein. Conventional catalyst systems that manage to achieve regiocontrol generally suffer from a lack of stereocontrol, and in most cases, are used at greater loadings (e.g., more than stoichiometric amounts) or significantly higher temperatures than the novel catalysts described herein. Due to the lack of control of conventional catalysts, mixtures are obtained, lowering the yield of any one isomer product, and further processing steps are required. Alkene metathesis is widely used in industry, and the catalysts described herein can be used to modify alkenes either before or after metathesis, which allows for more alkene products to be made from the same starting material.

Definitions and Usage of Terms

The following definitions and terms are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., (2001).

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, or in a reaction mixture.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound, reagent, or catalyst described herein, or an amount of a combination of compounds, reagents, or catalysts described herein, e.g., that is effective to form the intended products in a reaction mixture. Thus, an "effective amount" generally means an amount that provides the desired effect.

The term "substituted," as used herein, means the replacement of one or more atoms or radicals, usually hydrogen atoms, in a given structure with an atom(s) or radical(s) selected from a specified group. In the situations where more than one atom or radical may be replaced with a substituent selected from the same specified group, the substituents may be, unless otherwise specified, either the same or different at every position. Radicals of specified groups, such as alkyl, cycloalkyl, alkenyl, cycloalkenyl, alkynyl, arylalkyl, alkylaryl, heterocycloalkyl, aryl and heteroaryl groups, independently of or together with one another, may be substituents on any substituted group, unless otherwise stated, shown or known to be otherwise.

The term "alkyl," as used herein, means an unsubstituted or substituted, straight (linear) or branched, hydrocarbon chain having, preferably, from one to twenty-four carbon atoms, more preferably, from one to twelve carbon atoms, even more preferably, from one to eight carbon atoms, and most preferably, from one to six carbon atoms.

The term "cycloalkyl," as used herein, means a mono- or bicyclic, unsubstituted or substituted, saturated, stable nonaromatic carbocyclic ring, having, preferably, from three to fifteen carbon atoms, more preferably, from three to twelve carbon atoms. The carbon ring radical is saturated and may be bridged or fused, for example, benzofused, with one to three cycloalkyl, aromatic, heterocyclic or heteroaromatic rings. The cycloalkyl may be attached at any endocyclic carbon atom that results in a stable structure. Preferred carbocycles have from three to six carbons. Examples of carbocycle radicals include cyclopropyl, cyclobutyl, cyclopentyl, cyclohexyl, cycloheptyl and the like.

The term "alkenyl," as used herein, means an unsubstituted or substituted, unsaturated, straight (linear) or branched, hydrocarbon chain having at least one double bond present and, preferably, from two to fifteen carbon atoms, more preferably, from two to twelve carbon atoms.

The term "cycloalkenyl," as used herein, means an unsubstituted or substituted, unsaturated carbocyclic ring having at least one double bond present and, preferably, from three to fifteen carbon atoms, more preferably, from five to eight carbon atoms. A cycloalkenyl group is an unsaturated carbocyclic group. Examples of cycloalkenyl groups include cyclopentenyl and cyclohexenyl.

The term "alkynyl," as used herein, means an unsubstituted or substituted, unsaturated, straight or branched, hydrocarbon chain having at least one triple bond present and, preferably, from two to twelve carbon atoms, more preferably, two to ten carbon atoms.

The term "aryl," as used herein, means a substituted or unsubstituted, aromatic, mono- or bicyclic carbocyclic ring system having from one to two aromatic rings. The aryl moiety will generally have from 6 to 14 carbon atoms with all available substitutable carbon atoms of the aryl moiety being intended as possible points of attachment. Representative examples include phenyl, cumenyl, naphthyl, tetrahydronaphthyl, indanyl, indenyl and the like. If desired, the carbocyclic moiety can be substituted with from one to five, preferably, one to three moieties, such as mono- through pentahalo, alkyl, trifluoromethyl, phenyl, hydroxy, alkoxy, phenoxy, amino, monoalkylamino, dialkylamino and the like.

The term "heteroaryl," as used herein, means a mono- or bicyclic ring system containing one or two aromatic rings and at least one nitrogen, oxygen or sulfur atom in an aromatic ring. Heteroaryl groups (including bicyclic heteroaryl groups) can be unsubstituted or substituted with a plurality of substituents, preferably, one to five substituents, more preferably, one, two or three substituents (e.g., monothrough pentahalo, alkyl, trifluoromethyl, phenyl, hydroxy, alkoxy, phenoxy, amino, monoalkylamino, dialkylamino and the like). Typically, a heteroaryl group represents a cyclic group of five or six atoms, or a bicyclic group of nine or ten atoms, at least one of which is carbon, and having at least one oxygen, sulfur or nitrogen atom interrupting a carbocyclic ring having a sufficient number of pi ($\pi$) electrons to provide aromatic character. Representative heteroaryl (heteroaromatic) groups are pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazolyl, isothiazolyl, benzothiazolyl, benzoxazolyl, oxazolyl, pyrrolyl, isoxazolyl, 1,3,5-triazinyl and indolyl groups.

The term "heterocycloalkyl," as used herein, means an unsubstituted or substituted, saturated cyclic ring system having from three to fifteen members, preferably, from three to eight members, and comprising carbon atoms and at least one heteroatom as part of the ring.

The term "heterocyclic," as used herein, means an unsubstituted or substituted, saturated or unsaturated ring, comprised of carbon atoms and one or more heteroatoms in the ring. Heterocyclic rings may be monocyclic or polycyclic. Monocyclic rings preferably contain from three to eight atoms, most preferably, five to seven atoms. Polycyclic ring systems consisting of two rings preferably contain from six to sixteen atoms, most preferably, ten to twelve atoms. Polycyclic ring systems consisting of three rings contain, preferably, from thirteen to seventeen atoms, most preferably, fourteen to fifteen atoms. Each heterocyclic ring has at least one hetero atom. Unless otherwise stated, the heteroatoms may be independently selected from the following: nitrogen, sulfur and oxygen atoms.

The term "carbocyclic," as used herein, means an unsubstituted or substituted, saturated, unsaturated hydrocarbon ring, unless otherwise specifically identified. Carbocycles may be monocyclic or polycyclic. Monocyclic rings preferably contain from three to eight atoms, most preferably, five to seven atoms. Examples of monocyclic carbocycles include cyclohexyl and phenyl. Polycyclic rings having two rings preferably contain from six to sixteen atoms, most preferably, ten to twelve atoms, and those having three rings preferably contain from thirteen to seventeen atoms, most preferably, fourteen to fifteen atoms.

The term "alkoxy," as used herein, means an oxygen atom bonded to a hydrocarbon chain, such as an alkyl or alkenyl group (e.g., —O-alkyl or —O-alkenyl). Representative alkoxy groups include methoxy, ethoxy, and isopropoxy groups.

The term "acyl" or "alkylcarbonyl," as used herein, means a carbon to oxygen double bond, (e.g., R—C(=O)— where R is aryl or alkyl), which can be a radical of a carbonyl having the formula alkyl-CO—, aryl-CO—, arylalkyl-CO—, cycloalkyl-CO—, alkylcycloalkyl-CO— or heteroaryl-CO—. Representative acyl groups include acetyl, propionoyl, butanoyl and benzoyl groups.

The term "halo," "halogen" or "halide," as used herein, means a chloro, bromo, fluoro or iodo atom radical. Chlorides, bromides and fluorides are preferred halides.

The term "sulfonyl," as used herein, represents a group having the formula —S(O)$_2$—.

The term "sulfonate," as used herein, represents a group having the formula —S(O)$_3^-$. The sulfonate can be attached to a metal, or not attached and present as a free ion. Representative sulfonates include methanesulfonate (CH$_3$SO$_3$) and trifluoromethanesulfonate (CF$_3$SO$_3$).

Unless otherwise known, stated or shown to be to the contrary, the point of attachment for a multiple term substituent (multiple terms that are combined to identify a single moiety) to a subject structure is through the last named term of the multiple term.

The term "hydroxyalkyl," as used herein, means an alkyl group having at least one hydroxy substituent (e.g., —OH). Representative hydroxyalkyl groups include hydroxymethyl, hydroxyethyl and hydroxypropyl groups.

The term "carboxyalkyl" refers to an alkyl group that has a carboxyl substituent (e.g., —COOH). Representative carboxyalkyl groups include carboxymethyl (—CH$_2$CO$_2$H) and carboxyethyl (—CH$_2$CH$_2$CO$_2$H) groups, and derivatives thereof, such as the corresponding esters.

The term "aminoalkyl," as used herein, means an alkyl group substituted with an amine moiety (e.g., -alkylNH$_2$), such as aminomethyl.

The term "alkylamino," as used herein, means an amino moiety having from one or two alkyl substituents (e.g., —NH-alkyl), such as dimethylamino.

The term "alkenylamino," as used herein, means an amino moiety having from one or two alkenyl substituents, where the nitrogen atom of the amino group is not attached to the alkene-forming carbon atom (e.g., —NH—CH$_2$-alkenyl), such as dibutenylamino.

The term "arylamino," as used herein, means an amine moiety substituted with an aryl group (e.g., —NH-aryl).

The term "aminosulfonyl," as used herein, represents a group having the formula —SO$_2$NR$^x$R$^y$, where R$^x$ and R$^y$ are, independently of one another, each hydrogen, lower alkyl (e.g., from 1 to 8 carbon atoms) or aryl.

The term "carboxylate," as used herein, means the anion of a carboxylic acid such as an alkyl, cycloalkyl, aryl, or heterocyclic group that has a carboxyl substituent (e.g., —COOH). The carboxylate can be attached to a metal, or not attached and present as a free ion. Representative carboxylates include acetate (ethanoate) (CH$_3$CO$_2$) and propionate (propanoate) (CH$_3$CH$_2$CO$_2$—).

Except where stated otherwise, the definitions apply throughout the specification and claims. These definitions apply regardless of whether a term is used by itself or in combination with other terms, unless otherwise indicated. Hence, the definition of "alkyl" applies to "alkyl" as well as the "alkyl" portions of "alkyl nitrile".

When a variable appears more than once in a structural formula, for example, R$^L$ and R$^P$ in Formula (II), the identity of each variable appearing more than once may be independently selected from the definition for that variable.

Catalysts for the Control of the Monoisomerization of 1-alkenes

The novel catalysts described herein provide a degree of control similar to that demanded and achieved routinely in asymmetric synthesis, where many reactions are optimized to exceed 90% e. e., corresponding to a product ratio of >20 to 1. We have discovered a single, general catalyst (comprised of 1 and 3, FIG. 1A), which at the 1 mol % level routinely offers both regiocontrol and stereocontrol, with E/Z ratios>99 and product yields in excess of 95%.

As mentioned above in the background of the invention, our previously reported alkene zipper catalyst 2a did not generally solve the problem of simultaneous positional and geometric isomer control. We have tested the novel catalysts described herein and compared them to the alkene zipper catalyst 2a. The results are highlighted in Scheme 1. Although catalyst 2a is useful in many contexts, the problem remains that catalyst 2a is too active for the monoisomerization of non-functionalized, simple hydrocarbon alkenes, like 1-heptene (Scheme 1), and the result is a mixture of trans-alkene isomer products. Remarkably, the novel catalyst system comprising 1 and 3 allows for the selective monoisomerization of 1-heptene to trans-2-heptene in >95% yield, with <3% each of only two isomeric alkenes.

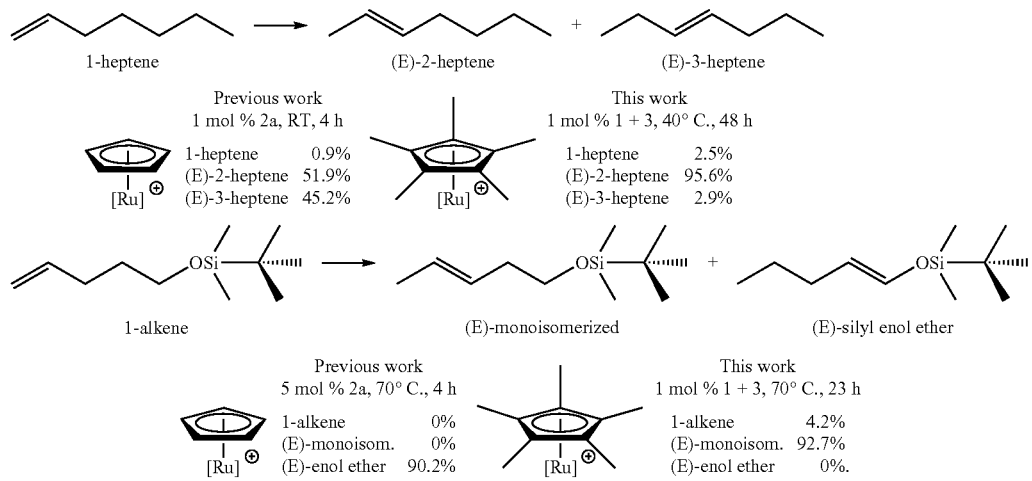

Scheme 1. Comparison results between the bifuntional [Cp*Ru]$^+$ catalyst 1 + 3 and the bifunctional [CpRu]$^+$ catalyst 2a.

To highlight the distinct differences in reactivity between the catalysts of Scheme 1, the tert-butyldimethylsilyl ether of pentenol was converted to exclusively the (E)-enol ether (3 bond movements, Scheme 1) with the previously reported [CpRu]+ catalyst 2a. In contrast to the previously reported catalyst, no enol ether was formed using the new [Cp*Ru]+ catalyst 1+3, and the (E)-monoisomerized product appeared in >92% yield.

Figure 1B:
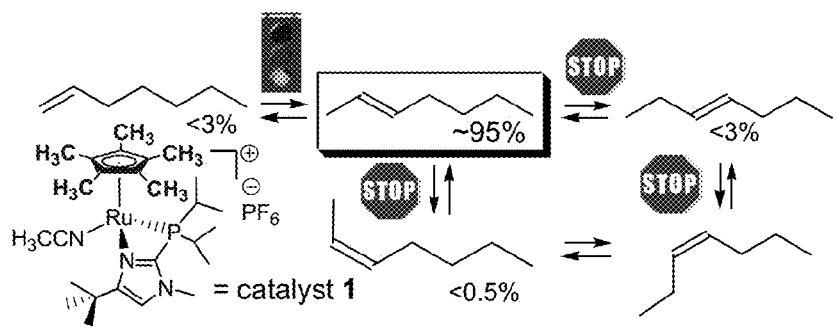

Table 1 below shows the effectiveness of 1+3. In order to achieve the improved selectivity highlighted in Scheme 1, we utilized a catalyst with an appropriate steric profile to discriminate between a 3-alkene and a 2-alkene, using the slightly greater bulk of an ethyl substituent compared to that of a methyl substituent. We tried increasing the steric bulk of the $R^1$ and $R^2$ groups of the N-heterocyclic phosphine ligand in 2a (FIG. 1), but even at best, positional isomerization resulted in a mixture of internal isomers (E)-2- and 3-heptene from 1-heptene. Erdogan, G., Ph.D. Thesis, Univ. of California at San Diego and San Diego State Univ. (2012). After considerable experimentation, we discovered a sufficiently improved selective catalyst (1), not by changing the phosphine ligand, but by modifying the ancillary Cp ligand, eventually complexing $Cp*Ru(NCCH_3)_3^+$ with the same ligand as in 2a. The starting material $Cp*Ru(NCCH_3)_3^+$ has been reported to perform the redox isomerization of functionalized allylic alcohols to the corresponding carbonyl compound in refluxing $CH_3CN$. Bouziane et al., *Tetrahedron* (2008), 64, 11745-11750. However, in a control experiment (Table 1, entry 2d), we see that under conditions where 1+3 is highly effective, $Cp*Ru(NCCH_3)_3^+PF_6^-$ only slowly consumes 1-heptene, giving a mixture of all positional and geometric isomers. Of more significance are the control experiments (Table 1, entries 2e and 2f) showing that phosphine complexes without the pendant heterocycle are at least 3000 times slower than 1+3.

TABLE 1

Control of positional and geometric isomer selectivity in monoisomerization of non-functionalized 1-alkenes to the corresponding (E)-2-alkene using catalyst 1 + 3 (entries 1-6) and control experiments (entries 1a, 2a-2f)[a].

| entry | reactant | catalyst | mol % | time | 1-alkene remaining (%) | (E)-2-alkene yield (%) | (E)-3-alkene yield (%) | (Z)-2-alkene yield (%) |
|---|---|---|---|---|---|---|---|---|
| 1 | | 1 + 3 | 1 | 22 h | 4.6 | 95.5 | 1.1[b] | <0.5[c] |
| | | | | 48 h | 2.3 | 95.5 | 2.1[b] | <0.5[c] |
| 1a | | 2a[d] | 1 | 2 h | 1.6 | 75.5 | 24.2 | <0.5[e] |
| 2 | | 1 + 3 | 1 | 22 h | 6.0 | 93.3 | 1.6 | <0.5[c] |
| | | | | 48 h | 2.5 | 95.6 | 2.9 | <0.5[c] |
| 2a | | 2a[d] | 1 | 10 min | 1.2 | 59.9 | 38.3 | <0.5[e] |
| | | | | 4 h | 0.9 | 51.9 | 45.2 | <0.5[e] |
| 2b | | $RhCl_3/BH_3$[f] | | | 0.7 | 43.3 | 36.0 | 12.7 |
| 2c | | calculated[f] | | | 0.5 | 59.7 | 39.8 | 0 |
| 2d | | $Cp*Ru(CH_3CN)_3^+\ PF_6^-$[g] | 2 | 66 h | 81.8 | 8.5 | 4.2 | 2.0 |
| 2e | | $Cp*Ru(CH_3CN)_2(PiPr_3)^+\ PF_6^-$ | 4 | 72 h[h] | 97.9 | 0.7 | <0.5 | <0.5 |
| 2f | | $Cp*Ru(CH_3CN)_2(PiPr_2Ph)^+\ PF_6^-$ | 4 | 72 h[h] | 99.0 | 0.2 | <0.5 | <0.5 |
| 3 | | 1 + 3 | 1 | 22 h | 6.4 | 92.0 | 0.8 | <0.5[c] |
| | | | | 48 h | 2.7 | 95.7 | 2.4 | <0.5[c] |
| 4 | | (1 + 3) + $CH_3CN$ | 1 | 22 h | 21.8 | 77.4 | 1.2 | <0.5[c] |
| | | | | 48 h | 6.2 | 91.8 | 1.1 | <0.5[c] |
| | | | | 97 h | 2.7 | 94.7 | 2.7 | <0.5[c] |
| 5 | | 3 + $CH_3CN$ (catalyst made in situ)[i] | 1 | 22 h | 41.0 | 60.4 | <0.5[e] | nd |
| | | | | 48 h | 15.9 | 85.3 | 0.9 | <0.5[c] |
| | | | | 97 h | 4.5 | 95.6 | 1.8 | <0.5[c] |
| 6 | | 1 + 3[j] | 2 | 21 h | 7.7 | 90.8 | 1.3 | nd |
| | | | | 48 h | 2.6 | 95.8 | 2.2 | nd |

[a]Unless otherwise specified, 1 mol % 1 + 3 (which refers to a mixture of 1 and 3), acetone-$d_6$, 40° C. Yields were determined by NMR integrations versus internal standard. Confirmatory alkene ratios were obtained using GC; see Example 1 for details. Less than a certain value means none detected, with the value given being an estimated limit of detection. "nd" = not determined.
[b](E)-3-hexene is better detected by NMR, because of the overlap of the GC peaks of (E)-3-hexene and (E)-2-hexene.
[c]Limit of detection using GC, comparison with authentic sample.
[d]0.7 (entry 1a) or 1.0 mol % (entry 2a) 2a, acetone-$d_6$, RT.
[e]Limit of detection using NMR.
[f]Values from reference Morrill, T. C.; D'Souza, C. A. *Organometallics* (2003), 22, 1626-1629. Using $RhCl_3/BH_3$ (entry 2b); in addition, 7.3% (Z)-3-heptene is formed. Entry 2c is based on heats of formation, and refers to values expected if only the three isomers 1-, (E)-2, and (E)-3-heptene could be formed.
[g]2 mol % $Cp*Ru(NCCH_3)_3^+\ PF_6^-$, 40° C. Alkene % values are ratios analyzed by GC; a fifth peak, likely that of (Z)-3-heptene, 3.6%.
[h]For data at earlier or later time points, and for analysis showing that 1 + 3 is >3000 times faster than the controls, see text below.
[i]Catalyst made in situ by mixing $Cp*Ru(NCCH_3)_3^+\ PF_6^-$ and phosphine ligand (1 mol % each), which gives bis(acetonitrile) complex 3 plus 1 equiv. of free $CH_3CN$.
[j]Using 2 mol % 1. For data using 5 mol % 1 at RT, see Example 1; after 97 h, 93.3% (E)-2-decene and 5.7% 1-decene remaining.

Table 1 shows how the new [Cp*Ru]+ complex 1+3 succeeds at controlled formation of trans-2-alkenes from linear hydrocarbon 1-alkenes, which as discussed above, is an important challenge for catalyst control. Table 2 below focuses on compounds that are functionalized, but far from the alkene, thus offering little chance of steric or electronic control of isomerization. In all cases, the generation of exclusively (E)-2-alkenes was observed.

after 22 h at 40° C., 1-heptene (1.8%) was formed, showing ready equilibration between 1- and (E)-2-alkene. A small amount (1.0%) of (E)-3-heptene was also formed, even though (E)-2- and (E)-3-heptene are almost equally stable.

TABLE 2

Monoisomerization of functionalized 1-alkenes to the corresponding (E)-2-alkenes using catalyst 1 + 3.[a]

| Entry | Reactant | Temp, ° C. | Time (h) | 1-alkene remaining (%) | (E)-2-alkene yield (%) |
|---|---|---|---|---|---|
| 1 | ⌇⌇⌇OH | 40 | 5<br>24 | 16.9<br>2.7 | 81.7<br>94.4 |
| 2a | ⌇⌇⌇OSi(tBu)Me₂ | 40 | 23<br>48 | 14.3<br>4.7 | 85.2<br>95.1 |
| 2b |  | 70 | 5<br>23 | 5.8<br>4.2 | 92.2<br>92.7 |
| 3[b] | ⌇⌇⌇OSi(tBu)Ph₂ | 40 | 23<br>48 | 8.2<br>5.0 | 87.9[c]<br>90.2[c] |
| 4 | ⌇⌇⌇⌇⌇OH | 70 | 5 | 4.2 | 95.1[d] |
| 5 | ⌇⌇⌇⌇CH(OH)CH₃ | 40 | 23<br>46 | 6.3<br>2.2 | 93.4<br>97.7 |

[a]1 mol % 1 + 3 (which refers to a mixture of 1 and 3), acetone-d₆. Yields were determined by NMR integrations versus internal standard.
[b]2 mol % 1 + 3 with 6 mol % added ligand.
[c](E)-3-alkene also seen, 0.6 and 1.0% after 23 and 48 hours. Also seen was ca. 1% of Cp*Ru-arene complex(es), likely of product.
[d]3-alkene (2.1%) was also observed.

Optimization of conditions performed on 1-octene, as detailed in Example 1 below, led to reaction conditions of 1 mol % 1+3 in acetone-d₆ solvent at 40° C. Differences in rate of reaction or selectivity when either 1 or 2 mol % 1+3 is used are modest, but 5 mol % allows room temperature reactions (see footnote j of Table 1). Higher temperatures (e.g. 70° C.) were tested in an effort to speed reactions, but in general, tended to cause some over-isomerization of substrates with a challenging lack of hindrance, such as the linear hydrocarbons in Table 1 or entries 3 and 4 of Table 2. Nitromethane gave rates comparable to those seen in acetone, but solubility was poorer, and methylene chloride gave slower reactions.

The optimum conditions for 1-octene were also applied to hexene, heptene, and decene (Table 1). NMR data was used to determine yields, and GC data was used to confirm alkene ratios. Major $^1$H and $^{13}$C NMR resonances for cis- and trans-internal isomers are distinct enough to detect many of the components and determine yields. The (E)-2-alkene product dominated in all cases (ca. 95% yield) after 48 h. Looking at the 21 h or 22 h data, and taking into account the use of 2 mol % catalyst for 1-decene, one discerns a slight decrease in rate on going from the smallest alkene to the largest, which may reflect greater effective steric hindrance from the longer alkyl chains. For all alkenes, less than 0.5% (detection limit) of (Z)-2-alkene was formed, but significantly, no more than 3% of over-isomerization (in the form of (E)-3-alkene) was seen. The small amount of 1-alkene remaining (2 to 3%) will likely never go away, because of the thermodynamic stabilities of 1-alkene and (E)-2-alkene; in a control experiment starting with pure (E)-2-heptene, Morrill, T. C.; D'Souza, C. A. *Organometallics* (2003), 22, 1626-1629; a separate control experiment was run starting with (E)-3-heptene, which after 22 and 111 h at 40° C., led to 0.9% and 1.3% (E)-2-heptene, respectively, but no detectable 1-heptene.

The results described herein are notable considering the previously reported calculated thermodynamic distribution of heptene positional and geometrical isomers: 1-heptene (0.4%), (E)-2 (48.5%), (Z)-2 (11.7%), (E)-3 (32.4%), and (Z)-3-heptene (6.9%), values which were approached closely in experiments using the RhCl₃/BH₃ catalyst system of Morrill and D'Souza. Morrill, T. C.; D'Souza, C. A. *Organometallics* (2003), 22, 1626-1629. If only the terminal isomer and two internal trans-isomers are possible, as seen by the values based on heats of formation in Table 1, entry 2c, the distribution of the three alkenes in the mixture would be 1-heptene (0.5%), (E)-2-heptene (59.7%), and (E)-3-heptene (39.8%), and these values are closely approached by the alkene zipper catalyst 2a (entry 2a), confirming the accessibility of the less hindered CpRu derivative to the terminal alkene and all internal (E) isomers.

The preparation and characterization of 1+3 deserve comment, in part, because recent experiments point to the ability to use a catalyst prepared in situ, and in part, because the samples of 1 tested were all mixtures of 1 and bis(acetonitrile) species 3. Adding phosphine to Cp*Ru(NCCH₃)₃⁺ in a 1:1 molar ratio afforded a 1:1 mixture of free CH₃CN and bis(acetonitrile)phosphine complex 3 within minutes. Removal of solvent left essentially pure 3, with some chelate complex 1. Adding fresh acetone and evaporating it, and repeating this treatment, led to mixtures of 1 and 3, typically in a ratio ranging from 1:5 to 1:2, which were used as the catalyst to obtain the results in Tables 1 and 2. Various NMR signals for 1 were broad for temperatures between +30 and −70° C. used for observation, but at −20° C., all $^1$H and $^{13}$C NMR resonances for 1 and 3 could be assigned using 1D and 2D NMR methods, except for the broadened peaks of the nuclei in the iso-propyl groups on phosphorus. The mutual steric hindrances presented by the Cp* methyls groups and the phosphine iso-propyl groups are assumed to account for the broadened NMR spectra. Notable is the one-bond coupling between P and the imidazole carbon directly attached, $^1J_{CP}$=58.0 Hz in 3 and 28.5 Hz in 1. We have previously reported that the sharply reduced coupling can be taken as diagnostic for the four-membered ring formed by a chelating imidazolylphosphine. (a) Grotjahn, D. B.; Gong, Y.; DiPasquale, A. G.; Zakharov, L. N.; Rheingold, A. L. *Organometallics* (2006), 25, 5693-5695.; (b) Grotjahn, D. B.; Gong, Y.; Zakharov, L. N.; Golen, J. A.; Rheingold, A. L. *J. Am. Chem. Soc.* (2006), 128, 438-453. Also significant is that the formation of the four-membered chelate engenders an upfield shift of the $^{31}$P NMR resonance by 8.4 ppm.

The zipper catalyst 2a was formed as a single species. Grotjahn, D. B.; Larsen, C. R.; Gustafson, J. L.; Nair, R.; Sharma, A. *J. Am. Chem. Soc.* (2007), 129, 9592-9593. However, experience with many structures of type 2 shows that not all potentially chelating phosphines can be induced to convert fully to chelates like 1 or 2a, instead forming mixtures. Grotjahn, D. B.; Erdogan, G.; Larsen, C. L., unpublished results. Given that ligand exchange on CpRu $(CH_3CN)_3^+$ is dissociative, presumably, 1 and 3 both enter into alkene isomerization by loss of acetonitrile (as was shown to be the case for 2a), followed by alkene binding and allylic deprotonation. Luginbühl et al., *Inorg. Chem.* (1991), 30, 2350-2355. With this is mind, we have documented the effect of nitrile amounts on isomerization rate, and show conclusively that the unprecedented positional selectivity of alkene isomerization by 1+3 is not caused by ca. 1.7 equiv. of nitrile per Ru in the system (compared with reactions using pure 2a, where the nitrile:Ru ratio is only 1 to 1). Accordingly, a control experiment using 1+3 with added $CH_3CN$ (1 equiv) was performed.

Table 1, entry 4, shows that adding 1 equiv. of nitrile to 1+3 (giving nitrile:Ru ratio ca. of 2.7 to 1) slows catalysis, but only by about two-fold, providing the same excellent selectivity. Significantly, as seen from Table 1, entry 5, mixing Cp*Ru(NCCH$_3$)$_3^+$PF$_6^-$ and the requisite phosphine (1 mol % each) to afford 3+CH$_3$CN (nitrile:Ru ratio ca. of 3 to 1) was just as effective, offering an alternative, convenient mode for use of the Cp*Ru catalyst system. In summary, the precise ratio of 1 to 3 in preparation of the catalyst does not seem to affect the rate or selectivity of isomerization, where even 3+CH$_3$CN formed in situ gave the same selectivity, with a slightly reduced rate (about half) than seen using 1+3 mixtures.

Table 2 shows that functionalized compounds can also be converted to (E)-2-alkenes with high selectivity using 1 mol % 1+3. Pent-4-en-1-ol is transformed into >94% 3-penten-1-ol in a facile manner within 24 h (entry 1). The monoisomerization of 4-penten-1-ol with cis-Pt(DMSO)$_2$Cl$_2$ in water only gave 50% conversion to 3-penten-1-ol, after one day, with no mention of geometric selectivity. Alemán et al., *Dalton Trans.* (2010), 39, 10601-10607. The corresponding silyl ether (entry 2) can be smoothly converted to the trans-monoisomerized product, without over-isomerization at 40° C., and not until 23 h at 70° C. (2.5%). It has been previously reported that the monoisomerization of the hexenyl homologue of entry 2 with two multicomponent catalysts, ((allyl)Pd or Ni halide dimer, phosphine, and AgOTf) can be produced in a 80-95% yield, but this system also provides E/Z ratios near 3.7:1, which are likely close to the thermodynamic values. Lim et al., *J. Org. Chem.* (2009), 74, 4565-4572.

Here, Table 2, entry 4 ((a) Dec-9-en-1-ol has been reported to isomerize in the presence of a ruthenium hydride complex at 70° C. to an internal isomer, said to be likely dec-8-en-1-ol on the basis of $^1$H NMR spectroscopy; (b) Lee et al., *Organometallics* 2009, 28, 1758-1775) and Table 2, entry 5, show that longer chains bearing an alcohol at the remote end will work equally well, neither being slowed by the polar functional group, nor suffering from reduced positional or geometric isomer selectivity.

Experiments with aromatic reactants suggest that they are not as well-tolerated by 1+3 compared to the CpRu zipper catalyst 2a. The tert-butyldiphenylsilyl ether of pent-4-en-1-ol was transformed to the trans-monoisomerized product of interest (29%) before catalyst deactivation occurred by liberation of the phosphine ligand and what appeared to be irreversible arene complex formation (as evidenced by loss of $^{31}$P NMR peaks for 1 and 3, appearance of a peak for free phosphine, and appearance of $^1$H resonances between 5.9 and 6.2 ppm tentatively assigned to metalated arene). Perhaps because of the release of steric strain, dissociative phosphine loss from 1 is more pronounced than from 2a. We note that a phosphine-free species Cp*Ru(NCCH$_3$)$_3^+$PF$_6^-$ is a poor catalyst (Table 1, entry 2d), so the activity and high selectivity exhibited by 1 appears to benefit from the phosphine. Importantly, solving the arene binding problem is possible. The successful result of Table 2, entry 3, was achieved with 2 mol % 1 and added bifunctional imidazolylphosphine ligand (6 mol %), which sufficiently suppressed Cp*Ru-arene complex formation to allow for >90% yield of monoisomerized product to form.

These results show that the novel Cp*Ru$^+$ catalyst 1+3 offers unparalleled control of both position and geometry in the isomerization of 1-alkenes to (E)-2-alkenes, even when polar substituents are present. Protic and carbonyl (acetone solvent) functional groups are tolerated, likely because a strong base, nucleophile, or acid is not present. Preformed catalyst, as well as 3 formed in situ from Cp*Ru(NCCH$_3$)$_3^+$PF$_6^-$ and phosphine ligand, were shown to have similar high catalyst control. The novel catalyst systems described herein provide a robust toolbox of catalysts and chemistry for selective alkene transformation.

Figure 24:
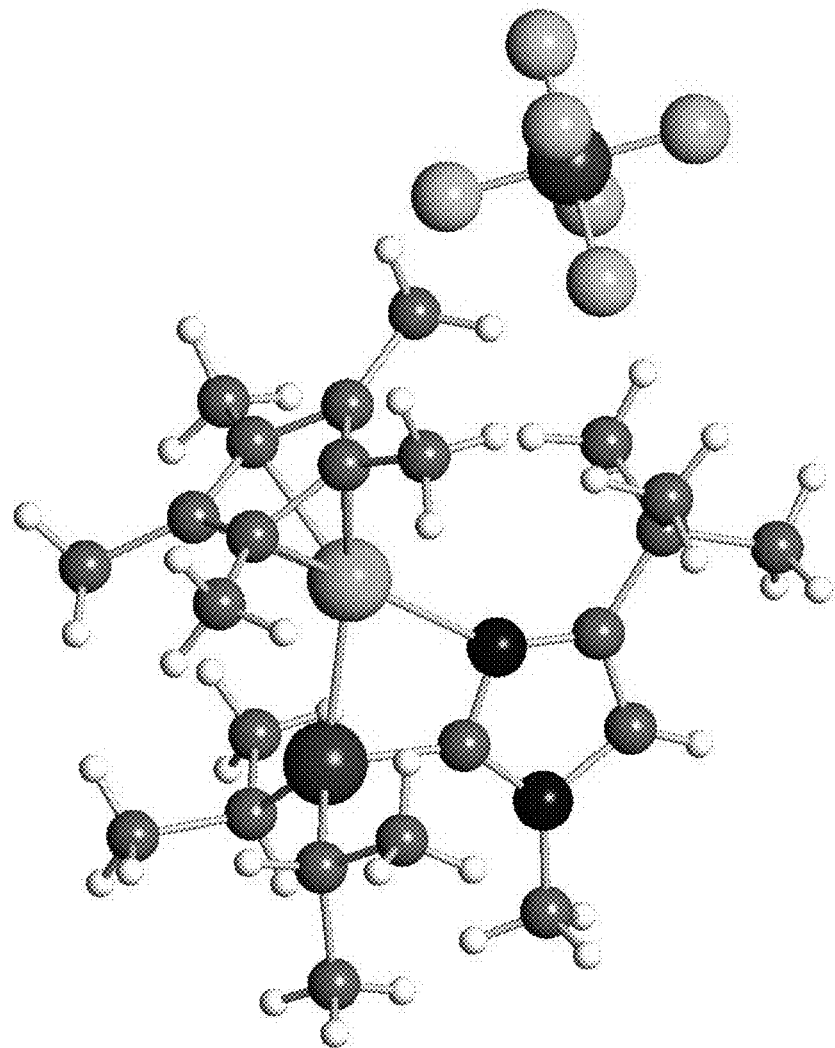
FIG. 24. X-ray crystal structure of nitrile-free catalyst Y.

Without restricting consideration of catalyst operation to any one mechanism, we have shown that catalysts faster than mixtures of 1+3, yet still as selective, can be made by using ligands other than acetonitrile, which could be expected to dissociate more completely or quickly from the metal. In Scheme 2 below, we added phosphine 4 to the ruthenium tetramer in THF solvent, forming a deep blue solution, which suggests the formation of a formally 16-electron species 5. The strong coloration of a 16-electron Cp*Ru(PR$_3$)X species has been previously reported. Gutsulyak et al., *Organometallics* (2009), 28, 2655-2657, and references 14 to 16 therein; Campion et al., *J. Chem. Soc., Chem. Commun.* (1988), 278. This solution was relatively inefficient as an alkene isomerization catalyst, but became extremely active after addition of thallium(I) hexafluorophosphate, which can form 8 and/or 9 (S=THF) in THF solvent. Data shows that the new catalyst is much faster than the catalyst 1+3 in the isomerization of 1-hexene to (E)-2-hexene. Table Z below shows how within only 6 h at room temperature, only 0.1 mol % catalyst was needed to achieve the same results as 1+3 in 48 h at 40° C. using 1 mol % loading. Data also show that when made in acetone and crystallized, species 9 (X=PF6) is formed without presence of a solvent molecule S (see FIG. 24).

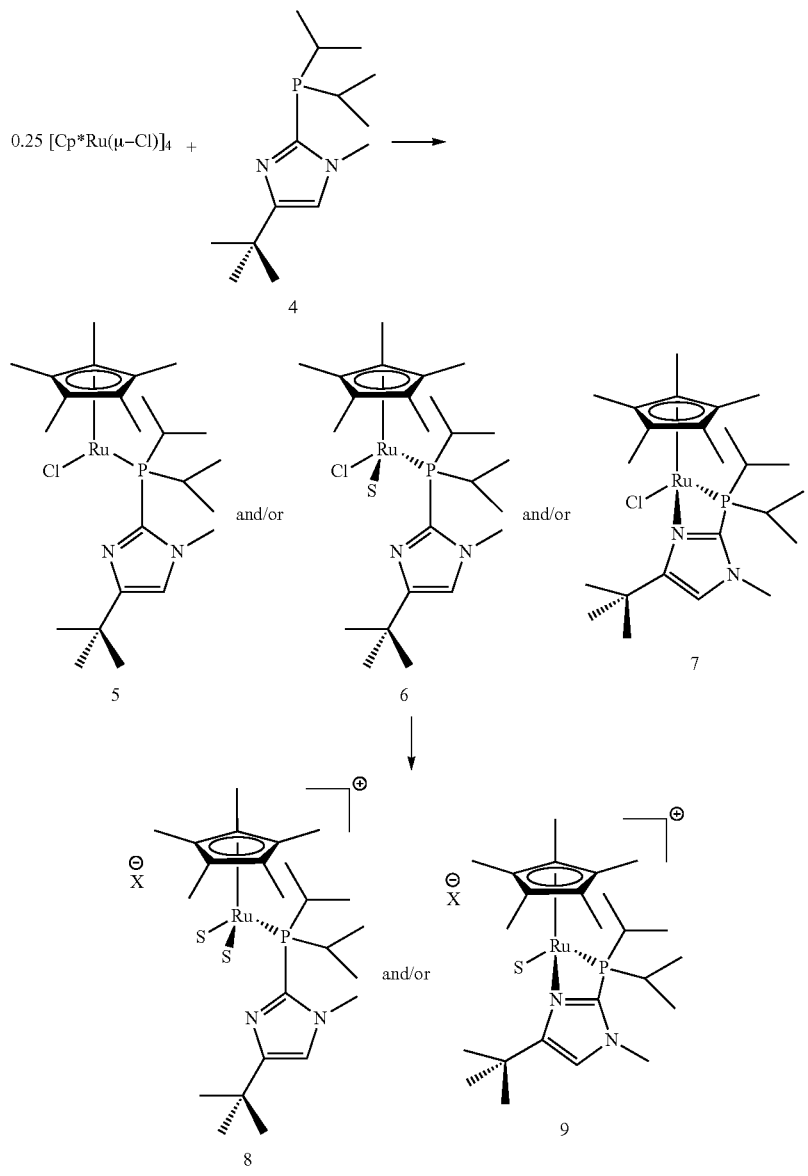

Scheme 2. Acetonitrile-free catalysts.

S = solvent

In some embodiments S is $N_2$. Thus, S can be solvent, $N_2$, or absent.

The novel catalysts described herein provide a fast, efficient and broad-based means for converting a 1-alkene to a trans-2-alkene, without forming any significant amounts of the cis-2-alkene or isomerizing further down the alkene chain. The combination of regiocontrol and stereocontrol provided by the novel catalysts can be applied to a wide range of substrates (e.g., substrate independence), which provides the practitioner with a powerful tool for many different situations.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Catalyst Control of the Monoisomerization of 1-Alkenes to Trans-2-Alkenes

I. General Experimental.

Reactions were performed under dry nitrogen, using a combination of Schlenk line and glovebox techniques.

Acetone-$d_6$ received from Cambridge Isotope Labs was further deoxygenated by bubbling nitrogen gas through the liquid. NMR tube reactions were performed in resealable NMR tubes (J. Young).

Unless otherwise specified, NMR data were measured at 30° C. Varian spectrometers were used: a 500-MHz NOVA (500 MHz listed below for $^1$H=499.940 MHz and 125.7 MHz for $^{13}$C=125.718 MHz), and a 400-MHz Varian NMR-S (400 MHz listed below for $^1$H=399.763 MHz and 100 MHz for $^{13}$C=100.525 MHz).

$^1$H and $^{13}$C NMR chemical shifts are reported in ppm, referenced to solvent resonances ($^1$H NMR: δ 2.05 for CHD$_2$COCD$_3$ and $^{13}$C NMR: δ 29.92 for CD$_3$COCD$_3$). $^1$H NMR signals are given followed by multiplicity, coupling constants J in Hertz, integration in parentheses. For complex coupling patters, the first coupling constant listed corresponds to the first splitting listed, e.g. for (dt, J=3.2, 7.9, 1H) the doublet exhibits the 3.2-Hz coupling constant.

Elemental analyses were performed at NuMega Laboratories (San Diego, Calif.).

II. Preparation and Characterization of 1 and 3.

tris(acetonitrile)Pentamethylcyclopentadienylruthenium (II) hexafluorophosphate (116.9 mg, 0.2317 mmol) was weighed in a scintillation vial equipped with a magnetic stir bar in a glove box, and deoxygenated acetone (6 mL) was added. In a separate vial, the requisite phosphine (59.4 mg, 0.2336 mmol) was weighed and deoxygenated acetone (1 mL) was added. The phosphine dissolved in acetone was added dropwise to the ruthenium complex solution, and deoxygenated acetone was used to rinse the vial. The mixture was allowed to stir in the glovebox at ambient temperature overnight, though formation of 3 occurs within 15 min [see below]. The solvent was evaporated forming a foam, to which was added acetone. The process was repeated four times within 2 h. After concentration, the residue was stored under vacuum to afford a yellow-brown foam (152.6 mg vs. 156.7 mg theoretical yield for pure 1 and 166.3 mg for pure 3; given composition, yield is about 93%).

Analysis by $^1$H and $^{31}$P{$^1$H} NMR spectroscopy showed chelate complex 1 and non-chelated complex 3 in a ratio of ca. 1 to 3. In various experiments, 3 was the major component of the mixture. The ratio obtained varied somewhat from batch to batch, from about 1 to 3 to 1 to 5. Not all NMR signals for 1 could be determined with certainty because at any temperature used between +30 and −70° C., at least some of the peaks were broadened in either or both $^1$H and $^{13}$C NMR spectra. At −20° C., all resonances except for those involving the iso-propyl groups on P could be identified using 1D and 2D spectra, which are summarized graphically in FIG. 2. Combustion analysis for a sample from another preparation was run: C, 45.67; H, 6.62; N, 7.45. Anal. Calcd. for a 1:3 mixture of 1 and 3: C, 46.33; H, 6.73; N, 7.41. Anal. Calcd. for pure 1: C, 46.15; H, 6.70; N, 6.21. Anal. Calcd. for pure 3: C, 46.86; H, 6.74; N, 7.81.

Chelate (1) partial $^1$H NMR (500 MHz, acetone-$d_6$, −20° C.) δ 6.97 (s, 1H), 3.73 (s 3H), 2.45 (s, 3H), 1.71 (d, J=1.5, 15H), 1.29 ppm (s, 9H). Partial $^{13}$C {$^1$H} NMR (125.73 MHz, acetone-$d_6$, −20° C.) δ 153.1 (d, J=14.3), 148.3 (d, J=28.5), 127.6, 119.8, 82.2 (d, J=2.3), 34.7, 31.9, 29.6 (overlapping with one peak from solvent, but identified by HMBC crosspeak with proton signal at 1.29 ppm), 11.2, 3.7 ppm. $^{31}$P{$^1$H} NMR (202.38 MHz, acetone-$d_6$, −20° C.) δ 28.3 ppm (s).

Bis acetonitrile complex (3) partial $^1$H NMR (500 MHz, acetone-$d_6$, −20° C.) δ 7.01 (s, 1H), 3.67 (s 3H), 2.64 (s, 6H), 1.36 (s, 15H), 1.24 ppm (s, 9H). Partial $^{13}$C NMR (125.73 MHz, acetone-$d_6$, −20° C.) δ 151.7 (d, J=7.8), 142.5 (d, J=58.0), 128.1 (sl br s), 119.4, 86.8 (d, J=1.8), 34.0 (d, J=0.9), 32.3, 30.4, 8.9, 4.0 ppm. $^{31}$P {$^1$H} NMR (202.38 MHz, acetone-$d_6$, −20° C.) δ 36.7 ppm (s).

Figure 2A:
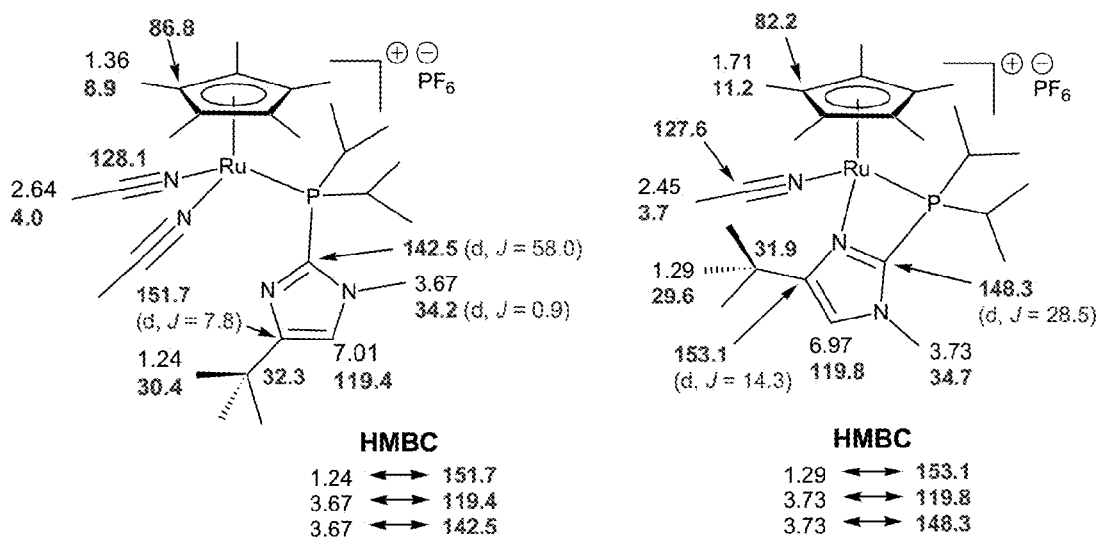
FIG. 2A-D. 2A: Graphical summary of $^1$H (black) and $^{13}$C (red, bold) NMR data for 1 and 3, observed as a mixture in acetone-$d_6$ at −20° C. Selected key gHMBC crosspeaks allowing identification of imidazole carbons are shown. 2B-D: $^1$H, $^{13}$C, and $^{31}$P NMR spectra acquired at −20° C. for a mixture 1 and 3.
Figure 2B:
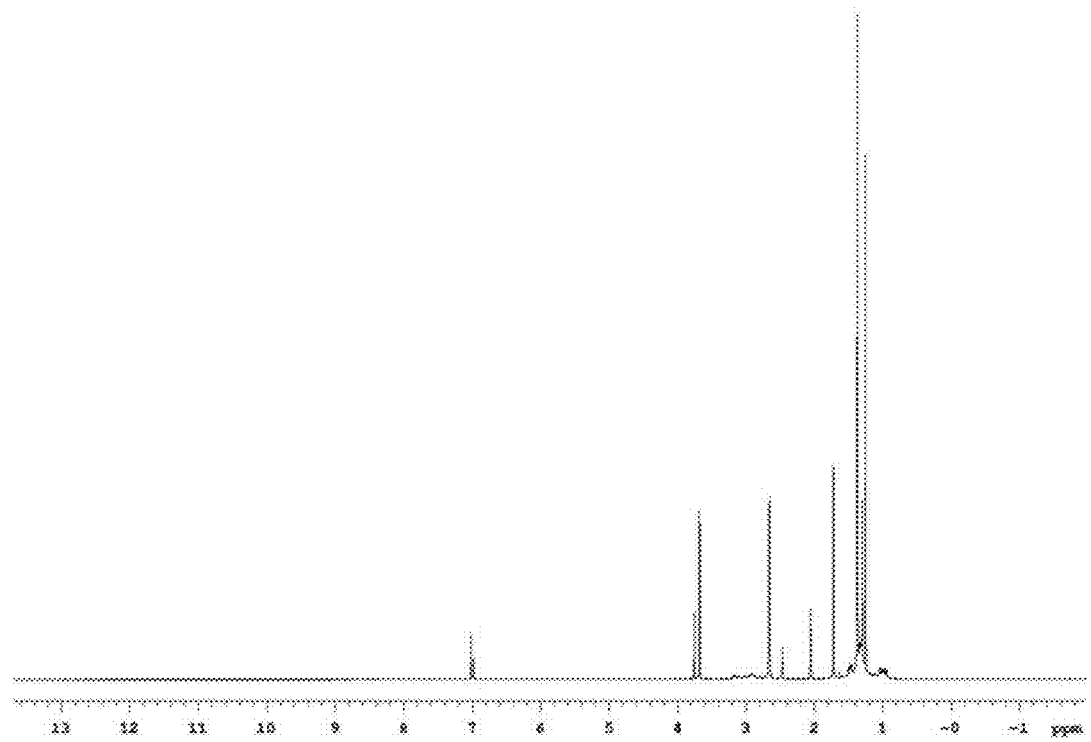
Figure 2C:
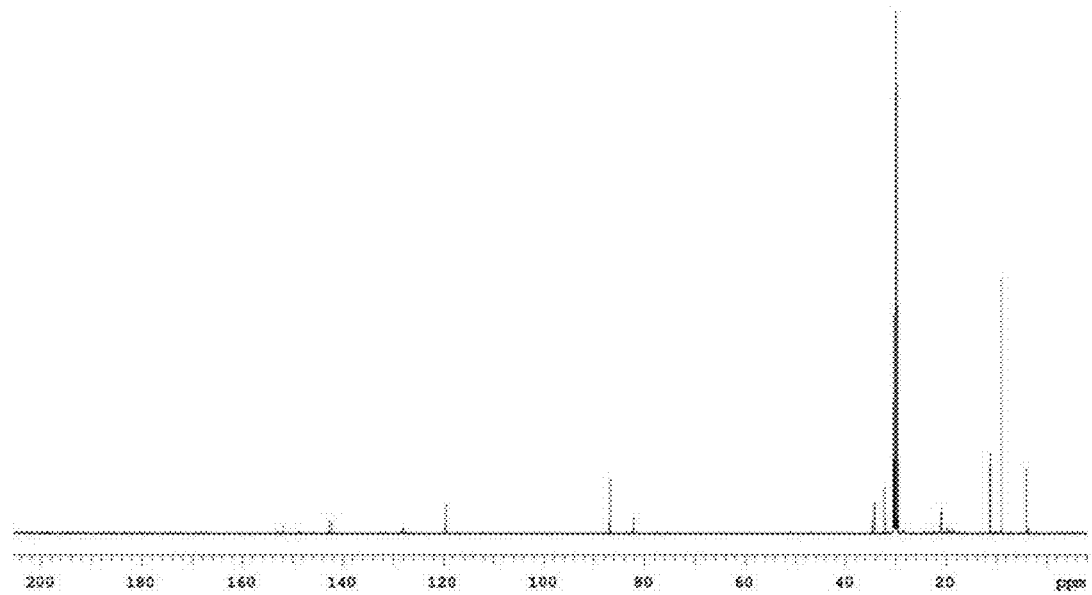
Figure 2D:
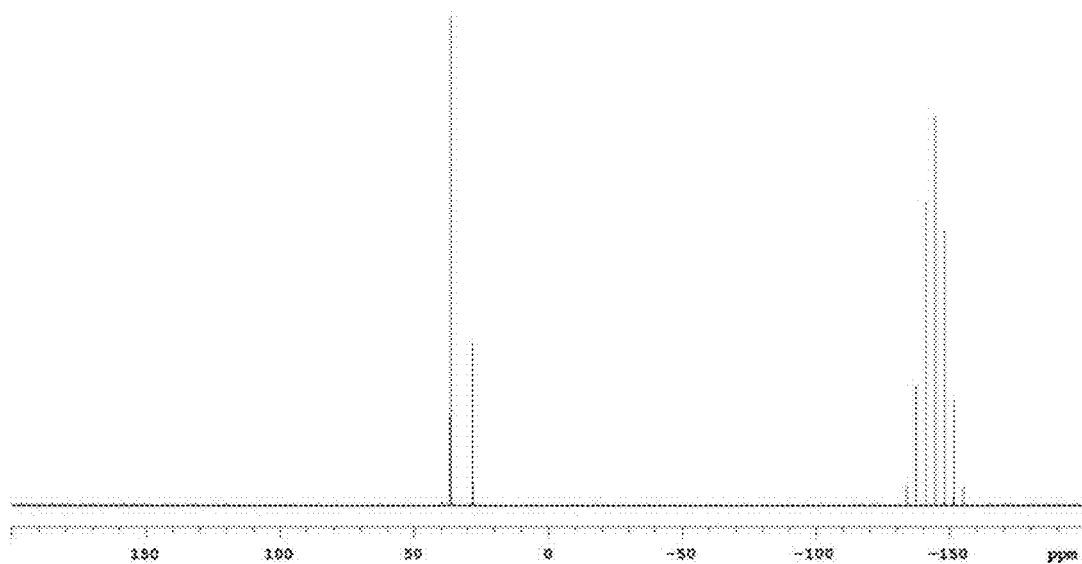

See FIG. 2A for assignments. See FIGS. 2B, 2C, and 2D for NMR spectra.

Rate of Phosphine Binding.

In a glove box to a resealable J. Young tube was added [Cp*Ru(NCCH$_3$)$_3$]PF$_6$ (20.4 mg, 0.0404 mmol) and deoxygenated acetone-$d_6$ (900 μL). To the ruthenium precursor solution was added the requisite phosphine (10.9 mg, 0.0428 mmol) in deoxygenated acetone-$d_6$ (200 μL) and allowed to mix and proceed at room temperature. The reaction was evaluated via $^1$H and $^{31}$P NMR after 15 min, from which it was concluded that formation of 3 was complete.

Figure 3:
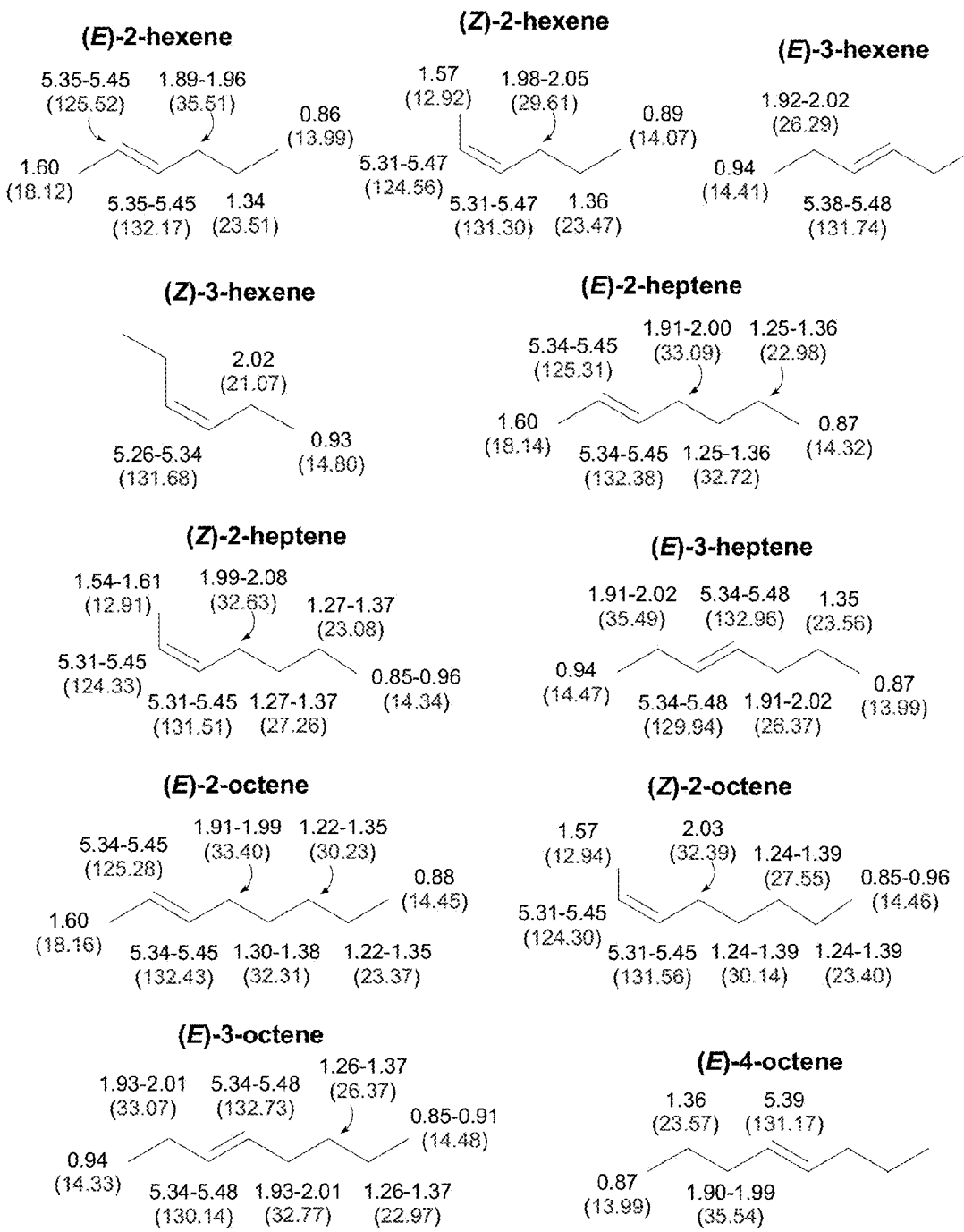
FIG. 3. Spectroscopic data for pure authentic isomeric alkenes ($^1$H 500 MHz, $^{13}$C 125.7 MHz, acetone-$d_6$).

III. Spectroscopic Data for Pure Authentic Isomeric Alkenes ($^1$H 500 MHz, $^{13}$C 125.7 MHz, acetone-$d_6$): see FIG. 3.

IV. Optimization of Conditions.

General Procedure for Catalytic Reactions—Example at 5 Mol %.

In a glovebox, internal standard (Me$_3$Si)$_4$C (small weighed amount, typically 0.5 mg) and substrate (0.50 mmol) were combined with acetone-$d_6$ (~700 μL), and an initial NMR spectrum was acquired. Back in the glovebox, to this mixture was added catalyst 1+3 (19.0 mg, 0.025 mmol; 5 mol %) followed by enough acetone-$d_6$ to reach a final volume of 1.0 mL. The reaction was allowed to proceed at room temperature, however if the mixture was heated in an oil bath, it was heated for the times given. Unless otherwise specified, spectra was acquired at a NMR probe temperature of 30° C.

The value of the integral for the singlet due to the internal standard, (Me$_3$Si)$_4$C, was set equal to 10.00 integral units in each case. Data was acquired using either a Varian 400 MHz or 500 MHz spectrophotometer, with sixteen 15° pulses and 20 sec delays between pulses. Tables show key NMR resonances which could be used to reliably determine yields. Other $^1$H resonances for starting material and product overlapped and were not used. Approximate limit of detection was estimated at 0.2-0.5% for signals well-separated from other signals, in the absence of overlap.

IV-1. Isomerization of 1-Octene Using 5 Mol % Catalyst 1+3 at Room Temperature in Acetone-$d_6$.

Following the general procedure, 1-octene (57.0 mg, 0.508 mmol) and catalyst 1+3 (19.3 mg, 0.0254 mmol, 5.0 mol %) were used. The reaction was conducted at room temperature.

For 1-octene in the mixture: $^1$H NMR (500 MHz, acetone-$d_6$) δ 5.80 (tdd, J=7.0, 10.0, 17.5, 1H), 4.97 (dtd, J=1.5, 2.0, 17.5, 1H), 4.89 (tdd, J=1.0, 2.0, 10.0, 1H), 1.99-2.07 (m, 2H), 1.34-1.42 (m, 2H), 1.24-1.34 (m, 6H), 0.88 ppm (t, J=7.0, 3H). $^{13}$C NMR (125.73 MHz, acetone-$d_6$) δ 139.90, 114.71, 34.61, 32.59, 29.81, 29.66, 23.41, 14.44 ppm.

For the (E)-2-octene in the mixture: $^1$H NMR (500 MHz, acetone-$d_6$) δ 5.34-5.46 (m, 2H), 1.91-1.99 (m, 2H), 1.60 (~d of narrow m, J≈4, 3H), 1.22-1.38 (m, 6H), 0.87 ppm (t, J=7.0, 3H). $^{13}$C NMR (125.73 MHz, acetone-$d_6$) δ 132.42, 125.29, 33.33, 32.23, 30.15, 23.29, 18.11, 14.40 ppm.

TABLE IV-1

Isomerization of 1-octene using 5 mol % catalyst at RT (~23° C.) in acetone-d$_6$.

Measured integrals in arbitrary units relative to internal standard = 10.0 units and (in bold) derived percent yields of products and amount of starting 1-alkene

| Time | 0 h | 26 h | 50 h | 74 h | 97 h | 121 h |
|---|---|---|---|---|---|---|
| (5.80 ppm) | 68.18 | 18.64 | 8.40 | 4.47 | 2.70 | 1.93 |
| (4.97 ppm) | 69.85 | 18.91 | 8.55 | 4.63 | 2.66 | 2.10 |
| (4.89 ppm) | 68.86 | 18.71 | 8.35 | 4.50 | 2.64 | 2.04 |
| units per proton[a] | 68.96 | 18.75 | 8.43 | 4.53 | 2.67 | 2.02 |
| % starting material remaining[b] | 100 | 27.2 | 12.2 | 6.6 | 3.9 | 2.9 |
| (5.34-5.45 ppm) | 0 | 99.38 | 119.32 | 129.70 | 132.82 | 133.27 |
| (1.60 ppm) | 0 | 152.18 | 184.83 | 199.38 | 203.88 | 203.56 |
| units per proton[a] | 0 | 50.31 | 60.83 | 65.82 | 67.34 | 67.37 |
| % yield of product[c] | 0 | 73.0 | 88.2 | 95.4 | 97.7 | 97.7 |

[a]Calculated by taking the average of integrations of the specified resonances.
[b]Calculated by dividing units per proton of starting material at time indicated by units per proton value at hour 0.
[c]Calculated by dividing units per proton of product at time indicated by the units per proton value of starting material at hour 0.

IV-2. Isomerization of 1-Octene Using 4 Mol % Catalyst 1+3 at Room Temperature in Acetone-d$_6$.

Following the general procedure, 1-octene (56.9 mg, 0.507 mmol) and catalyst 1+3 (14.8 mg, 0.021 mmol, 4.1 mol %) were used. The reaction was conducted at room temperature.

TABLE IV-2

Isomerization of 1-octene using 4 mol % catalyst at room temperature in acetone-d$_6$.

Measured integrals in arbitrary units relative to internal standard = 10.0 units and (in bold) derived percent yields of products and amount of starting 1-alkene

| Time | 0 h | 24 h | 48 h | 72 h | 96 h |
|---|---|---|---|---|---|
| (5.80 ppm) | 45.55 | 11.57 | 4.43 | 1.99 | 1.26 |
| (4.97 ppm) | 46.25 | 11.66 | 4.47 | 2.01 | 1.39 |
| (4.89 ppm) | 46.45 | 11.61 | 4.39 | 1.98 | 1.30 |
| units per proton[a] | 46.08 | 11.61 | 4.43 | 1.99 | 1.32 |
| % starting material remaining[b] | 100 | 25.2 | 9.6 | 4.3 | 2.8 |

TABLE IV-2-continued

Isomerization of 1-octene using 4 mol % catalyst at room temperature in acetone-d$_6$.

Measured integrals in arbitrary units relative to internal standard = 10.0 units and (in bold) derived percent yields of products and amount of starting 1-alkene

| Time | 0 h | 24 h | 48 h | 72 h | 96 h |
|---|---|---|---|---|---|
| (5.34-5.46 ppm) | 0 | 67.72 | 84.99 | 87.92 | 88.99 |
| units per proton[a] | 0 | 33.86 | 42.50 | 43.96 | 44.49 |
| % yield of product[c] | 0 | 73.5 | 92.2 | 95.4 | 96.6 |

[a]Calculated by taking the average of integrations of the specified resonances.
[b]Calculated by dividing units per proton of starting material at time indicated by units per proton value at hour 0.
[c]Calculated by dividing units per proton of product at time indicated by the units per proton value of starting material at hour 0.

IV-3. Isomerization of 1-octene Using 4 Mol % Catalyst 1+3 at Room Temperature in CD$_2$Cl$_2$.

Following the general procedure, 1-octene (54.9 mg, 0.489 mmol) and catalyst 1+3 (13.5 mg, 0.019 mmol, 3.9 mol %) were used, but deoxygenated methylene chloride-d$_2$ was used. The reaction was conducted at room temperature.

For 1-octene in the mixture: $^1$H NMR (500 MHz, CD$_2$Cl$_2$) δ 5.82 (tdd, J=6.5, 10.0, 17.0, 1H), 5.00 (dtd, J=1.5, 2.0, 17.0, 1H), 4.93 (tdd, J=1.0, 2.0, 10.0, 1H), 2.06 (td, J=7.0, 7.0, 2H), 1.35-1.45 (m, 2H), 1.24-1.35 (m, 6H), 0.91 ppm (t, J=7.0, 3H). $^{13}$C NMR (125.73 MHz, CD$_2$Cl$_2$) δ 139.99, 114.52, 34.57, 32.51, 29.73, 29.60, 23.38, 14.56 ppm.

For the (E)-2-octene in the mixture: ¹H NMR (500 MHz, CD$_2$Cl$_2$) δ 5.37-5.50 (m, 2H), 1.93-2.01 (m, 2H), 1.64 (~d of narrow m, J≈5, 3H), 1.23-1.41 (m, 6H), 0.90 ppm (t, J=7.0, 3H). ¹³C NMR (125.73 MHz, CD$_2$Cl$_2$) δ 132.35, 125.10, 33.23, 32.16, 30.02, 23.23, 18.26, 14.48 ppm.

TABLE IV-3

Isomerization of 1-octene using 4 mol % catalyst 1 + 3 at room temperature in CD$_2$Cl$_2$.

| | Measured integrals in arbitrary units relative to internal standard = 10.0 units and (in bold) derived percent yields of products and amount of starting 1-alkene | | | | |
|---|---|---|---|---|---|
| Time | 0 h | 24 h | 48 h | 72 h | 311 h |
| 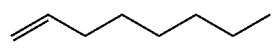 (5.82 ppm) | 46.22 | 32.89 | 23.64 | 18.38 | 3.22 |
| 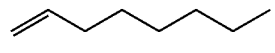 (5.00 ppm) | 47.07 | 32.66 | 23.55 | 17.68 | 2.96 |
| 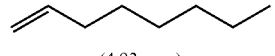 (4.93 ppm) | 46.71 | 32.83 | 23.40 | 17.78 | 2.86 |
| units per proton[a] | 46.67 | 32.79 | 23.53 | 17.95 | 3.01 |
| % starting material remaining[b] | 100 | 70.3 | 50.4 | 38.5 | 6.5 |

TABLE IV-3-continued

Isomerization of 1-octene using 4 mol % catalyst 1 + 3 at room temperature in CD$_2$Cl$_2$.

| | Measured integrals in arbitrary units relative to internal standard = 10.0 units and (in bold) derived percent yields of products and amount of starting 1-alkene | | | | |
|---|---|---|---|---|---|
| Time | 0 h | 24 h | 48 h | 72 h | 311 h |
| 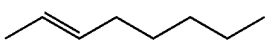 (5.37-5.50 ppm) | 0 | 28.66 | 45.30 | 58.12 | 87.60 |
| units per proton[a] | 0 | 14.33 | 22.65 | 29.06 | 43.80 |
| % yield of product[c] | 0 | 30.7 | 48.5 | 62.3 | 93.9 |

[a]Calculated by taking the average of integrations of the specified resonances.
[b]Calculated by dividing units per proton of starting material at time indicated by units per proton value at hour 0.
[c]Calculated by dividing units per proton of product at time indicated by the units per proton value of starting material at hour 0.

IV-4. Isomerization of 1-Octene Using 4 Mol % Catalyst 1+3 in CD$_3$NO$_2$ at 35° C.

Following the general procedure, 1-octene (57.1 mg, 0.509 mmol) and catalyst 1+3 (15.4 mg, 0.022 mmol, 4.3 mol %) were used, except that deoxygenated nitromethane-d$_3$ was used (with trace amounts of acetone-d$_6$ for solubility reasons). The reaction was conducted at 35° C.

For 1-octene in the mixture: ¹H NMR (500 MHz, CD$_3$NO$_2$) δ 5.82 (tdd, J=6.5, 10.0, 17.0, 1H), 4.98 (dtd, J=1.5, 1.5, 17.0, 1H), 4.90 (tdd, J=1.0, 1.0, 10.0, 1H), 2.04 (~q, J=7.0, 2H), 1.34-1.42 (m, 2H), 1.24-1.34 (m, 6H), 0.88 ppm (t, J=7.0, 3H). ¹³C NMR (125.73 MHz, CD$_3$NO$_2$) δ 140.55, 114.95, 34.95, 32.92, 30.14, 30.01, 23.75, 14.69 ppm.

For the (E)-2-octene in the mixture: ¹H NMR (500 MHz, CD$_3$NO$_2$) δ 5.36-5.48 (m, 2H), 1.92-1.99 (m, 2H), 1.61 (~d of narrow m, J≈5, 3H), 1.22-1.38 (m, 6H), 0.88 ppm (t, J=7.0, 3H). ¹³C NMR (125.73 MHz, CD$_3$NO$_2$) δ 133.02, 125.83, 33.68, 32.62, 30.49, 23.66, 18.32, 14.61 ppm.

TABLE IV-4

Isomerization of 1-octene using 4 mol % catalyst 1 + 3 in CD$_3$NO$_2$ at 35° C.

| | Measured integrals in arbitrary units relative to internal standard = 10.0 units and (in bold) derived percent yields of products and amount of starting 1-alkene | | | | |
|---|---|---|---|---|---|
| Time | 0 h | 1 h | 2 h | 5 h | 24 h |
| 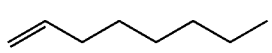 (5.82 ppm) | 62.75 | 48.94 | 34.56 | 20.60 | 2.45 |
| 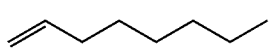 (4.98 ppm) | 63.67 | 49.28 | 34.89 | 21.51 | 2.27 |
| 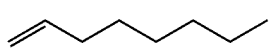 (4.90 ppm) | 63.57 | 48.60 | 35.01 | 20.30 | 2.23 |
| units per proton[a] | 63.33 | 48.94 | 34.82 | 20.80 | 2.32 |
| % starting material remaining[b] | 100 | 77.3 | 55.0 | 32.8 | 3.6 |

TABLE IV-4-continued

Isomerization of 1-octene using 4 mol % catalyst 1 + 3 in CD₃NO₂ at 35° C.

| | Measured integrals in arbitrary units relative to internal standard = 10.0 units and (in bold) derived percent yields of products and amount of starting 1-alkene | | | | |
|---|---|---|---|---|---|
| Time | 0 h | 1 h | 2 h | 5 h | 24 h |
| ⟋⟍⟋⟍⟋ (5.36-5.48 ppm) | 0 | 31.96 | 57.11 | 88.43 | 122.41 |
| units per proton[a] | 0 | 15.98 | 28.56 | 44.22 | 61.21 |
| % yield of product[c] | 0 | 25.2 | 45.1 | 69.8 | 96.6 |

[a]Calculated by taking the average of integrations of the specified resonances.
[b]Calculated by dividing units per proton of starting material at time indicated by units per proton value at hour 0.
[c]Calculated by dividing units per proton of product at time indicated by the units per proton value of starting material at hour 0.

IV-5. Isomerization of 1-Octene Using 4 Mol % Catalyst 1+3 at 35° C. in Acetone-d₆.

Following the general procedure, 1-octene (56.1 mg, 0.500 mmol) and catalyst 1+3 (14.1 mg, 0.020 mmol, 4.0 mol %) were used. The reaction was conducted at 35° C.

TABLE IV-5

Isomerization of 1-octene using 4 mol % catalyst 1 + 3 at 35° C. in acetone-d₆.

| | Measured integrals in arbitrary units relative to internal standard = 10.0 units and (in bold) derived percent yields of products and amount of starting 1-alkene | | | | |
|---|---|---|---|---|---|
| Time | 0 h | 1 h | 2 h | 5 h | 24 h |
| ⟋⟍⟋⟍⟋ (5.80 ppm) | 143.61 | 118.15 | 90.96 | 60.22 | 7.78 |
| ⟋⟍⟋⟍⟋ (4.97 ppm) | 146.23 | 117.32 | 91.90 | 60.89 | 8.39 |
| ⟋⟍⟋⟍⟋ (4.89 ppm) | 148.28 | 117.85 | 92.63 | 60.47 | 7.98 |
| units per proton[a] | 146.04 | 117.77 | 91.83 | 60.53 | 8.05 |
| % starting material remaining[b] | 100 | 80.6 | 62.9 | 41.4 | 5.5 |
| ⟋⟍⟋⟍⟋ (5.34-5.46 ppm) | 0 | 54.71 | 101.77 | 169.60 | 267.15 |
| units per proton[a] | 0 | 27.36 | 50.89 | 84.8 | 133.58 |
| % yield of product[c] | 0 | 18.7 | 34.8 | 58.1 | 91.5 |

[a]Calculated by taking the average of integrations of the specified resonances.
[b]Calculated by dividing units per proton of starting material at time indicated by units per proton value at hour 0.
[c]Calculated by dividing units per proton of product at time indicated by the units per proton value of starting material at hour 0.

IV-6. Isomerization of 1-Octene Using 2 Mol % Catalyst 1+3 at 40° C.

Following the general procedure, 1-octene (56.9 mg, 0.51 mmol) and catalyst 1+3 (6.9 mg, 0.0098 mmol, 1.9 mol %) were used. The reaction was conducted at 40° C.

TABLE IV-6

Isomerization of 1-octene using 2 mol % catalyst 1 + 3 at 40° C. in acetone-$d_6$.

Measured integrals in arbitrary units relative to internal standard = 10.0 units and (in bold) derived percent yields of products and amount of starting 1-alkene

| Time | 0 h | 1 h | 2 h | 5 h | 24 h | 48 h |
|---|---|---|---|---|---|---|
| (5.80 ppm) | 58.34 | 50.52 | 42.33 | 27.46 | 3.38 | 1.54 |
| (4.97 ppm) | 59.10 | 50.99 | 42.56 | 28.29 | 3.32 | 1.61 |
| (4.89 ppm) | 58.80 | 51.00 | 43.11 | 28.20 | 3.22 | 1.49 |
| units per proton[a] | 58.75 | 50.84 | 42.67 | 27.98 | 3.31 | 1.55 |
| % starting material remaining[b] | 100 | 86.5 | 26.2 | 47.6 | 5.6 | 2.6 |
| (5.34-5.46 ppm) | 0 | 15.88 | 30.77 | 61.47 | 109.58 | 112.89 |
| units per proton[a] | 0 | 7.94 | 15.39 | 30.74 | 54.79 | 56.45 |
| % yield of product[c] | 0 | 13.5 | 26.2 | 52.3 | 93.3 | 96.1 |
| (0.94 ppm) | 0 | 0 | 0 | 0 | 0 | 4.35 |
| units per proton[a] | 0 | 0 | 0 | 0 | 0 | 1.45 |
| % yield of product[c] | 0 | 0 | 0 | 0 | 0 | 2.4 |

[a] Calculated by taking the average of integrations of the specified resonances.
[b] Calculated by dividing units per proton of starting material at time indicated by units per proton value at hour 0.
[c] Calculated by dividing units per proton of product at time indicated by the units per proton value of starting material at hour 0.

IV-7. Table 1, Entry 4: Isomerization of 1-Octene Using 1 Mol % Catalyst 1+3 at 40° C. in Acetone-$d_6$.

Following the general procedure, 1-octene (58.5 mg, 0.521 mmol) and catalyst 1+3 (3.9 mg, 0.0055 mmol, 1 mol %) were used. The reaction was conducted at 40° C.

TABLE IV-7

Isomerization of 1-octene using 1 mol % catalyst 1 + 3 at 40° C. in acetone-$d_6$.

Measured integrals in arbitrary units relative to internal standard = 10.0 units and (in bold) derived percent yields of products and amount of starting 1-alkene

| Time | 0 h | 1 h | 2 h | 5 h | 24 h | 48 h |
|---|---|---|---|---|---|---|
| (5.80 ppm) | 36.73 | 32.62 | 29.52 | 22.81 | 6.33 | 2.30 |
| (4.97 ppm) | 36.88 | 33.04 | 30.05 | 23.16 | 6.53 | 2.48 |
| (4.89 ppm) | 36.85 | 32.75 | 30.05 | 23.34 | 6.52 | 2.37 |
| units per proton[a] | 36.82 | 32.80 | 29.87 | 23.10 | 6.46 | 2.38 |
| % starting material | 100 | 89.1 | 81.1 | 62.7 | 17.5 | 6.5 |

TABLE IV-7-continued

Isomerization of 1-octene using 1 mol % catalyst 1 + 3 at 40° C. in acetone-$d_6$.

Measured integrals in arbitrary units relative to internal standard = 10.0 units and (in bold) derived percent yields of products and amount of starting 1-alkene

| Time | 0 h | 1 h | 2 h | 5 h | 24 h | 48 h |
|---|---|---|---|---|---|---|
| remaining[b] (5.34-5.46 ppm) | 0 | 8.98 | 14.34 | 27.85 | 60.90 | 70.17 |
| units per proton[a] | 0 | 4.49 | 7.17 | 13.93 | 30.45 | 35.09 |
| % yield of product[c] | 0 | 12.2 | 19.5 | 37.8 | 82.7 | 95.3 |

[a] Calculated by taking the average of integrations of the specified resonances.
[b] Calculated by dividing units per proton of starting material at time indicated by units per proton value at hour 0.
[c] Calculated by dividing units per proton of product at time indicated by the units per proton value of starting material at hour 0.

V. Detailed Description Table 1: Data for Entries 1, 2, 3, 4, 5, and 6 and Footnote j General Procedure. In a glovebox, internal standard $(Me_3Si)_4C$ (small weighed amount, typically 0.5 mg) and substrate (0.50 mmol) were combined with acetone-$d_6$ (~700 μL), and an initial NMR spectrum was acquired. Back in the glovebox, to this mixture was added catalyst 1+3 followed by enough acetone-$d_6$ to reach a final volume of 1.0 mL. The reaction was heated for the times given at 40° C.

Mixtures were analyzed by $^1$H NMR spectroscopy as in the optimization studies in section III, using internal standard to get product yields. In the case of hydrocarbon alkenes (hexene, heptene, octene, decene), mixtures were also analyzed by GC for product ratios, with comparisons in the case of hexene, heptene and octene with authentic samples of 2-E, 2-Z, and 3-E alkenes.

V-1. Data for Table 1, Entry 1: Procedure for Isomerization of 1-Hexene to E-2-Hexene Using 1 Mol % Catalyst 1+3 at 40° C. in Acetone-$d_6$.

Following the general procedure, 1-hexene (42.0 mg, 0.499 mmol) and catalyst 1+3 (3.5 mg, 0.005 mmol, 1 mol %) were used. Reaction was conducted at 40° C. using an oil bath. At specified time points, $^1$H NMR spectra were obtained and 5 μL of reaction mixture was removed under glovebox atmosphere for GC analysis. For addition of Z-2-hexene and E-3-hexene, a stock solution of 200 μL was prepared with Z-2-hexene (8.7 mg, 0.10 mmol) and E-3-hexene (8.6 mg, 0.10 mmol). 10 μL of this solution was added to the reaction point at 48 h time point.

TABLE V-1a

Yields determined by NMR in isomerization of 1-hexene using 1 mol % catalyst 1 + 3 at 40° C.

Measured integrals in arbitrary units relative to internal standard = 10.0 units and (in bold) derived percent yields of products and amount of starting 1-alkene.

| Time | 0 h | 5h | 22 h | 48 h | 48 h with added Z-2 (1.0%) and E-3 (1.0%)[a] |
|---|---|---|---|---|---|
| (5.79 ppm) | 36.23 | 14.25 | 1.78 | 0.85 | 0.99 |
| (4.85-5.01 ppm) | 73.47 | 29.18 | 3.32 | 1.72 | 1.80 |
| units per proton[b] | 36.57 | 14.48 | 1.70 | 0.86 | 0.93 |
| % starting material remaining[c] | 100 | 39.6 | 4.6 | 2.3 | 2.5 |
| (5.35-5.46 ppm)[d] | — | 44.86 | 70.28 | 70.44 | 72.85 |
| (1.60 ppm) | — | 67.24 | 104.26 | 104.17 | 106.40[e] |
| units per proton[b] | — | 22.42 | 34.91 | 34.92 | 35.85 |
| % of E-2[f] | — | 61.3 | 95.5 | 95.5 | 98.0 |
| (0.94 ppm) | — | — | 2.36 | 4.62 | 6.86 |
| units per proton[b] | — | — | 0.39 | 0.77 | 1.14 |
| % of E-3[f] | — | — | 1.1 | 2.1 | 3.1 |

[a] Spiked with 0.0051 mmol (1.0%) of Z-2 and 0.0051 mmol (1.0%) of E-3.
[b] Calculated by taking the average of integrations of the specified resonances.
[c] Calculated by dividing units per proton of starting material at time indicated by units per proton value at hour 0.
[d] Includes vinylic H for E-2, E-3 and Z-2, but none of these species are present in more than 1% yield until about 24 h, where E-3-hexene is the most prevalent (2.1% at 48 h).
[e] Includes integration for Z-2 methyls (3H).
[f] Calculated by dividing units per proton of product at time indicated by the units per proton value of starting material at hour 0.

TABLE V-1b

Ratios determined by GC in isomerization of 1-hexene using 1 mol % catalyst 1 + 3 at 40° C.

| Time | 5 h | 22 h | 48 h | 48 h with added Z-2 (1.0%) and E-3 (1.0%)[a] |
|---|---|---|---|---|
| (1.83 min) | 39.47 | 2.30 | 4.04 | 2.18 |
| % starting material remaining[b] | 38.2 | 4.8 | 2.2 | 2.5 |
| (1.94 min) | 63.87 | 45.49 | 174.85 | 84.69 |
| (1.91 min) | | | | |

TABLE V-1b-continued

Ratios determined by GC in isomerization of 1-hexene using 1 mol % catalyst 1 + 3 at 40° C.

| Time | 5 h | 22 h | 48 h | 48 h with added Z-2 (1.0%) and E-3 (1.0%)[a] |
|---|---|---|---|---|
| % of E-2 and E-3 | 61.8 | 95.2 | 97.8 | 95.8 |
| 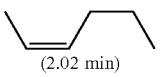 (2.02 min) | 0 | 0 | 0 | 1.55 |
| % of Z-2[b] | 0 | 0 | 0 | 1.8 |
| Total area | 103.34 | 47.79 | 178.89 | 88.42 |

[a]Spiked with 0.0051 mmol (1.0%) of Z-2 and 0.0051 mmol (1.0%) of E-3.
[b]Calculated by taking the ratios of integrations of the specified retention times.

Figure 4:
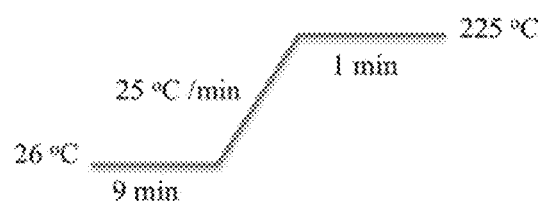
FIG. 4. Gas chromatography temperature program for C6 reaction mixtures (Scheme V-1a).
Figure 5:
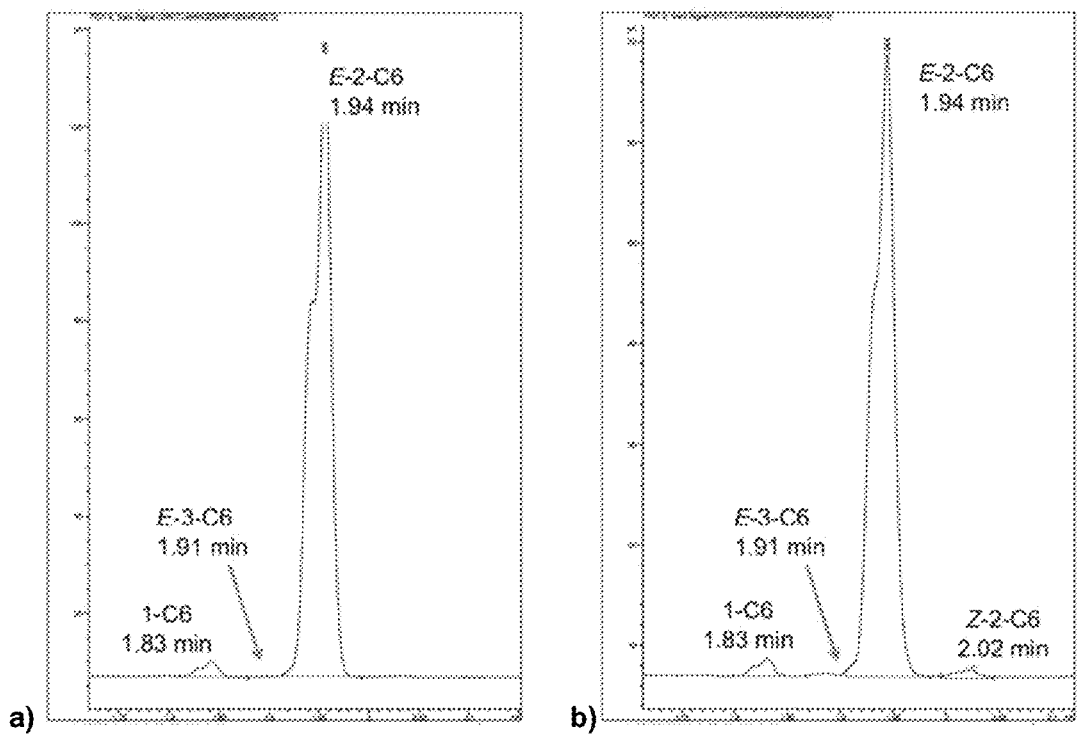
FIG. 5. Gas chromatogram of C6 reaction mixtures a) 48 h. b) 48 h with added of Z-2-hexene (1.0%) and E-3-hexene (1.0%). (Scheme V-1b.)

Scheme V-1a. Gas chromatography temperature program for C6 reaction mixtures. See FIG. 4.
Scheme V-1b. Gas chromatogram of C6 reaction mixtures a) 48 h. b) 48 h with added of Z-2-hexene (1.0%) and E-3-hexene (1.0%). See FIG. 5.
V-2. Data for Table 1, Entry 2. Procedure for Isomerization of 1-Heptene to E-2-Heptene Using 1 Mol % Catalyst 1+3 at 40° C. in Acetone-$d_6$.

Following the general procedure, 1-heptene (49.3 mg, 0.502 mmol) and catalyst 1+3 (3.6 mg, 0.005 mmol, 1 mol %) were used. Reaction was conducted at 40° C. using an oil bath. At specified time points, $^1$H NMR spectra were obtained and 5 μL of reaction mixture was removed under glovebox atmosphere for GC analysis. For addition of Z-2-heptene and E-3-heptene, stock solution of 200 μL was prepared with Z-2-heptene (9.8 mg, 0.10 mmol) and E-3-heptene (9.7 mg, 0.099 mmol). 10 μL of this solution was added to the reaction point at 48 h time point.

TABLE V-2a

Yields determined by NMR in isomerization of 1-heptene using 1 mol % catalyst 1 + 3 at 40° C.

Measured integrals in arbitrary units relative to internal standard = 10.0 units and (in bold) derived percent yields of products and amount of starting 1-alkene.

| Time | 0 h | 5 h | 22 h | 48 h | 48 h with added Z-2 (1.0%) and E-3 (1.0%)[a] |
|---|---|---|---|---|---|
| 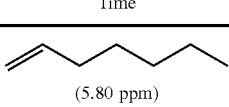 (5.80 ppm) | 62.02 | 27.75 | 3.84 | 1.56 | 1.56 |
| 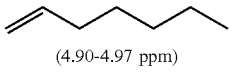 (4.90-4.97 ppm) | 126.71 | 56.37 | 7.50 | 3.11 | 3.25 |
| units per proton[b] | 62.91 | 28.04 | 3.78 | 1.56 | 1.60 |
| % starting material remaining[c] | 100 | 44.6 | 6.0 | 2.5 | 2.6 |
| 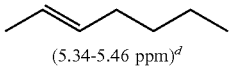 (5.34-5.46 ppm)[d] | — | 67.99 | 117.49 | 120.24 | 123.48 |
| 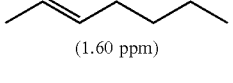 (1.60 ppm) | — | 103.91 | 176.11 | 180.46 | 181.44[e] |
| units per proton[b] | — | 34.38 | 58.72 | 60.14 | 60.98 |
| % of E-2[f] | — | 54.6 | 93.3 | 95.6 | 96.9 |
| 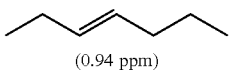 (0.94 ppm) | — | — | 3.07 | 5.52 | 6.73 |
| units per proton[b] | — | — | 1.02 | 1.84 | 2.24 |
| % of E-3[f] | — | — | 1.6 | 2.9 | 3.6 |

[a]Spiked with 0.005 mmol (1.0%) of Z-2 and 0.0050 mmol (1.0%) of E-3.
[b]Calculated by taking the average of integrations of the specified resonances.
[c]Calculated by dividing units per proton of starting material at time indicated by units per proton value at hour 0.
[d]Includes vinylic H for E-2, E-3 and Z-2, but none of these species are present in more than 1% yield until about 24 h, where E-3-heptene is the most prevalent (2.9% at 48 h).
We note that if one uses only the δ 1.60 ppm resonance value at 48 h, one still gets 95.6% yield, which matches GC results (Table V-2b).
[e]Includes integration for Z-2 methyls (3H).
[f]Calculated by dividing units per proton of product at time indicated by the units per proton value of starting material at hour 0.

TABLE V-2b

Ratios determined by GC in isomerization of 1-heptene using 1 mol % catalyst 1 + 3 at 40° C.

| Time | 5 h | 22 h | 48 h | 48 h with added Z-2 (1.0%) and E-3 (1.0%)[a] |
|---|---|---|---|---|
| (2.68 min) | 114.62 | 21.91 | 18.97 | 11.99 |
| % starting material remaining[b] | 45.5 | 6.3 | 2.4 | 2.4 |
| (2.94 min) | 137.46 | 319.89 | 748.84 | 474.43 |
| % of E-2[b] | 54.5 | 92.8 | 95.5 | 93.4 |
| (2.83 min) | 0 | 3.08 | 16.40 | 15.47 |
| % of E-3[b] | 0 | 0.9 | 2.1 | 3.0 |
| 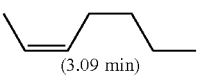 (3.09 min) | 0 | 0 | 0 | 5.93 |
| % of Z-2[b] | 0 | 0 | 0 | 1.2 |
| Total area | 252.08 | 344.88 | 784.21 | 507.82 |

[a]Spiked with 0.005 mmol (1.0%) of Z-2 and 0.005 mmol (1.0%) of E-3.
[b]Calculated by taking the ratios of integrations of the specified retention times.

Figure 6:
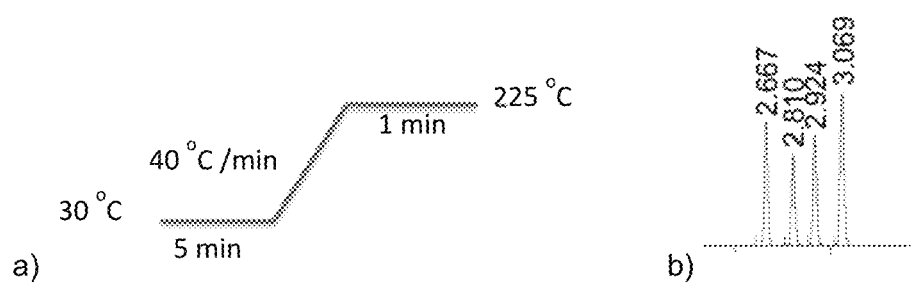
FIG. 6. a) Gas chromatography temperature program for C7 reaction mixtures. b) Gas chromatogram for authentic C7 mixture of 1-heptene, E-3-heptene, E-2-heptene, and Z-2-heptene respectively. (Scheme V-2a.)

Scheme V-2a. a) Gas chromatography temperature program for C7 reaction mixtures. b) Gas chromatogram for authentic C7 mixture of 1-heptene, E-3-heptene, E-2-heptene, and Z-2-heptene respectively. See FIG. 6.

Figure 7:
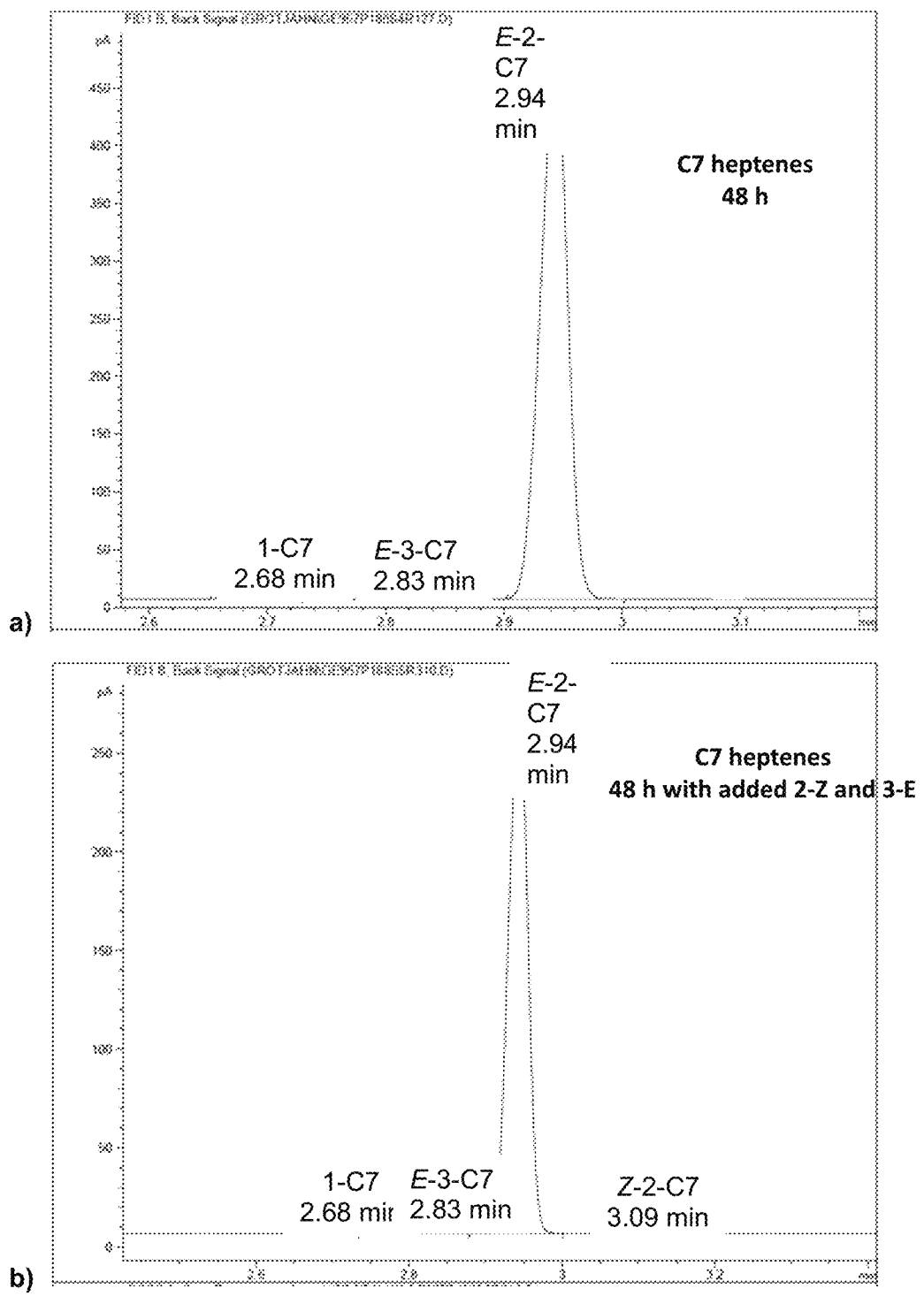
FIG. 7. Gas chromatogram C7 reaction mixtures a) 48 h. b) 48 h with added 0.6 mg Z-2-heptene (1.0%) and 0.8 mg E-3-heptene (1.0%). (Scheme V-2b.)

Scheme V-2b. Gas chromatogram C7 reaction mixtures a) 48 h. b) 48 h with added 0.6 mg Z-2-heptene (1.0%) and 0.8 mg E-3-heptene (1.0%). See FIG. 7.

V-3. Data for Table 1, Entry 3. Procedure for Isomerization of 1-Octene to E-2-Octene Using 1 Mol % Catalyst 1+3 at 40° C. in Acetone-$d_6$.

Following the general procedure, 1-octene (56.0 mg, 0.499 mmol) and catalyst 1+3 (3.5 mg, 0.005 mmol, 1 mol %) were used. Reaction was conducted at 40° C. using an oil bath. At specified time points, $^1$H NMR spectra were obtained and 5 μL of reaction mixture was removed under glovebox atmosphere for GC analysis. For addition of Z-2-octene and E-3-octene, stock solution of 200 μL was prepared with Z-2-octene (11.2 mg, 0.10 mmol) and E-3-octene (11.5 mg, 0.10 mmol). 10 μL of this solution was added to the reaction point at 48 h time point.

TABLE V-3a

Yields determined by NMR in isomerization of 1-octene. Measured integrals in arbitrary units and derived percent starting material remaining and product yields.

Measured integrals in arbitrary units relative to internal standard = 10.0 units and (in bold) derived percent yields of products and amount of starting 1-alkene

| Time | 0 h | 5 h | 22 h | 48 h | 48 h with added Z-2 (1.0%) and E-3 (1.0%)[a] |
|---|---|---|---|---|---|
| (5.80 ppm) | 61.50 | 28.45 | 4.85 | 1.74 | 1.80 |
|  |  |  | (4.52) | (1.83) | (1.61) |
| (4.89-4.97 ppm) | 124.49 | 57.41 | 9.69 | 3.35 | 3.56 |
| units per proton[b] | 62.00 | 28.62 | 3.94 | 1.70 | 1.79 |
| % starting material remaining[c] | 100 | 46.2 | 6.4 | 2.7 | 2.9 |
| (5.42 ppm)[d] | 0 | 66.30 | 114.85 | 119.90 | 121.59 |
| (1.60 ppm) | 0 | 98.94 | 170.46 | 176.87 | 177.53[e] |
| units per proton[b] | 0 | 33.05 | 57.06 | 59.35 | 59.82 |
| % of E-2[f] | 0 | 53.3 | 92.0 | 95.7 | 96.5 |
| 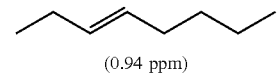 (0.94 ppm) | 0 | 0 | 1.44 | 4.45 | 6.71 |
| units per proton[b] | 0 | 0 | 0.48 | 1.48 | 2.2 |
| % of E-3[f] | 0 | 0 | 0.8 | 2.4 | 3.6 |

[a]Spiked with 0.0050 mmol (1.0%) of Z-2 and 0.0051 mmol (1.0%) of E-3.
[b]Calculated by taking the average of integrations of the specified resonances.
[c]Calculated by dividing units per proton of starting material at time indicated by units per proton value at hour 0.
[d]Includes vinylic H for E-2, E-3 and Z-2, but none of these species are present in more than 1% yield until about 24 h, where E-3-octene is the most prevalent (2.4% at 48 h).
We note that if one uses only the δ 1.60 ppm resonance value at 48 h, one gets 95.1% yield.
[e]Includes integration for Z-2 methyls (3H).
[f]Calculated by dividing units per proton of product at time indicated by the units per proton value of starting material at hour 0.

TABLE V-3b

Ratios determined by GC in isomerization of 1-octene using 1 mol % catalyst 1 + 3 at 40° C.

| Time | 5 h | 22 h | 48 h | 48 h with added Z-2 (1.0%) and E-3 (1.0%)[a] |
|---|---|---|---|---|
| (3.58 min) | 262.60 | 53.90 | 3.27 | 16.03 |
| % starting material remaining[b] | 46.2 | 9.3 | 5.3 | 4.3 |
| (3.98 min) | 305.74 | 521.71 | 56.80 | 338.75 |
| % of E-2[b] | 53.8 | 89.6 | 92.7 | 92.1 |
| (3.81 min) | 0 | 6.55 | 1.22 | 10.09 |
| % of E-3[b] | 0 | 1.1 | 2.0 | 2.7 |
| (4.19 min) | 0 | 0 | 0 | 2.80 |
| % of Z-2[b] | 0 | 0 | 0 | 0.8 |
| Total | 568.34 | 582.16 | 61.29 | 367.67 |

[a]Spiked with 0.0050 mmol (1.0%) of Z-2 and 0.0051 mmol (1.0%) of E-3.
[b]Calculated by taking the ratios of integrations of the specified retention times.

Figure 8:
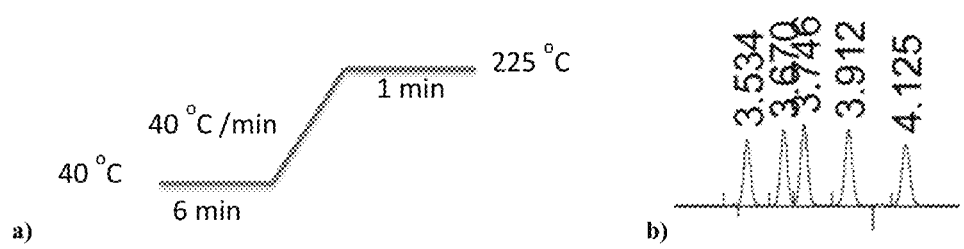
FIG. 8. A) Gas chromatography temperature program for C8 reaction mixtures. B) Gas chromatogram for authentic C8 mixture of 1-octene, E-4-octene, E-3-octene, E-2-octene, and Z-2-octene respectively. (Scheme V-3a.)

Scheme V-3a. A) Gas chromatography temperature program for C8 reaction mixtures. B) Gas chromatogram for authentic C8 mixture of 1-octene, E-4-octene, E-3-octene, E-2-octene, and Z-2-octene respectively. See FIG. 8.

Figure 9:
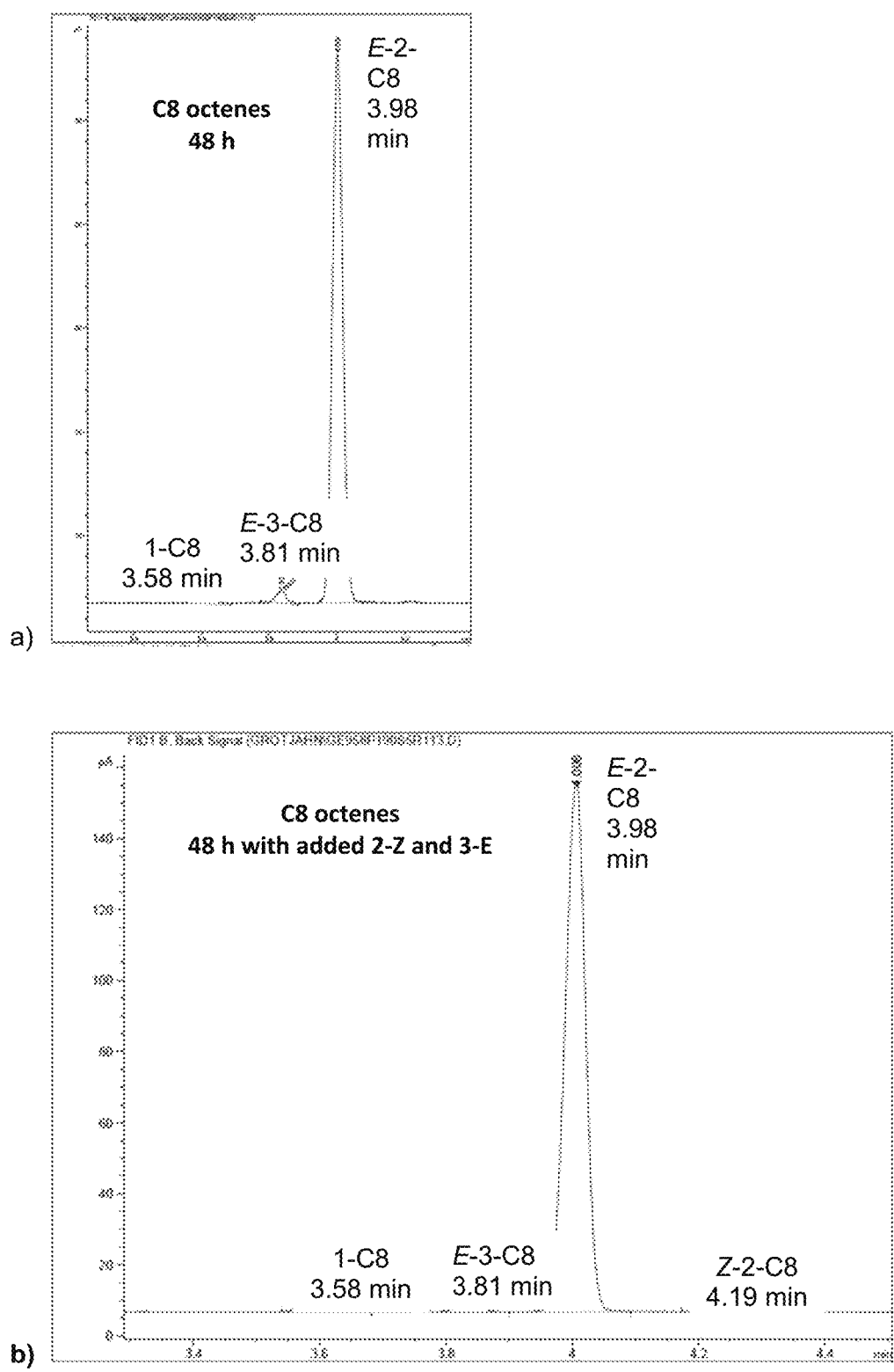
FIG. 9. Gas chromatogram C8 reaction mixtures a) 48 h. b) after addition of Z-2-octene (1.0%) and E-3-heptene (1.0%). (Scheme V-3b.)

Scheme V-3b. Gas chromatogram C8 reaction mixtures a) 48 h. b) after addition of Z-2-octene (1.0%) and E-3-heptene (1.0%). See FIG. 9.

V-4. Data for Table 1, Entry 4: Procedure for Isomerization of 1-Octene to E-2-Octene Using 1 Mol % Catalyst 1+3 in Presence of 1 Mol % CH$_3$CN at 40° C. in Acetone-d$_6$.

Following the general procedure, 1-octene (56.0 mg, 0.499 mmol) and catalyst 1+3 (3.6 mg, 0.005 mmol, 1 mol %) were used. 0.2 μL of a solution prepared with mixing acetone-d$_6$ (200 μL) and acetonitrile (0.8 mg, 0.02 mmol) was added prior to addition of catalyst 1+3. Reaction was conducted at 40° C. using an oil bath. At specified time points, $^1$H NMR spectra were obtained and 5 μL of the reaction mixture was removed under glovebox atmosphere for GC analysis. For addition of Z-2-octene and E-3-octene, a stock solution of 200 μL was prepared with Z-2-octene (11.1 mg, 0.10 mmol) and E-3-octene (11.5 mg, 0.10 mmol). 10 μL of this solution was added to the reaction point at 122 h time point.

TABLE V-4a

Yields determined by NMR in isomerization of 1-octene. Measured integrals in arbitrary units and derived percent starting material remaining and product yields.

Measured integrals in arbitrary units relative to internal standard = 10.0 units and (in bold) derived percent yields of products and amount of starting 1-alkene

| Time | 0 h | 1 h | 5 h | 22 h | 48 h | 72 h | 97 h | 122 h | 122 h with added Z-2 (1.0%) and E-3 (1.0%)[a] |
|---|---|---|---|---|---|---|---|---|---|
| (5.80 ppm) | 68.98 | 63.24 | 44.70 | 14.99 | 4.37 | 2.54 | 1.68 | 1.85 | 1.72 |
| (4.89-4.97 ppm) | 139.93 | 127.74 | 90.72 | 30.47 | 8.63 | 5.03 | 3.91 | 3.55 | 3.42 |
| units per proton[b] | 69.64 | 63.66 | 45.14 | 15.15 | 4.33 | 2.52 | 1.86 | 1.80 | 1.71 |
| % starting material remaining[c] | 100 | 91.4 | 64.8 | 21.8 | 6.2 | 3.6 | 2.7 | 2.6 | 2.5 |
| (5.42 ppm)[d] | 0 | 13.89 | 47.52 | 107.61 | 128.84 | 132.24 | 132.84 | 132.02 | 135.48 |
| (1.6 ppm)[e] | 0 | 21.01 | 71.80 | 162.08 | 190.92 | 195.47 | 196.95 | 194.51 | 197.31 |
| units per proton[b] | 0 | 6.98 | 23.86 | 53.94 | 63.95 | 65.54 | 65.96 | 65.31 | 66.56 |
| % of E-2[f] | 0 | 10.0 | 34.3 | 77.4 | 91.8 | 94.1 | 94.7 | 93.8 | 95.6 |
| (0.94 ppm) | 0 | 0 | 0 | 2.42 | 2.29 | 4.02 | 5.58 | 5.90 | 8.56 |
| units per proton[b] | 0 | 0 | 0 | 0.81 | 0.76 | 1.34 | 1.86 | 1.97 | 2.85 |
| % of E-3[f] | 0 | 0 | 0 | 1.2 | 1.1 | 1.9 | 2.7 | 2.8 | 4.1 |

[a]Spiked with 0.0050 mmol (1.0%) of Z-2 and 0.0051 mmol (1.0%) of E-3.
[b]Calculated by taking the average of integrations of the specified resonances.
[c]Calculated by dividing units per proton of starting material at time indicated by units per proton value at hour 0.
[d]Includes vinylic H for E-2, E-3 and Z-2, but none of these species are present in more than 1% yield until about 24 h, where E-3-octene is the most prevalent (2.8% at 122 h).
We note that if one uses the δ 1.60 ppm resonance value at 122 h, one still gets 93.1% yield, which matches GC results (Table V-4b).
[e]Includes integration for Z-2 methyls (3H).
[f]Calculated by dividing units per proton of product at time indicated by the units per proton value of starting material at hour 0.

TABLE V-4b

Ratios determined by GC in isomerization of 1-octene using 1 mol % catalyst 1 + 3 at 40° C.

| Time | 48 h | 72 h | 97 h | 122 h | 122 h with added Z-2 (1.0%) and E-3 (1.0%)[a] |
|---|---|---|---|---|---|
| (3.58 min) | 26.88 | 62.97 | 44.56 | 41.94 | 39.92 |
| % starting material remaining[b] | 7.5 | 5.3 | 4.5 | 4.3 | 4.2 |
| (3.98 min) | 327.72 | 1110.65 | 916.60 | 903.69 | 858.69 |
| % of E-2[b] | 91.4 | 93.0 | 93.3 | 93.1 | 91.4 |
| (3.81 min) | 3.88 | 19.91 | 20.90 | 24.59 | 31.14 |
| % of E-3[b] | 1.1 | 1.7 | 2.1 | 2.5 | 3.3 |
| (4.19 min) | 0 | 0 | 0 | 4.31 | 10.20 |
| % of Z-2[b] | 0 | 0 | 0 | 0 | 1.1 |
| Total | 358.48 | 1193.53 | 982.06 | 970.22 | 939.95 |

[a]Spiked with 0.0050 mmol (1.0%) of Z-2 and 0.0051 mmol (1.0%) of E-3.
[b]Calculated by taking the ratios of integrations of the specified retention times.

Figure 10:
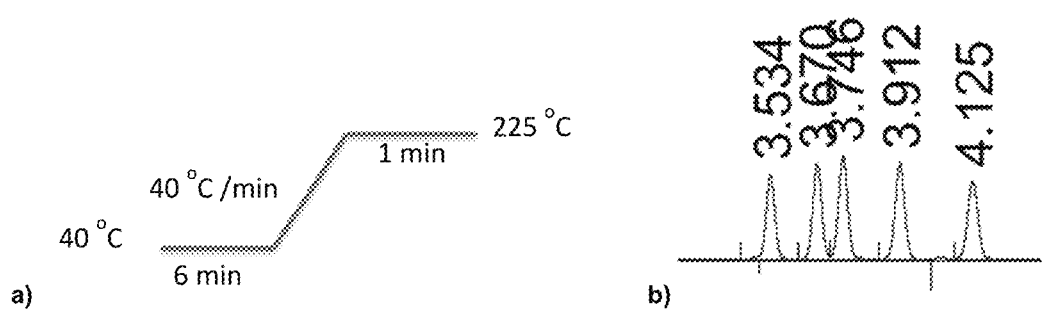
FIG. 10. A) Gas chromatography temperature program for C8 reaction mixtures. B) Gas chromatogram for authentic C8 mixture of 1-octene, E-4-octene, E-3-octene, E-2-octene, and Z-2-octene respectively. (Scheme V-4a.)
Figure 11:
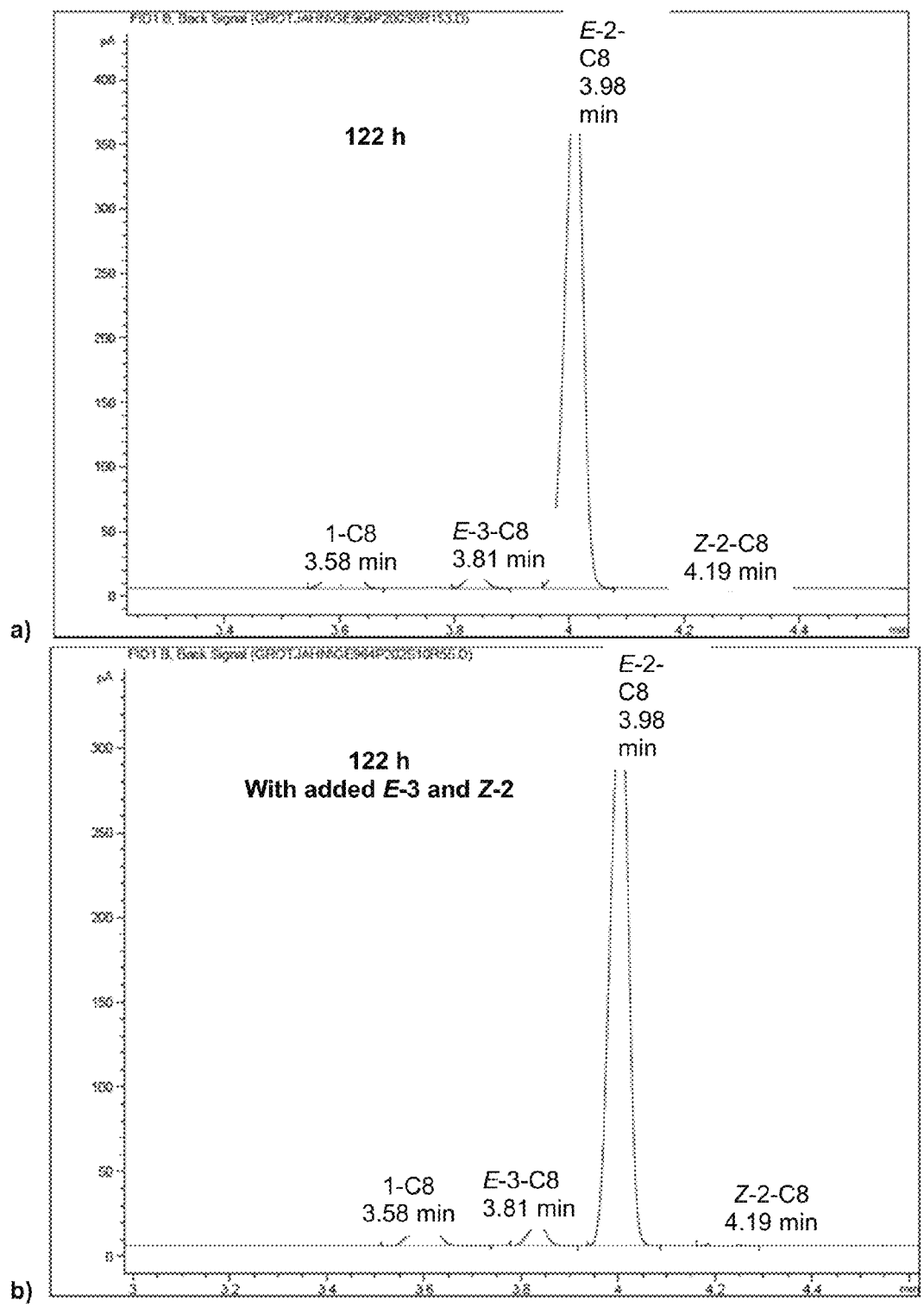
FIG. 11. Gas chromatogram C8 reaction mixtures a) 48 h. b) after addition of Z-2-octene (1.0%) and E-3-heptene (1.0%). (Scheme V-4b.)

Scheme V-4a. A) Gas chromatography temperature program for C8 reaction mixtures. B) Gas chromatogram for authentic C8 mixture of 1-octene, E-4-octene, E-3-octene, E-2-octene, and Z-2-octene respectively. See FIG. 10.
Scheme V-4b. Gas chromatogram C8 reaction mixtures a) 48 h. b) after addition of Z-2-octene (1.0%) and E-3-heptene (1.0%). See FIG. 11.
V-5. Data for Table 1, Entry 5: Procedure for Isomerization of 1-Octene to E-2-Octene Using 1 Mol % Catalyst 3 Prepared In Situ at 40° C. in Acetone-$d_6$.

Using a J. Young NMR tube, a solution of 4-(tert-butyl)-2-(diisopropylphosphino)-1-methyl-1H-imidazole (2.6 mg, 0.01 mmol, 1 mol %) is added to a solution of tris(acetonitrile)pentamethylcyclopentadienylruthenium (II) hexafluorophosphate (5.0 mg, 0.01 mmol, 1 mol %) after acquiring an initial spectrum 1-octene (56.9 mg, 0.507 mmol), was added. Reaction was conducted at 40° C. using an oil bath. At specified time points, $^1$H NMR spectra were obtained and 5 μL of reaction mixture was removed under glovebox atmosphere for GC analysis. For addition of Z-2-octene and E-3-octene, stock solution of 200 μL was prepared with Z-2-octene (11.1 mg, 0.10 mmol) and E-3-octene (11.5 mg, 0.10 mmol). 10 μL of this solution was added to the reaction point at 122 h time point.

TABLE V-5a

Yields determined by NMR in isomerization of 1-octene by catalyst formed in situ. Measured integrals in arbitrary units and derived percent starting material remaining and product yields.

Measured integrals in arbitrary units relative to internal standard = 10.0 units and (in bold) derived percent yields of products and amount of starting 1-alkene

| Time | 0 h | 1 h | 5 h | 22 h | 48 h | 72 h | 97 h | 122 h | 122 h with added Z-2 (1.0%) and E-3 (1.0%)[a] |
|---|---|---|---|---|---|---|---|---|---|
| (5.80 ppm) | | 33.17 | 27.78 | 14.14 | 5.51 | 2.82 | 1.54 | 1.18 | 1.18 |
| (4.89-4.97 ppm) | | 67.11 | 56.28 | 28.41 | 11.00 | 5.78 | 3.13 | 2.40 | 2.34 |
| units per proton[b] | 34.58 | 33.43 | 28.02 | 14.18 | 5.50 | 2.87 | 1.56 | 1.19 | 1.17 |
| % starting material remaining[c] | | 96.7 | 81.0 | 41.0 | 15.9 | 8.3 | 4.5 | 3.4 | 3.4 |
| (5.42 ppm)[d] | 0 | 3.47 | 14.25 | 41.84 | 59.26 | 64.51 | 66.62 | 67.43 | 69.02 |
| (1.60 ppm) | 0 | 5.18 | 21.49 | 62.55 | 88.18 | 96.81 | 98.75 | 100.02 | 100.70 |

TABLE V-5a-continued

Yields determined by NMR in isomerization of 1-octene by catalyst formed in situ.
Measured integrals in arbitrary units and derived percent starting material remaining and product yields.

Measured integrals in arbitrary units relative to internal standard = 10.0 units and (in bold) derived percent yields of products and amount of starting 1-alkene

| Time | 0 h | 1 h | 5 h | 22 h | 48 h | 72 h | 97 h | 122 h | 122 h with added Z-2 (1.0%) and E-3 (1.0%)[a] |
|---|---|---|---|---|---|---|---|---|---|
| units per proton[b] | 0 | 1.73 | 7.15 | 20.88 | 29.49 | 32.26 | 33.07 | 33.49 | 33.94 |
| % of E-2[f] | 0 | 5.0 | 20.7 | 60.4 | 85.3 | 93.3 | 95.6 | 96.8 | 98.2 |
| (E-3 structure, 0.94 ppm) | 0 | 0 | 0 | 0 | 0.97 | 2.01 | 1.82 | 2.34 | 3.39 |
| units per proton[b] | 0 | 0 | 0 | 0 | 0.32 | 0.67 | 0.61 | 0.78 | 1.13 |
| % of E-3[f] | 0 | 0 | 0 | 0 | 0.9 | 1.9 | 1.8 | 2.2 | 3.3 |

[a] Spiked with 0.0050 mmol (1.0%) of Z-2 and 0.0051 mmol (1.0%) of E-3.
[b] Calculated by taking the average of integrations of the specified resonances.
[c] Calculated by dividing units per proton of starting material at time indicated by units per proton value at hour 0.
[d] Includes vinylic H for E-2, E-3 and Z-2, but none of these species are present in more than 1% yield until about 24 h, where E-3-octene is the most prevalent (2.2% at 122 h).
We note that if one uses the δ 1.60 ppm resonance value at 122 h, one still gets 96.4% yield.
[e] Includes integration for Z-2 methyls (3H).
[f] Calculated by dividing units per proton of product at time indicated by the units per proton value of starting material at hour 0.

TABLE V-5b

Ratios determined by GC in isomerization of 1-octene using 1 mol % catalyst at 40° C.

| Time | 48 h | 72 h | 97 h | 122 h | 122 h with added Z-2 (1.0%) and E-3 (1.0%)[a] |
|---|---|---|---|---|---|
| (3.58 min) | 131.68 | 109.34 | 83.94 | 64.09 | 57.21 |
| % starting material remaining[b] | 16.8 | 9.5 | 6.3 | 5.1 | 5.0 |
| (3.98 min) | 644.86 | 1028.44 | 1223.41 | 1171.16 | 1048.01 |
| % of E-2[b] | 82.4 | 89.4 | 92.2 | 93.2 | 91.6 |
| (E-3, 3.81 min) | 5.83 | 12.55 | 18.80 | 21.92 | 30.25 |
| % of E-3[b] | 0.8 | 1.1 | 1.4 | 1.7 | 2.6 |
| (Z-2, 4.19 min) | 0 | 0 | 0 | 0 | 9.15 |
| % of Z-2[b] | 0 | 0 | 0 | 0 | 0.8 |
| Total | 782.37 | 1150.33 | 1326.15 | 1257.17 | 1144.62 |

[a] Spiked with 0.0050 mmol (1.0%) of Z-2 and 0.0051 mmol (1.0%) of E-3.
[b] Calculated by taking the ratios of integrations of the specified retention times.

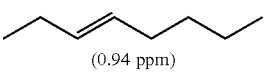

Figure 12:
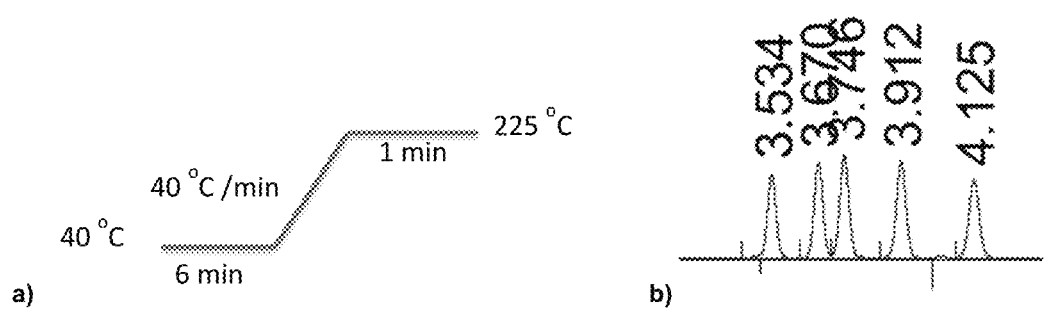
FIG. 12. a) Gas chromatography temperature program for C8 reaction mixtures. b) Gas chromatogram for authentic C8 mixture of 1-octene, E-4-octene, E-3-octene, E-2-octene, and Z-2-octene respectively. (Scheme V-5a.)

Scheme V-5a. a) Gas chromatography temperature program for C8 reaction mixtures. b) Gas chromatogram for authentic C8 mixture of 1-octene, E-4-octene, E-3-octene, E-2-octene, and Z-2-octene respectively. See FIG. 12.

Figure 13:
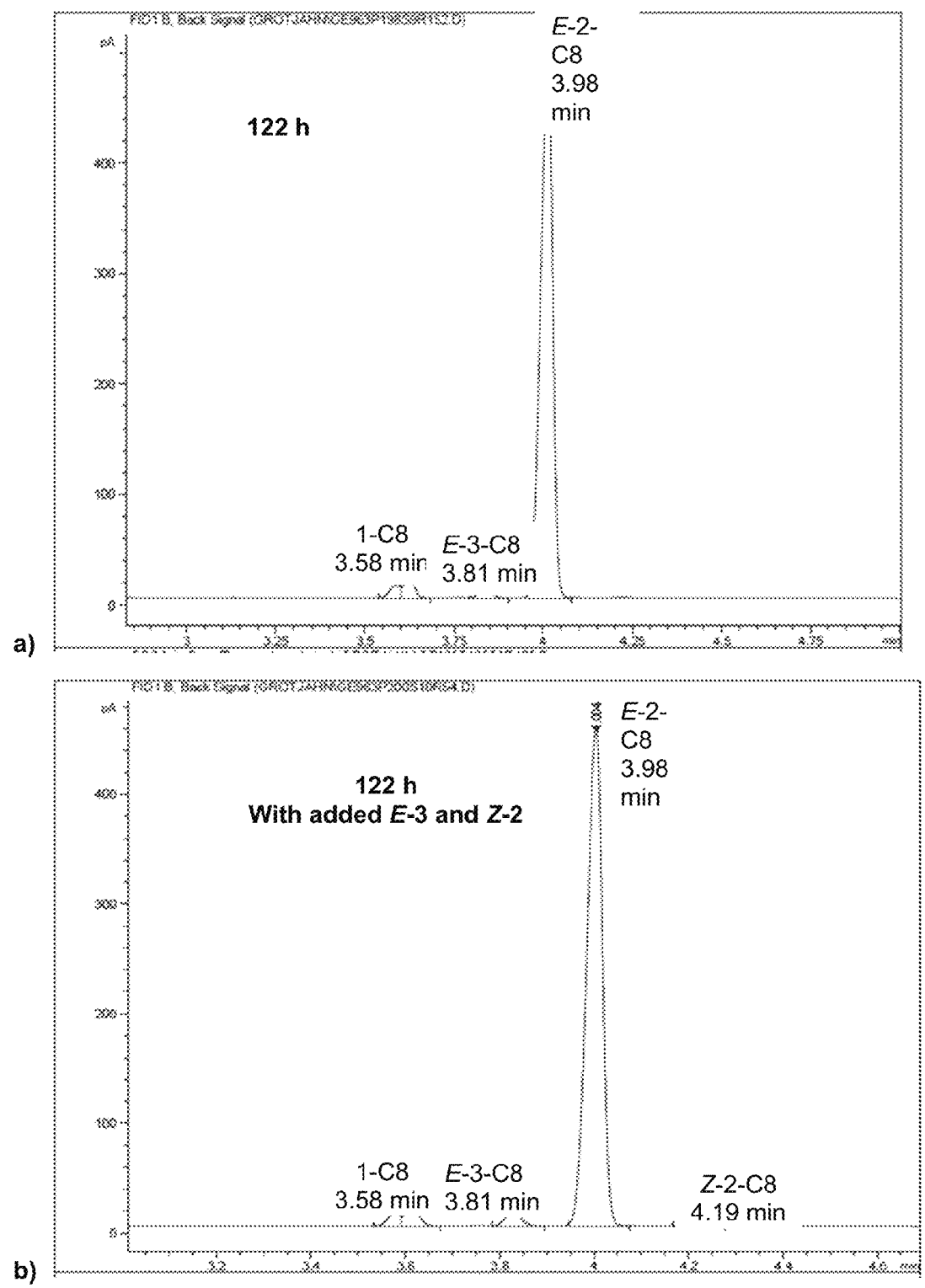
FIG. 13. Gas chromatogram C8 reaction mixtures a) 48 h. b) after addition of Z-2-octene (1.0%) and E-3-heptene (1.0%). (Scheme V-5b.)

Scheme V-5b. Gas chromatogram C8 reaction mixtures a) 48 h. b) after addition of Z-2-octene (1.0%) and E-3-heptene (1.0%). See FIG. 13.

V-6. Data for Table 1, Entry 6. Procedure for Isomerization of 1-Decene to E-2-Decene Using 2 Mol % Catalyst 1+3 at 40° C. in Acetone-$d_6$.

Following the general procedure, 1-decene (72.0 mg, 0.513 mmol) and catalyst 1+3 (7.1 mg, 0.010 mmol, 2 mol %) were used. Reaction was conducted at 40° C. using an oil bath. At specified time points, $^1$H NMR spectra were obtained and 5 μL of reaction mixture was removed under glovebox atmosphere for GC analysis.

TABLE V-6a

Yields determined by NMR in isomerization of 1-decene using 1 mol % catalyst at 40° C.

|  | Measured integrals in arbitrary units relative to internal standard = 10.0 units and (in bold) derived percent yields of products and amount of starting 1-alkene | | | |
|---|---|---|---|---|
| Time | 0 h | 5 h | 21 h | 48 h |
| 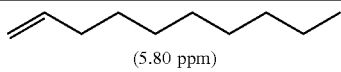 (5.80 ppm) | 66.84 | 30.40 | 5.18 | 1.87 |
| 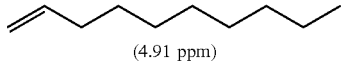 (4.91 ppm) | 136.67 | 60.95 | 10.46 | 3.41 |
| units per proton[a] | 67.84 | 30.45 | 5.21 | 1.76 |
| % starting material remaining[b] | 100 | 44.9 | 7.7 | 2.6 |
| 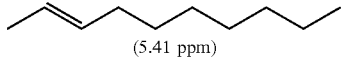 (5.41 ppm) | 0 | 72.13 | 123.18 | 129.93 |
| units per proton[a] | 0 | 36.06 | 61.59 | 65.0 |
| % yield of product[c] | 0 | 53.2 | 90.8 | 95.8 |
| 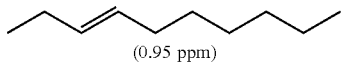 (0.95 ppm) | 0 | 0 | 2.66 | 4.47 |
| units per proton[a] | 0 | 0 | 0.89 | 1.49 |
| % of E-3[c] | 0 | 0 | 1.3 | 2.2 |

[a]Calculated by taking the average of integrations of the specified resonances.
[b]Calculated by dividing units per proton of starting material at time indicated by units per proton value at hour 0.
[c]Calculated by dividing units per proton of product at time indicated by the units per proton value of starting material at hour 0.

TABLE V-6b

Ratios determined by GC in isomerization of 1-decene using 1 mol % catalyst 1 + 3 at 40° C.

| Time | 5 h | 21 h | 48 h |
|---|---|---|---|
| 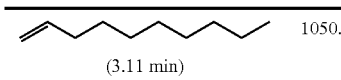 (3.11 min) | 1050.30 | 258.99 | 81.44 |
| % starting material remaining[a] | 46.4 | 7.4 | 2.6 |
| 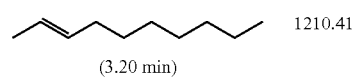 (3.20 min) | 1210.41 | 3177.41 | 2499.31 |
| % yield of E-2[a] | 53.5 | 91.3 | 95.4 |
| 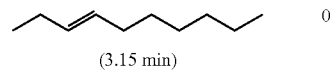 (3.15 min) | 0 | 0 | 63.13 |
| % of E-3[a] | 0 | 0 | 2.0 |

Figure 14:
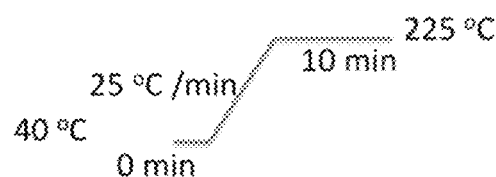
FIG. 14. Gas chromatography temperature program for C10 reaction mixtures (Scheme V-6a).

[a]Calculated by taking the ratios of integrations of the specified retention times Scheme V-6a. Gas chromatography temperature program for C10 reaction mixtures. See FIG. 14.

Figure 15:
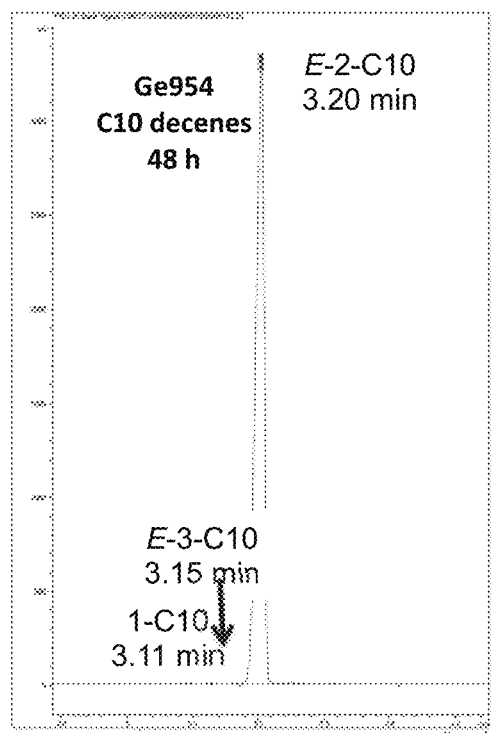
FIG. 15. Gas chromatogram C10 reaction mixtures at 48 h (Scheme V-6b).

Scheme V-6b. Gas chromatogram C10 reaction mixtures at 48 h. See FIG. 15.

V-7. Detailed Description Table 1, Footnote j for Entry 6: Isomerization of 1-Decene Using 5 Mol % Catalyst at Room Temperature.

1-decene (72.9 mg, 0.520 mmol) and catalyst 1+3 (19.9 mg, 0.0262 mmol, 5.0 mol %) were used. The reaction was conducted at room temperature.

For 1-decene in the mixture: $^1$H NMR (500 MHz, acetone-$d_6$) δ 5.80 (tdd, J=7.0, 10.5, 17.0, 1H), 4.97 (dtd, J=1.5, 2.0, 17.0, 1H), 4.89 (tdd, J=1.5, 2.0, 10.5, 1H), 1.99-2.07 (m, 2H), 1.35-1.43 (m, 2H), 1.22-1.35 (m, 10H), 0.88 ppm (t, J=7.0, 3H). $^{13}$C NMR (125.73 MHz, acetone-$d_6$) δ 139.88, 114.71, 34.63, 32.77, 30.35, 30.18, 30.02, 29.87, 23.46, 14.48 ppm.

For the (E)-2-decene in the mixture: $^1$H NMR (500 MHz, acetone-$d_6$) δ 5.35-5.45 (m, 2H), 1.92-2.00 (m, 2H), 1.60 (~d of narrow m, J≈5, 3H), 1.22-1.38 (m, 10H), 0.88 ppm (t, J=7.0, 3H). $^{13}$C NMR (125.73 MHz, acetone-$d_6$) δ 132.42, 125.28, 33.38, 32.73, 30.50, 30.04, 29.98, 23.43, 18.13, 14.45 ppm.

TABLE V-7a

Isomerization of 1-decene using 5 mol % catalyst 1 + 3 at room temperature.

| Time | 0 h | 26 h | 50 h | 74 h | 97 h | 121 h |
|---|---|---|---|---|---|---|
|  (5.80 ppm) | 78.01 | 26.88 | 13.63 | 7.77 | 4.73 | 3.39 |
| 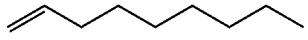 (4.97 ppm) | 78.32 | 27.28 | 13.77 | 7.99 | 4.40 | 3.47 |
| 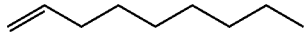 (4.89 ppm) | 78.85 | 26.79 | 13.62 | 7.84 | 4.41 | 3.36 |
| units per proton[a] | 78.39 | 26.98 | 13.67 | 7.87 | 4.51 | 3.41 |
| % starting material remaining[b] | 100 | 34.4 | 17.4 | 10.0 | 5.7 | 4.3 |
| 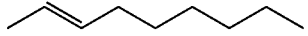 (5.35-5.45 ppm) | 0 | 103.27 | 129.30 | 142.53 | 145.91 | 150.29 |
| 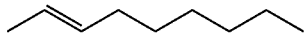 (1.60 ppm) | 0 | 163.29 | 200.41 | 215.49 | 219.71 | 227.84 |
| units per proton[a] | 0 | 53.31 | 65.94 | 71.60 | 73.12 | 75.63 |
| % yield of product[c] | 0 | 68.0 | 84.1 | 91.3 | 93.3 | 96.5 |

[a]Calculated by taking the average of integrations of the specified resonances.
[b]Calculated by dividing units per proton of starting material at time indicated by units per proton value at hour 0.
[c]Calculated by dividing units per proton of product at time indicated by the units per proton value of starting material at hour 0.

TABLE V-7a

COSY, HSQC, and HMBC assignments.

```
5.33-5.48    1.92-2.00
(125.28)     (33.38)
                  (30.04)  (23.43)
1.60
(18.13)   5.33-5.48   1.22-1.38     0.88
          (132.40)   (30.50)(29.98) (14.48)
```

COSY

| 5.33-5.48 | ↔ | 1.92-2.00 |
| | ↔ | 1.60 |
| 1.92-2.00 | ↔ | 1.60 |
| | ↔ | 1.22-1.38 |
| 1.22-1.38 | ↔ | 0.88 |

HSQC

| 5.33-5.48 | ↔ | (132.42) |
| | ↔ | (125.28) |
| 1.92-2.00 | ↔ | (33.38) |
| 1.60 | ↔ | (18.13) |
| 1.22-1.38 | ↔ | (32.73) |
| | ↔ | (30.50) |
| | ↔ | (30.04) |
| | ↔ | (29.98) |
| | ↔ | (23.43) |
| 0.88 | ↔ | (14.48) |

TABLE V-7a-continued

COSY, HSQC, and HMBC assignments.

HMBC

| 5.33-5.48 | ↔ | (33.38) |
| | ↔ | (18.13) |
| 1.92-2.00 | ↔ | (132.40) |
| | ↔ | (125.26) |
| | ↔ | (30.50) |
| 1.60 | ↔ | (132.40) |
| | ↔ | (125.26) |
| 1.22-1.38 | ↔ | (132.40) |
| | ↔ | (32.73) |
| | ↔ | (30.50) |
| | ↔ | (30.04) |
| | ↔ | (29.98) |
| 0.88 | ↔ | (32.73) |
| | ↔ | (23.43) |

VI. Table 1: Data for Control Experiments Showing Differences Between Cp*Ru Catalyst 1+3 and CpRu Catalyst 2a VI-1a. Data for Table 1, Entry I.a. Isomerization of 1-Hexene with CpRu Catalyst 2a.

Following the general procedure, 1-hexene (44.3 mg, 0.526 mmol) and catalyst 2a (2.2 mg, 0.0036 mmol, 0.7 mol %) were used. The reaction was conducted at room temperature.

For 1-hexene in the mixture: $^1$H NMR (500 MHz, acetone-d$_6$) δ 5.79 (tdd, J=5.5, 10.5, 17.5, 1H), 4.85-5.01 (m, 2H), 2.04 (td, J=6.5, 7.0, 2H), 1.27-1.40 (m, 4H), 0.89 ppm (t, J=7.5, 3H). $^{13}$C NMR (125.73 MHz, acetone-d$_6$) δ 139.88, 114.71, 34.28, 32.04, 22.92, 14.26 ppm.

For the (E)-2-hexene in the mixture: $^1$H NMR (500 MHz, acetone-d$_6$) δ 5.35-5.46 (m, 2H), 1.89-1.96 (m, 2H), 1.60 (dd, J=1.0, 3.5, 3H), 1.34 (qt, J=7.5, 7.5, 2H), 0.87 ppm (t, J=7.5, 3H). $^{13}$C NMR (125.73 MHz, acetone-d$_6$) δ 132.15, 125.51, 35.48, 23.48, 18.10, 13.97 ppm.

TABLE VI-1a

Isomerization of 1-hexene using 0.7 mol % CpRu catalyst 2a at room temperature.

Measured integrals in arbitrary units relative to internal standard = 10.0 units and (in bold) derived percent yields of products and amount of starting 1-alkene

| Time | 0 h | 2 h | 146 h | 336 h |
|---|---|---|---|---|
| 1-hexene CH=CH$_2$ (5.79 ppm) | 60.64 | 0.78 | 0.52 | trace |
| 1-hexene =CH$_2$ (4.85-5.01 ppm) | 121.06 | 2.12 | 1.66 | trace |
| units per proton[a] | 60.57 | 0.97 | 0.72 | trace |
| % starting material remaining[b] | 100 | 1.6 | 1.2 | trace |
| (E)-2-hexene (1.60 ppm) | 0 | 137.24 | 120.14 | 110.36 |
| units per proton[a] | 0 | 45.75 | 40.05 | 36.79 |
| % yield of product[c] | 0 | 75.5 | 66.1 | 60.7 |
| (Z)-2-hexene (1.57 ppm) | 0 | 0 | 18.06 | 26.47 |
| units per proton[a] | 0 | 0 | 6.02 | 8.82 |
| % yield of product[c] | 0 | 0 | 9.9 | 14.6 |
| 3-hexene (0.94 ppm) | 0 | 87.83 | 85.79 | 82.82 |
| Units per proton[a] | 0 | 14.68 | 14.30 | 13.80 |
| % yield of isomer[c] | 0 | 24.2 | 23.6 | 22.8 |

[a]Calculated by taking the average of integrations of the specified resonances.
[b]Calculated by dividing units per proton of starting material at time indicated by units per proton value at hour 0.
[c]Calculated by dividing units per proton of product at time indicated by the units per proton value of starting material at hour 0.

VI-2a. Data for Table 1, Entry 2a. Isomerization of 1-Heptene with CpRu Catalyst 2a.

Following the general procedure, 1-heptene (49.4 mg, 0.503 mmol) and catalyst 2a (3.0 mg, 0.0050 mmol, 1 mol %) were used. Reaction was conducted at ambient temperature. At specified time points, $^1$H NMR spectra were obtained.

TABLE VI-2a

Yields determined by NMR in isomerization of 1-heptene using 1 mol % CpRu catalyst 2a at ambient temperature.

Measured integrals in arbitrary units relative to internal standard = 10.0 units and (in bold) derived percent yields of products and amount of starting 1-alkene

| Time | 0 | 10 min | 4 h |
|---|---|---|---|
| 1-heptene (5.80 ppm) | 83.29 | 1.08 | 0.86 |

TABLE VI-2a-continued

Yields determined by NMR in isomerization of 1-heptene using 1 mol % CpRu catalyst 2a at ambient temperature.

| | Measured integrals in arbitrary units relative to internal standard = 10.0 units and (in bold) derived percent yields of products and amount of starting 1-alkene | | |
|---|---|---|---|
| Time | 0 | 10 min | 4 h |
| 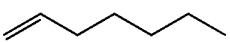 (4.90-4.97 ppm) | 169.58 | 1.86 | 1.44 |
| units per proton[a] | 84.29 | 0.89 | 0.77 |
| % starting material remaining[b] | 100 | 1.2 | 0.9 |
| 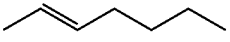 (5.34-5.46 ppm)[c] | 0 | 166.58 | 164.58 |
| 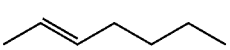 (1.60 ppm) | 0 | 151.43 | 131.19 |
| units per proton[a] | 0 | 50.48 | 43.73 |
| % of E-2[f] | 0 | 59.9 | 51.9 |
| 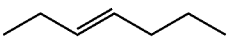 (0.94 ppm) | 0 | 96.74 | 114.19 |
| units per proton[a] | 0 | 32.25 | 38.06 |
| % of E-3[d] | 0 | 38.3 | 45.2 |

[a]Calculated by taking the average of integrations of the specified resonances.
[b]Calculated by dividing units per proton of starting material at time indicated by units per proton value at hour 0.
[c]Includes vinylic H for E-2, E-3 and Z-2, not used in determination of percentages.
[d]Calculated by dividing units per proton of product at time indicated by the units per proton value of starting material at hour 0.

VII. Table 2: Data
VII-1. Data for Detailed Description Table 2, Entry 1: Isomerization of pent-4-en-1-ol at 40° C.

Following the general procedure, pent-4-en-1-ol (44.2 mg, 0.513 mmol) and catalyst 1+3 (3.6 mg, 0.0052 mmol, 1 mol %) were used. The reaction was conducted at 40° C.

For the pent-4-en-1-ol in the mixture: $^1$H NMR (500 MHz, acetone-$d_6$) δ 5.84 (tdd, J=7.5, 10.0, 17.0, 1H), 4.85-5.08 (m, 2H), 3.51-3.59 (m, 2H), 3.47-3.53 (m, 1H), 2.07-2.15 (m, 2H), 1.58 ppm (td, J=7.0, 7.0, 2H).

For the (E)-pent-3-en-1-ol in the mixture: $^1$H NMR (500 MHz, acetone-$d_6$) δ 5.39-5.52 (m, 2H), 3.47-3.45 (m, 2H), 3.43 (t, J=5.0, 1H), 2.13-2.21 (m, 2H), 1.62 ppm (dd, J=1.0, 5.0, 3H). $^{13}$C NMR (125.73 MHz, acetone-$d_6$) δ 129.12, 127.17, 62.67, 37.21, 18.21 ppm.

TABLE VII-1

Isomerization of 4-penten-1-ol using 1 mol % catalyst 1 + 3 at 40° C.

| | Measured integrals in arbitrary units relative to internal standard = 10.0 units and (in bold) derived percent yields of products and amount of starting 1-alkene | | | | | |
|---|---|---|---|---|---|---|
| Time | 0 h | 1 h | 2 h | 5 h | 24h | 46 h |
| 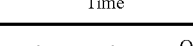 (5.84 ppm) | 63.26 | 43.21 | 29.64 | 10.69 | 1.52 | 1.67 |
| 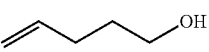 (4.85-5.08 ppm) | 129.59 | 90.35 | 60.95 | 21.92 | 3.60 | 3.25 |
| units per proton[a] | 64.28 | 44.52 | 30.20 | 10.87 | 1.71 | 1.64 |
| % starting material remaining[b] | 100 | 69.3 | 47.0 | 16.9 | 2.7 | 2.5 |

TABLE VII-1-continued

Isomerization of 4-penten-1-ol using 1 mol % catalyst 1 + 3 at 40° C.

| | Measured integrals in arbitrary units relative to internal standard = 10.0 units and (in bold) derived percent yields of products and amount of starting 1-alkene | | | | | |
|---|---|---|---|---|---|---|
| Time | 0 h | 1 h | 2 h | 5 h | 24h | 46 h |
| 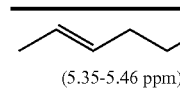 (5.35-5.46 ppm) | 0 | 38.11 | 65.39 | 104.99 | 121.34 | 120.05 |
| units per proton[a] | 0 | 19.06 | 32.70 | 52.50 | 60.67 | 60.25 |
| % yield of product[c] | 0 | 29.6 | 50.9 | 81.7 | 94.4 | 93.7 |
| 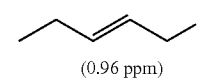 (0.96 ppm) | 0 | 0 | 0 | 0 | 0 | 2.34 |
| units per proton[a] | 0 | 0 | 0 | 0 | 0 | 0.78 |
| % yield of isomer[c] | 0 | 0 | 0 | 0 | 0 | 1.2 |
| 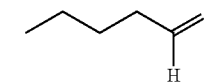 (9.72 ppm) | 0 | 0 | 0 | 0 | 0 | 0.43 |
| units per proton[a] | 0 | 0 | 0 | 0 | 0 | 0.43 |
| % yield of aldehyde[c] | 0 | 0 | 0 | 0 | 0 | 0.7 |

[a]Calculated by taking the average of integrations of the specified resonances.
[b]Calculated by dividing units per proton of starting material at time indicated by units per proton value at hour 0.
[c]Calculated by dividing units per proton of product at time indicated by the units per proton value of starting material at hour 0.

VII-2. Data for Detailed Description Table 2, Entry 2a: Isomerization of pent-4-en-1-ol tert-butyldimethylsilyl ether at 40° C.

Following the general procedure, pent-4-en-1-ol tert-butyldimethylsilyl ether (97.5 mg, 0.487 mmol) and catalyst 1+3 (3.7 mg, 0.0053 mmol, 1 mol %) were used. The reaction was conducted at 40° C.

For the pent-4-en-1-ol tert-butyldimethylsilyl ether in the mixture: $^1$H NMR (500 MHz, acetone-$d_6$) δ 5.82 (tdd, J=6.5, 10.5, 17.5, 1H), 4.99 (tdd, J=2.0, 2.0, 17.5, 1H), 4.92 (tdd, J=1.0, 2.0, 10.5, 1H), 3.63 (t, J=6.5, 2H), 2.07-2.15 (m, 2H), 1.59 (td, J=6.5, 6.5, 2H), 0.90 (s, 9H), 0.046 ppm (s, 6H).

For the (E)-pent-3-en-1-ol tert-butyldimethylsilyl ether in the mixture: $^1$H NMR (500 MHz, acetone-$d_6$) δ 5.38-5.52 (m, 2H), 3.61 (t, J=6.5, 2H), 2.13-2.20 (m, 2H), 1.59-1.65 (md, J=4.5, 3H), 0.89 (s, 9H), 0.04 ppm (s, 6H). $^{13}$C NMR (125.73 MHz, acetone-$d_6$) δ 128.85, 127.32, 63.90, 37.15, 26.39, 26.20, 18.92, 18.25, −4.99 ppm.

TABLE VII-2a

Isomerization of pent-4-en-1-ol tert-butyldimethylsilyl ether at 40° C.

| | Measured integrals in arbitrary units relative to internal standard = 10.0 units and (in bold) derived percent yields of products and amount of starting 1-alkene | | | | | | |
|---|---|---|---|---|---|---|---|
| Time | 0 h | 1 h | 2 h | 5 h | 23 h | 45 h | 48 h |
| 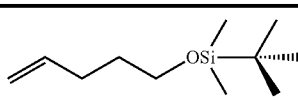 (5.82 ppm) | 24.42 | 21.15 | 18.38 | 13.21 | 3.56 | 1.34 | 1.16 |
| 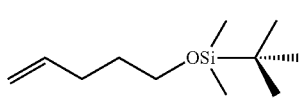 (4.99 ppm) | 24.66 | 21.17 | 18.25 | 13.29 | 3.51 | 1.26 | 1.18 |
| 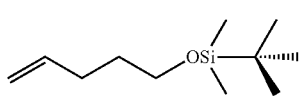 (4.92 ppm) | 24.79 | 21.32 | 18.42 | 13.40 | 3.49 | 1.23 | 1.14 |

TABLE VII-2a-continued

Isomerization of pent-4-en-1-ol tert-butyldimethylsilyl ether at 40° C.

Measured integrals in arbitrary units relative to internal standard = 10.0 units and (in bold) derived percent yields of products and amount of starting 1-alkene

| Time | 0 h | 1 h | 2 h | 5 h | 23 h | 45 h | 48 h |
|---|---|---|---|---|---|---|---|
| units per proton[a] | 24.62 | 21.21 | 18.35 | 13.30 | 3.52 | 1.28 | 1.16 |
| % starting material remaining[b] | 100 | 86.2 | 74.5 | 54.0 | 14.3 | 5.2 | 4.7 |
| (5.38–5.52 ppm) | 0 | 6.97 | 12.16 | 22.84 | 41.95 | 46.07 | 46.83 |
| units per proton[a] | 0 | 3.49 | 6.08 | 11.42 | 20.98 | 23.04 | 23.42 |
| % yield of product[c] | 0 | 14.2 | 24.7 | 46.4 | 85.2 | 93.6 | 95.1 |
| (4.12 ppm) | 0 | 0 | 0 | 0 | 0 | 0 | 0 |
| units per proton[a] | 0 | 0 | 0 | 0 | 0 | 0 | 0 |
| % yield of isomer[c] | 0 | 0 | 0 | 0 | 0 | 0 | 0 |
|  | 0 | 0 | 0 | 0 | 0 | 0 | 0 |
| units per proton[a] | 0 | 0 | 0 | 0 | 0 | 0 | 0 |
| % yield of silyl enol ether[c] | 0 | 0 | 0 | 0 | 0 | 0 | 0 |

[a] Calculated by taking the average of integrations of the specified resonances.
[b] Calculated by dividing units per proton of starting material at time indicated by units per proton value at hour 0.
[c] Calculated by dividing units per proton of product at time indicated by the units per proton value of starting material at hour 0.

VII-2b. Data for Table 2, Entry 2b: Isomerization of pent-4-en-1-ol tert-butyldimethylsilyl ether at 70° C.

Following the general procedure, pent-4-en-1-ol silyl ether (99.0 mg, 0.494 mmol) and catalyst 1+3 (3.5 mg, 0.0050 mmol, 1 mol %) were used. The reaction was conducted at 70° C.

TABLE VII-2b

Isomerization of pent-4-en-1-ol tert-butyldimethylsilylether at 70° C.

Measured integrals in arbitrary units relative to internal standard = 10.0 units and (in bold) derived percent yields of products and amount of starting 1-alkene

| Time | 0 h | 1 h | 2 h | 5 h | 7 h | 23 h | 46 h |
|---|---|---|---|---|---|---|---|
| (5.82 ppm) | 40.52 | 14.83 | 6.62 | 2.26 | 1.29 | 1.63 | 1.49 |
| (4.99 ppm) | 41.01 | 14.81 | 6.66 | 2.40 | 2.14 | 1.64 | 1.63 |

TABLE VII-2b-continued

Isomerization of pent-4-en-1-ol tert-butyldimethylsilylether at 70° C.

| | Measured integrals in arbitrary units relative to internal standard = 10.0 units and (in bold) derived percent yields of products and amount of starting 1-alkene | | | | | | |
|---|---|---|---|---|---|---|---|
| Time | 0 h | 1 h | 2 h | 5 h | 7h | 23 h | 46 h |
| 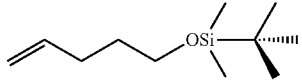 (4.92 ppm) | 40.88 | 14.95 | 6.56 | 2.39 | 2.12 | 1.83 | 1.91 |
| units per proton[a] | 40.80 | 14.83 | 6.61 | 2.35 | 1.85 | 1.70 | 1.67 |
| % starting material remaining[b] | 100 | 36.3 | 16.2 | 5.8 | 4.5 | 4.2 | 4.1 |
| 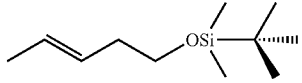 (5.38-5.52 ppm) | 0 | 52.68 | 66.90 | 75.23 | 74.77 | 75.62 | 73.77 |
| units per proton[a] | 0 | 26.34 | 33.45 | 37.62 | 37.39 | 37.81 | 36.89 |
| % yield of product[c] | 0 | 64.6 | 82.0 | 92.2 | 91.6 | 92.7 | 90.4 |
| 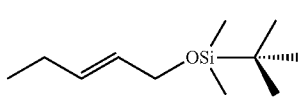 (4.12 ppm) | 0 | 0 | 0 | 0 | trace | 2.03 | 2.52 |
| units per proton[a] | 0 | 0 | 0 | 0 | trace | 1.02 | 1.26 |
| % yield of isomer[c] | 0 | 0 | 0 | 0 | trace | 2.5 | 3.1 |
| 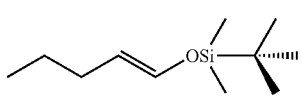 | 0 | 0 | 0 | 0 | 0 | 0 | 0 |
| units per proton[a] | 0 | 0 | 0 | 0 | 0 | 0 | 0 |
| % yield of enol ether[c] | 0 | 0 | 0 | 0 | 0 | 0 | 0 |

[a]Calculated by taking the average of integrations of the specified resonances.
[b]Calculated by dividing units per proton of starting material at time indicated by units per proton value at hour 0.
[c]Calculated by dividing units per proton of product at time indicated by the units per proton value of starting material at hour 0.

VII-3, Data for Table 2, Entry 3: Isomerization of pent-4-en-1-ol tert-butyldiphenylsilyl ether of Using 2 Mol % Catalyst 1+3 and 6 Mol % 4-(tert-butyl)-2-(diisopropylphosphino)-1-methyl-1H-imidazole at 40° C. in Acetone-$d_6$.

Following general procedure, pent-4-en-1-ol tert-butyldiphenylsilyl ether (98.1 mg, 0.302 mmol) and 4-(tert-butyl)-2-(diisopropylphosphino)-1-methyl-1H-imidazole (4.9 mg, 0.019 mmol, 6.4 mol %) were combined with internal standard (0.6 mg) in acetone-$d_6$. After acquiring an initial spectrum catalyst 1+3 (4.4 mg, 0.0063 mmol, 2.1 mol %) was added. The reaction was conducted at 40° C. using an oil bath. At specified time points, $^1$H NMR spectra were obtained.

TABLE VII-3

Isomerization of pent-4-en-1-ol tert-butyldiphenylsilyl ether using 2 mol % catalyst 1 + 3 and 6 mol % imidazolylphosphine ligand at 40° C.

| | Measured integrals in arbitrary units relative to internal standard = 10.0 units and (in bold) derived percent yields of products and amount of starting 1-alkene. | | | | |
|---|---|---|---|---|---|
| Time | 0 h | 2 h | 5 h | 23 h | 48 h |
| 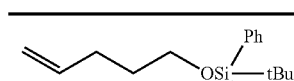 (5.82 ppm) | 54.35 | 32.65 | 18.18 | 4.59 | 2.81 |

TABLE VII-3-continued

Isomerization of pent-4-en-1-ol tert-butyldiphenylsilyl ether using 2 mol % catalyst 1 + 3 and 6 mol % imidazolylphosphine ligand at 40° C.

Measured integrals in arbitrary units relative to internal standard = 10.0 units and (in bold) derived percent yields of products and amount of starting 1-alkene.

| Time | 0 h | 2 h | 5 h | 23 h | 48 h |
|---|---|---|---|---|---|
| pent-4-en-1-ol TBDPS ether (4.99–4.92 ppm) | 109.46 | 64.91 | 36.22 | 8.90 | 5.36 |
| units per proton[a] | | 54.60 | 32.52 | 18.13 | 4.50 | 2.72 |
| % starting material remaining[b] | 100 | 59.6 | 33.2 | 8.2 | 5.0 |
| (E)-pent-3-enyl TBDPS ether (5.40–5.52 ppm) | 0 | 43.17 | 69.40 | 95.99 | 98.57 |
| units per proton[a] | 0 | 21.59 | 34.70 | 48.00 | 49.29 |
| % yield of product[c] | 0 | 39.5 | 63.6 | 87.9 | 90.3 |
| (Z)-pent-3-enyl TBDPS ether (4.20 ppm) | 0 | 0 | 0.25 | 0.72 | 1.06 |
| units per proton[a] | 0 | 0 | 0.12 | 0.36 | 0.53 |
| % yield of isomer[c] | 0 | 0 | 0.2 | 0.6 | 1.0 |
| silyl enol ether | 0 | 0 | 0 | 0 | 0 |
| units per proton[a] | 0 | 0 | 0 | 0 | 0 |
| % yield of silyl enol ether[c] | 0 | 0 | 0 | 0 | 0 |

[a]Calculated by taking the average of integrations of the specified resonances.
[b]Calculated by dividing units per proton of starting material at time indicated by units per proton value at hour 0.
[c]Calculated by dividing units per proton of product at time indicated by the units per proton value of starting material at hour 0.

VII-4. Data for Table 2, Entry 4: Isomerization of dec-9-en-1-ol at 70° C.

Following the general procedure, dec-9-en-1-ol (83.2 mg, 0.532 mmol) and catalyst 1+3 (3.9 mg, 0.0055 mmol, 1 mol %) were used. The reaction was conducted at 70° C.

TABLE VII-4

Isomerization of dec-9-en-1-ol to (E)-dec-8-en-1-ol at 70° C.

Measured integrals in arbitrary units relative to internal standard = 10.0 units and (in bold) derived percent yields of products and amount of starting 1-alkene

| Time | 0 h | 1 h | 2 h | 5 h | 24 h | 46 h |
|---|---|---|---|---|---|---|
| (5.80 ppm) | 55.71 | 19.09 | 8.42 | 2.32 | 1.75 | 1.53 |
| (4.98 ppm) | 55.01 | 19.41 | 8.35 | 2.41 | 1.83 | 1.64 |
| (4.90 ppm) | 56.65 | 19.30 | 8.31 | 2.37 | 1.82 | 1.68 |
| units per proton[a] | 55.81 | 19.27 | 8.36 | 2.37 | 1.80 | 1.62 |
| % starting material remaining[b] | 100 | 34.5 | 15.0 | 4.2 | 3.2 | 2.9 |
| (5.33–5.48 ppm) | 0 | 73.16 | 95.52 | 106.12 | 106.34 | 106.36 |
| units per proton[a] | 0 | 36.58 | 47.76 | 53.06 | 53.17 | 53.18 |
| % yield of product[c] | 0 | 65.5 | 85.6 | 95.1 | 95.3 | 95.3 |
| (0.94 ppm) | 0 | 0 | 0 | 3.58 | 11.93 | 15.75 |
| units per proton[a] | 0 | 0 | 0 | 1.20 | 3.98 | 5.25 |
| % yield of product[c] | 0 | 0 | 0 | 2.1 | 7.1 | 9.4 |

[a]Calculated by taking the average of integrations of the specified resonances.
[b]Calculated by dividing units per proton of starting material at time indicated by units per proton value at hour 0.
[c]Calculated by dividing units per proton of product at time indicated by the units per proton value of starting material at hour 0.

VII-5. Data for Table 2, entry 5: Isomerization of undec-10-en-2-ol at 40° C.

Following the general procedure, undec-10-en-2-ol (85.3 mg, 0.501 mmol) and catalyst 1+3 (3.6 mg, 0.0051 mmol, 1 mol %) were used. The reaction was conducted at 40° C.

For undec-10-en-2-ol in the mixture: $^1$H NMR (500 MHz, acetone-$d_6$) δ 5.80 (tdd, J=7.0, 10.0, 17.0, 1H), 4.98 (dtd, J=1.5, 2.0, 17.0, 1H), 4.90 (tdd, J=1.5, 2.0, 10.0, 1H), 3.63-3.75 (m, 1H), 3.37 (d, J=4.5, 1H), 2.04 (td, J=7.0, 7.0, 2H), 1.33-1.48 (m, 4H), 1.31 (br s, 8H), 1.10 ppm (d, J=6.0, 3H).

For the (E)-undec-9-en-2-ol in the mixture: $^1$H NMR (500 MHz, acetone-$d_6$) δ 5.34-5.47 (m, 2H), 3.64-3.73 (m, 1H), 3.33 (d, J=4.5, 1H), 1.92-2.00 (m, 2H), 1.61 (md, J=5.0, 3H), 1.22-1.46 (m, 12H), 1.10 ppm (d, J=6.0, 3H). $^{13}$C NMR (125.73 MHz, acetone-$d_6$) δ 132.41, 125.24, 67.64, 40.40, 33.34, 30.47, 30.43, 30.03, 26.67, 24.16, 18.12 ppm.

TABLE VII-5

Isomerization of undec-10-en-2-ol to (E)-undec-9-en-2-ol at 40° C.

| | | Measured integrals in arbitrary units relative to internal standard = 10.0 units and (in bold) derived percent yields of products and amount of starting 1-alkene | | | | | |
|---|---|---|---|---|---|---|---|
| Time | | 0 h | 1 h | 2 h | 5 h | 23 h | 46 h |
| (5.80 ppm) | | 25.80 | 21.67 | 16.45 | 11.25 | 1.50 | 0.61 |
| (4.98 ppm) | | 26.08 | 21.56 | 16.65 | 11.40 | 1.73 | 0.55 |
| (4.90 ppm) | | 26.02 | 21.85 | 16.68 | 11.40 | 1.70 | 0.56 |
| units per proton[a] | | 25.97 | 21.69 | 16.59 | 11.35 | 1.64 | 0.57 |
| % starting material remaining[b] | | 100 | 83.5 | 63.9 | 43.7 | 6.3 | 2.2 |
| (5.34-5.47 ppm) | | 0 | 8.64 | 14.03 | 27.66 | 48.52 | 50.73 |
| units per proton[a] | | 0 | 4.32 | 7.02 | 13.83 | 24.26 | 25.37 |
| % yield of product[c] | | 0 | 16.6 | 27.0 | 53.3 | 93.4 | 97.7 |
| (0.94 ppm) | | 0 | 0 | 0 | 0 | 0 | trace |
| units per proton[a] | | 0 | 0 | 0 | 0 | 0 | trace |
| % yield of product[c] | | 0 | 0 | 0 | 0 | 0 | trace |

[a] Calculated by taking the average of integrations of the specified resonances.
[b] Calculated by dividing units per proton of starting material at time indicated by units per proton value at hour 0.
[c] Calculated by dividing units per proton of product at time indicated by the units per proton value of starting material at hour 0.

VIII. Data for Control Experiments Showing Reaction of Cp*Ru Catalyst 1+3 and Internal Alkenes VIII-1a. Data for Isomerization of E-2-Heptene Using 1 Mol % Catalyst 1 at 40° C. in Acetone-$d_6$.

Following general procedure, E-2-heptene (49.3 mg, 0.502 mmol) and catalyst 1+3 (3.5 mg, 0.0050 mmol, 1 mol %) were used. Reaction was conducted at 40° C. using an oil bath. At specified time points, $^1$H NMR spectra were obtained. For GC analysis, see next experiment done in protio acetone.

TABLE VIII-1a

Yields determined by NMR in isomerization of E-2-heptene using 1 mol % catalyst 1 at 40° C.

Measured integrals in arbitrary units relative to internal standard = 10.0 units and (in bold) derived percent yields of products and amount of starting 1-alkene.

| Time | 0 h | 22 h | 165 h |
|---|---|---|---|
| 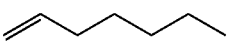 (5.80 ppm) | 0 | 0.53 | 0.73 |
| 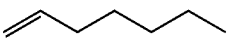 (4.90-4.97 ppm) | 0 | 1.10 | 1.52 |
| units per proton[a] | 0 | 0.54 | 0.75 |
| % 1-alkene formed[d] | 0 | 1.8 | 2.5 |
| 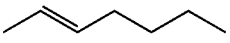 (5.34-5.46 ppm)[c] | 60.26 | 59.12 | 58.71 |
| 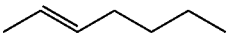 (1.60 ppm) | 90.34 | 88.24 | 86.17 |
| units per proton[a] | 30.12 | 29.47 | 28.98 |
| % of E-2 remaining[b] | 100 | 97.8 | 96.2 |
| 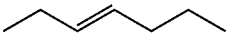 (0.94 ppm) | 0 | 0.88 | 3.1 |
| units per proton[a] | 0 | 0.29 | 1.03 |
| % of E-3[d] | 0 | 1.0 | 3.4 |

[a] Calculated by taking the average of integrations of the specified resonances.
[b] Calculated by dividing units per proton of starting material at time indicated by units per proton value at hour 0.
[c] Includes vinylic H for E-2, E-3 and Z-2, but E-2 dominates throughout.
[d] Calculated by dividing units per proton of product at time indicated by the units per proton value of starting material at hour 0.

VIII-2a. Data for Isomerization of E-2-Heptene Using 1 Mol % Catalyst 1+3 at 40° C. in Acetone-$h_6$.

Following general procedure, E-2-heptene (49.8 mg, 0.507 mmol) and catalyst 1+3 (3.7 mg, 0.0053 mmol, 1 mol %) were used. Reaction was conducted at 40° C. oil bath. At specified time points, 5 μL of reaction mixture was removed under inert atmosphere for GC analysis. Because protio acetone was used, no NMR data are reported.

TABLE VIII-2a

Ratios determined by GC in isomerization of E-2-heptene using 1 mol % catalyst at 40° C.

| Time | 0 h | 48 h |
|---|---|---|
| (2.68 min) | 0 | 8.98 |
| % 1-heptene[a] | 0 | 2.0 |
| (2.94 min) | 1246.55 | 426.70 |
| % of E-2[a] | 100 | 96.6 |
| (2.83 min) | 0 | 5.94 |
| % of E-3[a] | 0 | 1.3 |

TABLE VIII-2a-continued

Ratios determined by GC in isomerization of E-2-heptene using 1 mol % catalyst at 40° C.

| Time | 0 h | 48 h |
|---|---|---|
| (3.09 min) | 0 | 0 |
| % of Z-2[a] | 0 | 0 |
| Total area | 1246.55 | 441.62 |

[a] Calculated by taking the ratios of integrations of the specified retention times.

Figure 16:
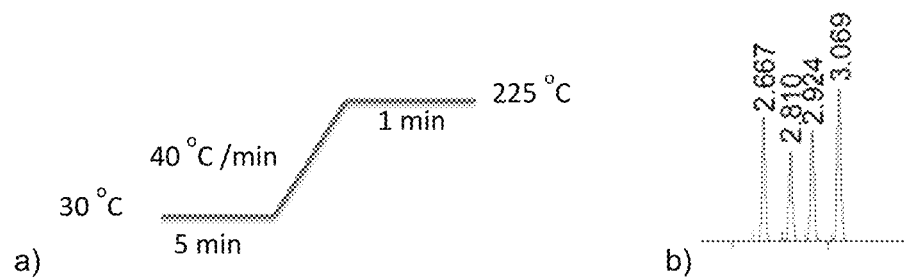
FIG. 16. A) Gas chromatography temperature program for C7 reaction mixtures. B) Gas chromatogram for authentic C7 mixture of 1-heptene, E-3-heptene, E-2-heptene, and Z-2-heptene respectively. (Scheme VIII-2a.)

Scheme VIII-2a. A) Gas chromatography temperature program for C7 reaction mixtures. B) Gas chromatogram for authentic C7 mixture of 1-heptene, E-3-heptene, E-2-heptene, and Z-2-heptene respectively. See FIG. 16.

Figure 17:
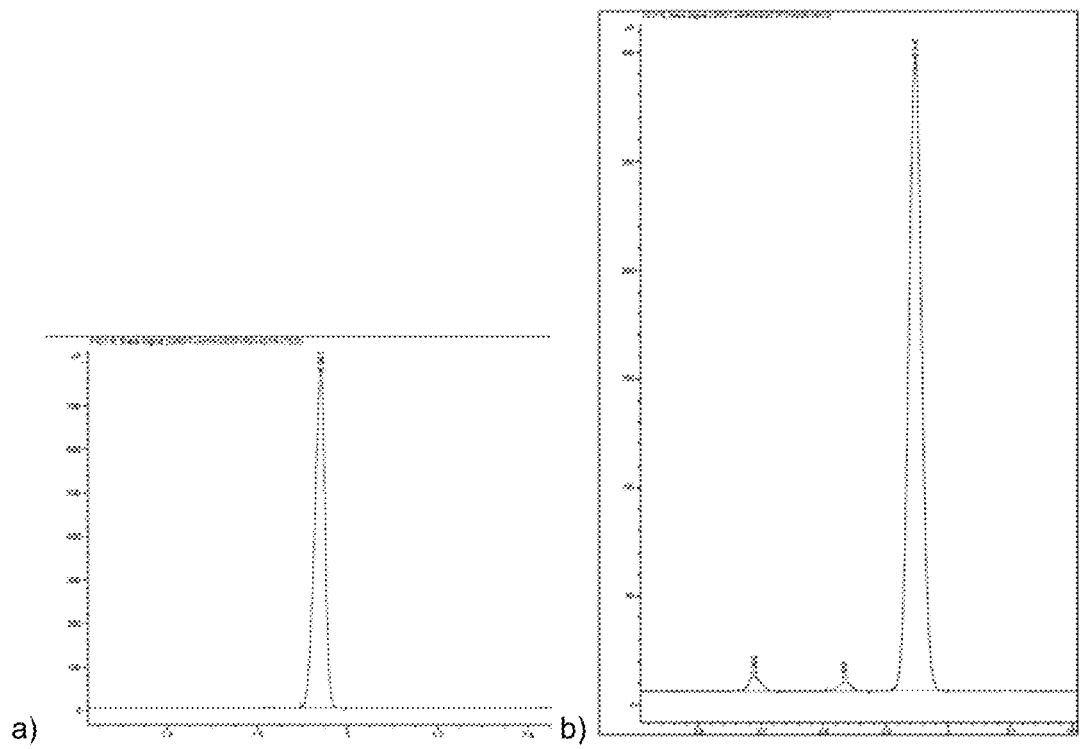
FIG. 17. Gas chromatogram C7 reaction mixtures a) 0 h. b) 48 h. (Scheme VIII-2b.)

Scheme VIII-2b. Gas chromatogram C7 reaction mixtures a) 0 h. b) 48 h. See FIG. 17.

VIII-3a. Data for Isomeriz. Of E-3-Heptene Using 1 Mol % Catalyst 1 at 40° C. in Acetone-d$_6$.

Following general procedure, E-3-heptene (49.5 mg, 0.504 mmol) and catalyst 1+3 (3.6 mg, 0.0051 mmol, 1 mol %) were used. Reaction was conducted at 40° C. oil bath. At specified time points, $^1$H NMR spectra were obtained and 5 μL of reaction mixture was removed under inert atmosphere for GC analysis.

TABLE VIII-3a

Ratios determined by GC in isomerization of E-3-heptene using 1 mol % catalyst 1 + 3 at 40° C.

| Time | 22 h | 48 h | 188 h |
|---|---|---|---|
| (2.68 min) | 0 | 0 | 0 |
| % 1-heptene[a] | 0 | 0 | 0 |
| (2.94 min) | 8.51 | 10.99 | 23.73 |
| % of E-2[a] | 0.9 | 1.3 | 1.8 |
| (2.83 min) | 978.83 | 828.08 | 1278.85 |
| % of E-3[a] | 99.1 | 98.7 | 98.2 |
| 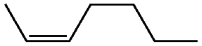 (3.09 min) | 0 | 0 | 0 |
| % of Z-2[a] | 0 | 0 | 0 |
| Total area | 987.34 | 839.07 | 1302.58 |

[a]Calculated by taking the ratios of integrations of the specified retention times.

IX. Table 1: Data for Entries 2e and 2f, Control Experiments with Complexes Lacking N-Heterocyclic Phosphine Ligand.

See below for comparison of rates for entries 2e and 2f with rate of entry 2.

IX-1. Data for Table 1, Entry 2e: Procedure for Isomerization of 1-Heptene Using 4 Mol % [Cp*Ru(CH$_3$CN)$_2$(PiPr$_3$)]PF$_6$ at 40° C. in Acetone-d$_6$.

Catalyst [Cp*Ru(CH$_3$CN)$_2$(PiPr$_3$)]PF$_6$ was prepared by adding an acetone solution of triisopropylphosphine (3.1 mg, 0.0193 mmol, 3.9 mol %) to an acetone solution of [Cp*Ru(CH$_3$CN)$_3$]PF$_6$ (10.4 mg, 0.0206 mmol, 4.1 mol %). After standing overnight at RT, volatiles were removed. Analogous CpRu complexes have been reported (Gutsulyak et al., *Organometallics* (2009), 28, 2655-2657. Osipov et al., *J. Organomet. Chem.* (2007), 692, 5081-5085. Standfest-Hauser et al., *Eur. J. Inorg. Chem.* 2003, 1883-1892). Following the general procedure, 1-heptene (49.1 mg, 0.50 mmol) and internal standard in acetone-d$_6$ were treated with an acetone-d$_6$ solution of the [Cp*Ru(CH$_3$CN)$_2$(PiPr$_3$)]PF$_6$. Reaction was conducted at 40° C. using an oil bath. At specified time points, $^1$H NMR spectra were obtained and 5 μL of reaction mixture was removed under glovebox atmosphere for GC analysis. For addition of Z-2-heptene and E-3-heptene, stock solution of 200 μL was prepared with Z-2-heptene (9.8 mg, 0.10 mmol) and E-2-heptene (9.8 mg, 0.010 mmol) and E-3-heptene (9.4 mg, 0.099 mmol). 10 μL of this solution was added to the reaction point at 216 h time point.

TABLE IX-1a

Yields determined by NMR in isomerization of 1-heptene using 4 mol % catalyst [Cp*Ru(CH$_3$CN)$_2$(PiPr)$_3$]PF$_6$ at 40° C.

Measured integrals in arbitrary units relative to internal standard = 10.0 units and (in bold) derived percent yields of products and amount of starting 1-alkene.

| Time | 0 h | 5 h | 22 h | 72 h | 216 h | 216 h with added Z-2 (1.0%) and E-3 (1.0%)[a] |
|---|---|---|---|---|---|---|
| (5.80 ppm) | 40.00 | 39.91 | 39.44 | 39.34 | 38.49 | 38.41 |
| (4.90-4.97 ppm) | 81.32 | 80.79 | 80.13 | 79.39 | 78.08 | 78.12 |
| units per proton[b] | 40.44 | 40.23 | 39.86 | 39.58 | 38.86 | 38.84 |
| % starting material remaining[c] | 100 | 99.5 | 98.6 | 97.9 | 96.1 | 96.0 |
| (5.34-5.46 ppm)[d] | — | 0.1 | 0.3 | 0.6 | 0.9 | 3.6 |
| units per proton[b] | — | .05 | 0.15 | 0.3 | 0.5 | 1.8 |
| % of E-2[e] | — | 0.1 | 0.4 | 0.7 | 1.2 | 4.4 |
| (0.94 ppm) | — | — | — | — | — | 0.2 |
| units per proton[b] | — | — | — | — | — | 0.07 |
| % of E-3e | — | — | — | — | — | 0.2 |

[a]Spiked with 0.005 mmol (1.0%) of Z-2, 0.005 mmol (1.0%) of E-2, and 0.0050 mmol (1.0%) of E-3.
[b]Calculated by taking the average of integrations of the specified resonances.
[c]Calculated by dividing units per proton of starting material at time indicated by units per proton value at hour 0.
[d]Includes vinylic H for E-2, E-3 and Z-2, but none of these species are present in more than 1% yield until 216 h.
[e]Calculated by dividing units per proton of product at time indicated by the units per proton value of starting material at hour 0.

TABLE IX-1b

Ratios determined by GC in isomerization of 1-heptene using 4 mol % catalyst at 40° C.

| Time | 216 h | 216 h with added Z-2 (1.0%) and E-3 (1.0%)[a] |
|---|---|---|
| (2.85 min) | 42.26 | 363.36 |
| % starting material remaining[b] | 98.7 | 93.2 |
| (3.13 min) | 0.44 | 10.00 |
| % of E-2[b] | 1.0 | 2.6 |
| (3.00 min) | 0.13 | 9.68 |
| % of E-3[b] | 0.2 | 2.5 |
| 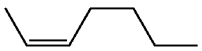 (3.28 min) | — | 6.70 |
| % of Z-2[b] | — | 1.7 |
| Total area | 42.83 | 389.74 |

[a]Spiked with 0.005 mmol (1.0%) of Z-, 0.005 mmol (1.0%) of E-2, and 0.005 mmol (1.0%) of E-3.
[b]Calculated by taking the ratios of integrations of the specified retention times.

Figure 18:
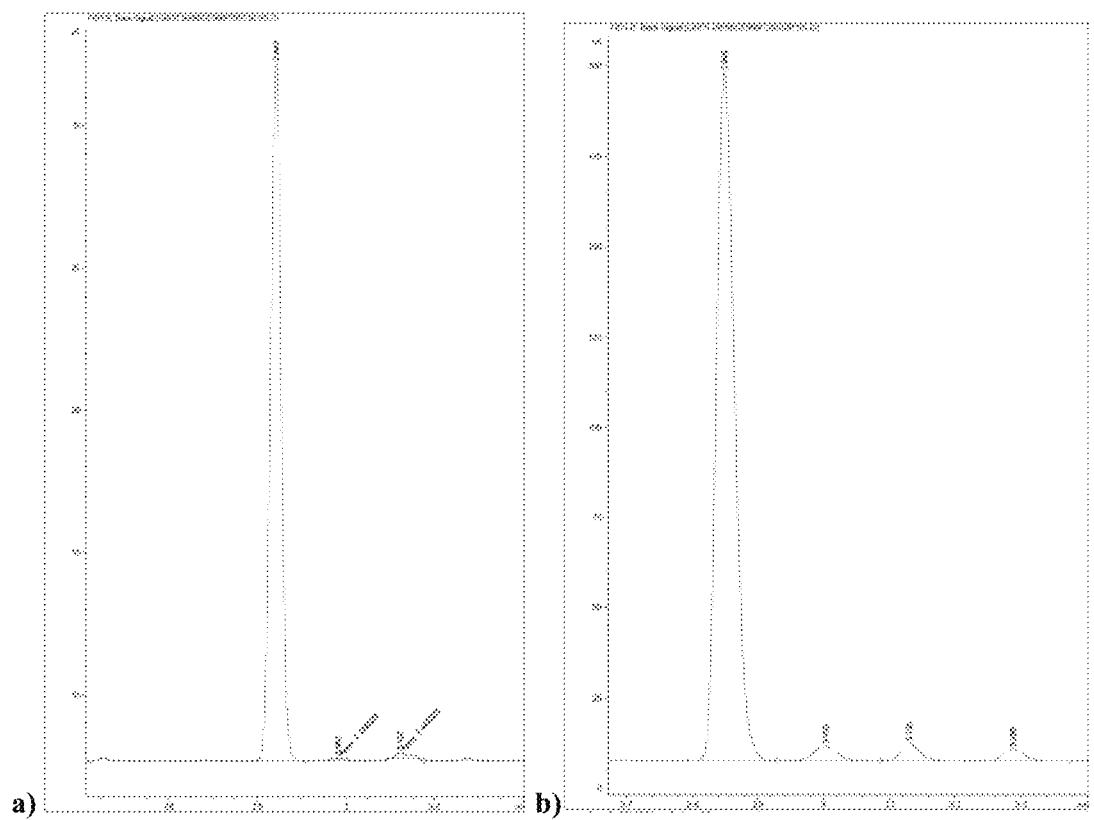
FIG. 18. Gas chromatogram C7 reaction mixtures a) 216 h. b) 216 h with added Z-2-heptene (1.0%), E-2-heptene (1.0%), and E-3-heptene (1.0%). (Scheme IX-1.)

Scheme IX-1. Gas chromatogram C7 reaction mixtures a) 216 h. b) 216 h with added Z-2-heptene (1.0%), E-2-heptene (1.0%), and E-3-heptene (1.0%). See FIG. 18.

IX-2. Data for Table 1, Entry 2f: Procedure for Isomerization of 1-Heptene Using 4 Mol % (Initial Loading, See Note Below) [Cp*Ru(CH$_3$CN)$_2$(PiPr$_2$pH)]PF$_6$ at 40° C. in Acetone-d$_6$.

Catalyst [Cp*Ru(CH$_3$CN)$_2$(PiPr$_2$Ph)]PF$_6$ was prepared by adding an acetone solution of diisopropylphenylphosphine (4.6 mg, 0.024 mmol, 4 mol %) to an acetone solution of [Cp*Ru(CH$_3$CN)$_3$]PF$_6$ (12.2 mg, 0.024 mmol, 4 mol %). After standing 16.7 h at RT, volatiles were removed. Analogous CpRu complexes have been reported (Gutsulyak et al., *Organometallics* (2009), 28, 2655-2657. Osipov et al., *J. Organomet. Chem.* (2007), 692, 5081-5085. Standfest-Hauser et al., *Eur. J. Inorg. Chem.* (2003), 1883-1892). Following the general procedure, 1-heptene (49.5 mg, 0.504 mmol) and internal standard in acetone-d$_6$ were treated with an acetone-d$_6$ solution of the [Cp*Ru(CH$_3$CN)$_2$(PiPr$_2$Ph)]PF$_6$. Reaction was conducted at 40° C. using an oil bath. At specified time points, $^1$H NMR spectra were obtained and 5 µL of reaction mixture was removed under glovebox atmosphere for GC analysis. For addition of Z-2-heptene and E-3-heptene, stock solution of 200 µL was prepared with Z-2-heptene (9.8 mg, 0.10 mmol) and E-2-heptene (9.8 mg, 0.010 mmol) and E-3-heptene (9.4 mg, 0.099 mmol). 10 µL of this solution was added to the reaction point at the 312 h time point.

Note about Evolution of the Catalyst: Over the course of the isomerization reaction, the Cp*Ru fragment migrated from P ($^{31}$P NMR signal at 46.8 ppm) to the arene on P ($^{31}$P NMR signal at 5.9 ppm). At 2 h reaction time, the P-bound complex vs. Ph-bound complex ratio was 2.1 to 1.0 as determined by the $^1$H NMR signals at 7.65-7.42 ppm (unmetallated Ph) and 6.08-6.01 ppm (Cp*Ru-bound Ph), respectively. This ratio became 1.0 to 1.2 at 168 h and 1.0 to 1.4 at 312 h.

TABLE IX-2a

Yields determined by NMR in isomerization of 1-heptene using 4 mol % catalyst (initial loading, see note above) [Cp*Ru(CH$_3$CN)$_2$(PiPr$_2$Ph)]PF$_6$ at 40° C.

Measured integrals in arbitrary units relative to internal standard = 10.0 units and (in bold) derived percent yields of products and amount of starting 1-alkene.

| Time | 0 h | 2 h | 22 h | 48 h | 72 h | 168 h | 312 h | 312 h with added Z-2 (1.0%) and E-3 (1.0%)[a] |
|---|---|---|---|---|---|---|---|---|
| (5.80 ppm) | 52.33 | 53.34 | 51.99 | 51.63 | 51.96 | 51.71 | 51.92 | 51.94 |
| (4.90-4.97 ppm) | 106.64 | 108.65 | 105.16 | 105.07 | 105.44 | 104.16 | 105.03 | 104.95 |
| units per proton[b] | 52.99 | 54.00 | 52.38 | 52.23 | 52.47 | 51.96 | 52.32 | 52.30 |
| % starting material remaining[c] | 100 | 101.9 | 98.8 | 98.6 | 99.0 | 98.1 | 98.7 | 98.7 |
| (5.34-5.46 ppm)[d] | — | — | — | 0.2 | 0.2 | 0.3 | 0.5 | 4.0 |
| units per proton[b] | — | — | — | 0.1 | 0.1 | 0.1 | 0.2 | 2.0 |
| % of E-2[e] | — | — | — | 0.2 | 0.2 | 0.2 | 0.4 | 3.8 |
| (0.94 ppm) | — | — | — | — | — | — | — | 0.3 |
| units per proton[b] | — | — | — | — | — | — | — | 0.1 |
| % of E-3[e] | — | — | — | — | — | — | — | 0.2 |

[a]Spiked with 0.005 mmol (1.0%) of Z-2, 0.005 mmol (1.0%) of E-2, and 0.0050 mmol (1.0%) of E-3.
[b]Calculated by taking the average of integrations of the specified resonances.
[c]Calculated by dividing units per proton of starting material at time indicated by units per proton value at hour 0.
[d]Includes vinylic H for E-2, E-3 and Z-2, but none of these species are present in more than 1% yield until about 312 h.
[e]Calculated by dividing units per proton of product at time indicated by the units per proton value of starting material at hour 0.

TABLE IX-2b

Ratios determined by GC in isomerization of 1-heptene using 4 mol % catalyst (initial loading, see note above) at 40° C.

| Time | 312 h | 312 h with added Z-2 (1.0%) and E-3 (1.0%)[a] |
|---|---|---|
| (2.85 min) % starting material remaining[b] | 648.16 100 | 1009.76 96.4 |
| (3.13 min) % of E-2[b] | 0 0 | 12.44 1.2 |
| (3.00 min) % of E-3[b] | 0 0 | 12.99 1.2 |
| (3.28 min) [Z-2-heptene structure] | 0 | 12.80 |
| % of Z-2[b] | 0 | 1.2 |
| Total area | 648.16 | 1047.99 |

[a]Spiked with 0.005 mmol (1.0%) of Z-2 and 0.005 mmol (1.0%) of E-3.
[b]Calculated by taking the ratios of the integrations of the specified retention times.

Figure 19:
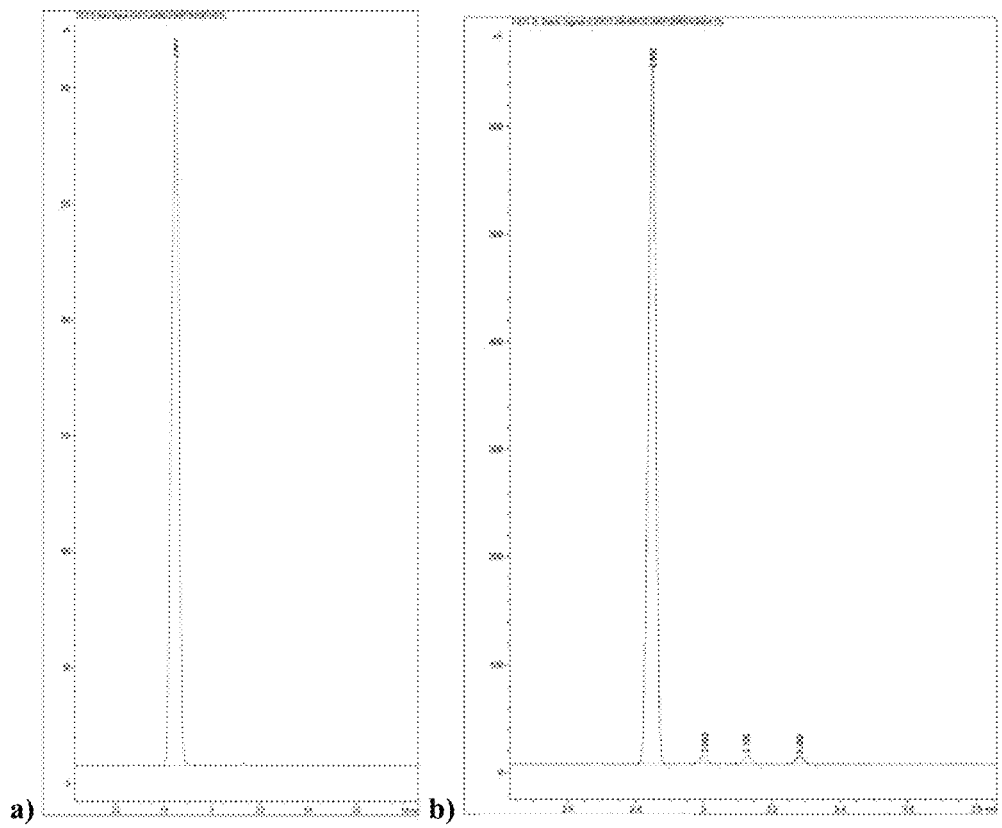
FIG. 19. Gas chromatogram C7 reaction mixtures a) 312 h. b) 312 h with added Z-2-heptene (1.0%), E-2-heptene (1.0%), and E-3-heptene (1.0%). (Scheme IX-2.)

Scheme IX-2. Gas chromatogram C7 reaction mixtures a) 312 h. b) 312 h with added Z-2-heptene (1.0%), E-2-heptene (1.0%), and E-3-heptene (1.0%). See FIG. 19.

Rate Comparison Between Entries 2, 2e, and 2f.

For entry 2 (isomerization of 1-heptene using 1 mol % 1+3).

At 22 h, 93.3% yield of (E)-2-heptene=4.24 h$^{-1}$.

For entry 2e (isomerization using 4 mol % of the PiPr$_3$ complex).

At 216 h, 1.2% yield of (E)-2-heptene=0.0014 h$^{-1}$.

Ratio of rates=4.24/0.0014=3029 to 1.

For entry 2f, the evolution of the catalyst to a coordinatively saturated arene-bound species (presumed to be catalytically inactive) complicates the analysis. However, given that the observed ratio of P-bound to arene-bound species had reached 1.0 to 1.2 at 168 h, we estimate the rate as follows. Assume conservatively that only one half of added catalyst was still active over the entire 168 h. Then catalyst loading would be 2 mol %, giving at 168 h a TOF=(0.2% product/2% catalyst)/168 h=0.0006 h$^{-1}$. Ratio of rates=4.24/0.0006=7067 to 1. We use the 3000 to 1 value as a lower bound.

As shown above, we have found a novel nitrile-containing Cp*Ru catalyst having the unprecedented ability to make >95% yields of (E)-2-alkenes from 1-alkenes. Typical conditions using the nitrile-containing catalyst (J. Am. Chem. Soc. (2014), 136, 1226, with further data in Topics in Catalysis (2014), 57, 1483) for 95% yields employed 1 mol % catalyst over 48 h at 40° C. We have also discovered a significantly faster novel, nitrile-free catalyst having the following characteristics:

(1) Compared to the nitrile-containing catalyst, the nitrile-free catalyst enjoys similar high selectivity, yet is >400 times faster. The rate is so much faster that room temperature reactions are possible, allowing for the use of less catalyst (e.g., 0.1 mol %), and significantly less reaction times (minutes to hours, instead of 2 days);

(2) While the nitrile-free catalyst is somewhat inhibited by protic groups or water, it is still significantly more active than the nitrile-containing catalyst. For example, dec-9-en-1-ol and its tert-butyldimethyl silyl ether are isomerized in 5 h and 15 min, respectively, using 0.5 mol % nitrile-free catalyst at room temperature;

(3) In attempting to use 0.1 mol % catalyst, due to olefin metathesis, alkene impurities (e.g. hydroperoxides that form over time under oxygen in the air) can cause loss of catalyst deactivation. To overcome this issue, one can use more catalyst or pre-purify the alkene, for example, by filtration through alumina or other solid materials; and (4) A rate comparison was made using 1-hexene (see FIGS. 25 and 26 and Tables XIV-6 and 7). Looking at the time required to consume 50% of starting material using 0.25 mol % catalyst at room temperature, it can be seen that the nitrile-free catalyst requires only about 5.6 minutes to complete the reaction, whereas the nitrile-bearing catalyst takes about 420 times longer (2350 min., 39.2 h). Similarly, at about 8 minutes the nitrile-free catalyst has produced 64.4% (E)-2-hexene, whereas the slower catalyst requires about 4320 minutes to make 63.3% product, a rate difference of about 540 times.

In summary, the nitrile-free catalyst is >400 times faster under the conditions employed in our experiments. The experimental section below shows the preparation, characterization, testing and comparison of the nitrile-free and nitrile-containing catalysts.

Preparation of Acetonitrile-Free Catalyst Mixture

In a glovebox, (chloro)pentamethylcyclopentadienylruthenium (II) tetramer [Cp*RuCl]$_4$ (28.8 mg, 0.02647 mmol) was weighed into a resealable J. Young tube, to which was added deoxygenated THF-d$_8$ (0.5 mL). In a separate scintillation vial, diisopropyl(4-tertbutylimidazolyl)phosphine (26.8 mg, 0.1053 mmol) was weighed, to which was added THF-d$_8$ (0.3 mL), forming a solution. The phosphine solution was then transferred quantitatively via pipet to the tetramer solution, rinsing with three portions of THF-d$_8$ (total of 0.2 mL). There was an immediate color change to deep blue after mixing the two solutions. $^1$H and $^{31}$P NMR spectra suggest there are one major and two minor species in the mixture: three imidazole-H peaks in $^1$H NMR (6.75 ppm (d-2 Hz), 6.73 (s)—free phosphine, 6.67 (s)—major peak), and three phosphorus peaks in $^{31}$P NMR (32.9 ppm, 30.5 ppm—major peak, and −18.5 ppm—free phosphine peak). Multiple species have been shown to form in related non-heterocyclic CpRu phosphine systems; equilibrium between monomer and dimer complexes is indicated in these cases.

Initial Isomerization Testing of Catalyst X and Ionized Catalyst Y at 40° C.

The solution made in the previous section was split into three 0.3 mL portions (each containing approximately 0.0351 mmol of Cp*Ru species) and used without further purification. The first portion was added via syringe to a resealable J. Young tube, followed by 1-hexene (7.5 mg, 0.08912 mmol) and THF-d$_8$ (0.2 mL), and initial NMR spectra were observed. The NMR tube was then placed into a 40° C. oil bath. After 167 hours, because only about 6% of alkene had reacted, potassium hexafluorophosphate (6.87 mg, 0.03732 mmol) was added. The solution remained deep blue, and the NMR tube was placed back in the 40° C. oil bath. After 168 hours, thallium (I) hexafluorophosphate (11.2 mg, 0.03206 mmol) was added. The solution remained deep blue. The J. Young was placed back in the 40° C. oil bath for 1 hour. The signals in the $^1$H and $^{31}$P NMR corresponding to the catalyst mixture largely remained the same until the thallium (I) hexafluorophosphate was added; after addition of the excess TlPF$_6$, the three imidazole-H peaks in the $^1$H NMR were replaced by one very broad peak at 7.21 ppm, and, the 3 phosphine peaks were replaced by a very broad peak at 25.9 ppm in the $^{31}$P NMR. The reaction was run without internal standard; ratios of 1-hexene to internal hexane are determined by relative integrations of the alkene signals in each spectrum.

TABLE X

Ratios determined by NMR in isomerization of 1-hexene using 10.0 mol % catalyst mixture, 42.0% KPF$_6$ and 36.0% TIPF$_6$ at room temperature.

| | Measured integrals in arbitrary units relative to solvent peak - not constant between time points = 10.0 units and (in bold) relative ratios of isomers. | | | | |
|---|---|---|---|---|---|
| Time | 0 min | 1 hr | 167 h | 168 h - 1 hr after adding KPF$_6$ | 169 h - 1 hr after adding TIPF$_6$ |
| 1-hexene (5.79 ppm) | 37.6 | 36.6 | 33.6 | 30.9 | 1.20 |
| 1-hexene (4.85-5.01 ppm) | 77.1 | 75.5 | 67.4 | 63.1 | 1.44 |
| units per proton | 38.1 | 37.1 | 33.7 | 31.2 | 0.96 |
| internal hexene (5.35-5.46 ppm)$^a$ | — | 0.64 | 9.06 | 15.6 | 53.2 |
| units per proton | — | 0.32 | 4.53 | 7.8 | 26.6 |
| 1-hexene:internal hexene | 100:0 | 118:1 | 15:1 | 4:1 | 0.045:1 |

$^a$Presumed to be a mixture of E-2 and E-3 hexene, with varying ratios; authentic samples of E-2, Z-2 and E-3 hexene were sequentially added to a mixture of THF and THF-d$_8$ in a separate J. Young NMR tube to verify the chemical shifts of each isomer in THF.

Procedure for Isomerization of 1-Hexene to (E)-2 and (E)-3 Hexenes Using 2.0 Mol % Catalyst and 4.0 Mol % TIPF$_6$ at Room Temperature in THF.

To a resealable J. Young NMR tube in a glovebox, internal standard (Me$_3$Si)$_4$C (~0.2 mg), TIPF$_6$ (3.7 mg, 0.01059 mmol) and 1-hexene (21.0 mg, 0.2500 mmol) were combined with a mixture of dry, deoxygenated THF (400 µL) and THF-d$_8$ (50 µL), and an initial NMR spectrum was acquired. Back in the glovebox, to this mixture was added an aliquot of catalyst mixture solution (40 µL, 0.00468 mmol). The reaction was kept at room temperature and monitored at the times given below.

Procedure for Isomerization of 1-Hexene to (E)-2 and (E)-3 Hexenes Using 0.1 Mol % Catalyst and 0.1 Mol % TIPF$_6$ at Room Temperature in THF.

To a resealable J. Young NMR tube in a glovebox, internal standard (Me$_3$Si)$_4$C (~0.2 mg), TIPF$_6$ (0.2 mg, 0.000572 mmol) and 1-hexene (42.3 mg, 0.5026 mmol) were combined with a mixture of dry, deoxygenated THF (800 µL) and THF-d$_8$ (100 µL), and an initial NMR spectrum was acquired. Back in the glovebox, to this mixture was added an aliquot of catalyst mixture solution (4 µL, 0.000468 mmol). The reaction was kept at room temperature and monitored at the times given below.

TABLE Y

Yields determined by NMR in isomerization of 1-hexene using 2.0 mol % catalyst mixture and 4.0 mol % TIPF$_6$ at room temperature.

| | Measured integrals in arbitrary units relative to internal standard = 10.0 units and (in bold) derived percent yields of products and amount of starting 1-alkene. | | | |
|---|---|---|---|---|
| Time | 0 min | 15 min | 1 h | 3 h |
| (5.79 ppm) | 52.4 | 1.33 | 1.04 | 0.46 |
| (4.85-5.01 ppm) | 105.0 | — | 2.34 | 2.02 |
| units per proton | 52.5 | 1.33 | 1.10 | 0.73 |
| % starting material remaining | 100 | 2.5 | 2.1 | 1.4 |
| (5.35-5.46 ppm)$^a$ | — | 100.9 | 96.3 | 100.3 |
| units per proton$^b$ | — | 45.2 | 35.1 | 30.1 |
| % of E-2 | — | 86.1 | 66.9 | 57.2 |
| E-3 hexene (0.94 ppm) | — | 15.5 | 39.5 | 60.2 |
| units per proton | — | 5.2 | 13.1 | 20.1 |
| % of E-3 | — | 9.8 | 17.0 | 28.0 |

$^a$Signal is a mixture of E-2 and E-3 hexene isomers.
$^b$Proton units for E-2 hexene determined by subtracting proton units of E-3 hexene from total proton units of E-2/E-3 signal.

TABLE Z

Yields determined by NMR in isomerization of 1-hexene using 0.1 mol % catalyst mixture and 0.1 mol % TlPF$_6$ at room temperature.

| Time | 0 min | 15 min | 1 h | 2 h | 4.5 h | 6 h |
|---|---|---|---|---|---|---|
| (5.79 ppm) | 98.5 | 61.6 | 44.8 | 9.42 | 3.41 | 2.11 |
| (4.85-5.01 ppm) | 193.4 | 122.3 | 81.1 | 9.01 | 6.19 | 4.29 |
| units per proton | 97.6 | 61.4 | 42.7 | 9.21 | 3.25 | 2.13 |
| % starting material remaining | 100 | 62.9 | 43.7 | 9.4 | 3.3 | 2.2 |
| (5.35-5.46 ppm)[a] | — | 78.6 | 141.7 | 175.5 | 194.9 | 194.5 |
| units per proton[b] | — | — | — | 86.6 | 95.9 | 95.5 |
| % of E-2 | 0 | 0 | 0 | 88.7 | 98.3 | 97.8 |
|  (0.94 ppm) | — | — | — | 3.49 | 4.77 | 5.19 |
| units per proton | — | — | — | 1.16 | 1.59 | 1.73 |
| % of E-3 | 0 | 0 | 0 | 1.2 | 1.3 | 1.8 |

[a]Signal is a mixture of E-2 and E-3 hexene isomers.
[b]Proton units for E-2 hexene determined by subtracting proton units of E-3 hexene from total proton units of E-2/E-3 signal.

XI. Data for the Preparation, Characterization, and Testing of a Nitrile-Free Versus a Nitrile-Containing Cp*Ru Catalyst: Preparation of Cp*RuiPr$_2$PIm'Cl and its Ionization Data.

XI-1. Complexation of iPr$_2$PIm' with [Cp*RuCl]$_4$:

In a scintillation vial containing a stirbar inside the glovebox, [Cp*RuCl]$_4$ tetramer (125.1 mg, 0.1150 mmol) was weighed out, and dry deoxygenated THF (3 mL) was added, forming a light brown solution. In a separate scintillation vial, the phosphine (117.0 mg, 0.4599 mmol) was weighed out and dissolved in THF (3 mL), forming a colorless solution. The phosphine solution was then pipetted dropwise into the stirred solution of the tetramer. During the addition, the color of the reaction mixture changed from light brown to deep blue. The phosphine solution vial was rinsed with additional THF (3×0.5 mL), and the solution was left to stir for 16 hours. The solvent was then removed in vacuo, forming a blue residue, to which deoxygenated acetone (5 mL) was added. The acetone was removed and the process was repeated (2×5 mL acetone), leaving a blue microcrystalline powder (229.5 mg, 0.4362 mmol, 94.8% yield).

NMR data suggest that three species exist in solution: a major complex, a minor complex, and free phosphine, as evidenced by the three imidazole-H peaks in $^1$H NMR (6.75 ppm (d, 2 Hz), 6.73 (s)—free phosphine, 6.67 (s)—major peak), and three peaks in $^{31}$P NMR (32.9 ppm, 30.5 ppm—major peak, and −18.5 ppm—free phosphine peak). Integrations of imidazole-H proton peaks indicate a ratio of 88.5:10.5 (free ligand):1.5. The three sets of peaks convert to one set of peaks after ionization with TlPF$_6$. Major species before ionization: $^1$H NMR (500 MHz, acetone-d$_6$, −20° C.): 6.78 (s, 1H), 3.27 (s, 3H), 3.02-3.14 (m, 2H), 1.52 (s, 15H), 1.23-1.31 (dd, J=15.5, 7 Hz, 6H), 1.19 (s, 9H), 0.94-1.06 ppm (vbm, 6H). $^{31}$P NMR (202.38 MHz, acetone-d$_6$, −20° C.): 30.2 (s).

The $^{15}$N chemical shifts for the complex were obtained by $^1$H—$^{15}$N HMBC on a sample in acetone-d$_6$ at 30° C. On the basis of previously reported data for imidazolyl and pyridyl-phosphine complexes (e.g., Dalton Trans. 2008, 6497; J. Am. Chem. Soc. 2008, 130, 20), the chemical shift value of −100.6 ppm for the nonmethylated nitrogen is consistent with the structure shown, with neither coordination of N nor significant hydrogen bonding to it.

Figure 20:
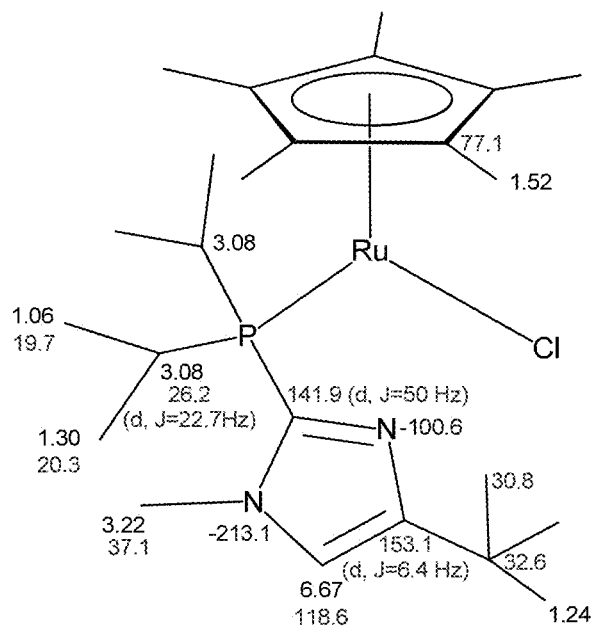
FIG. 20. Graphical representation of results from 1D and 2D NMR experiments on nitrile-free catalyst X.
Figure 21:
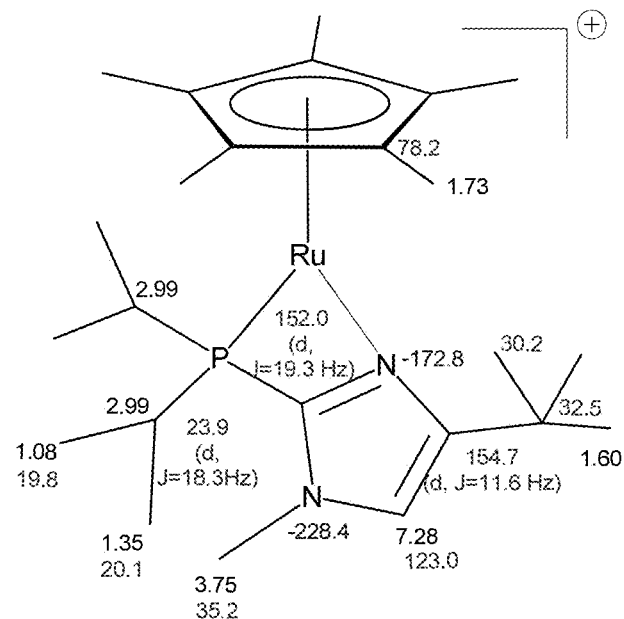
FIG. 21. Graphical representation of results from 1D and 2D NMR experiments on nitrile-free catalyst Y.
Figure 22:
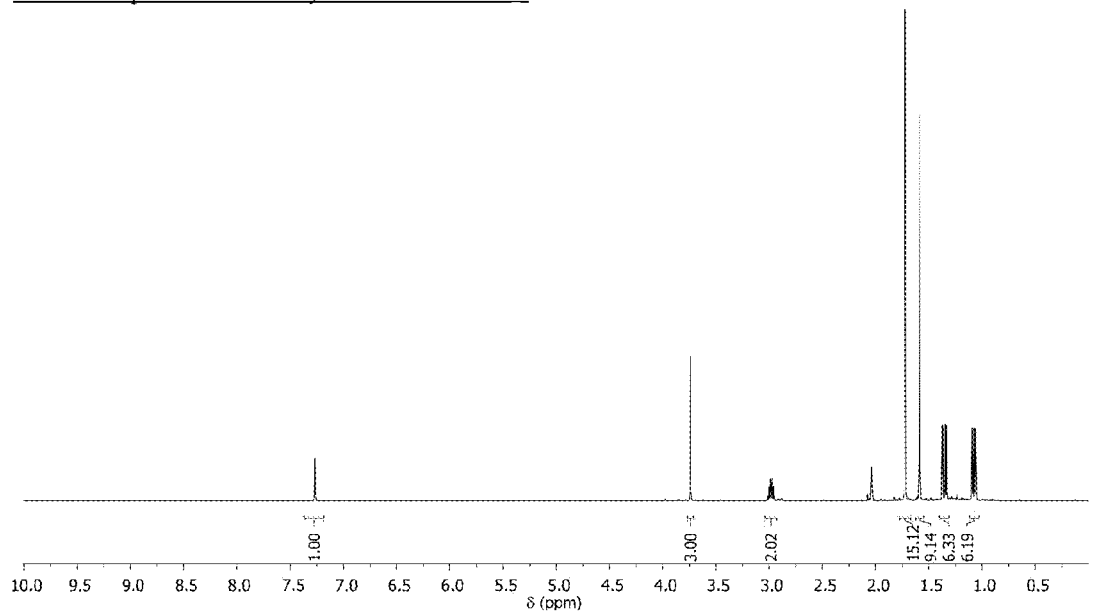
FIG. 22. 1D $^1$H NMR spectrum of nitrile-free catalyst Y.
Figure 23:
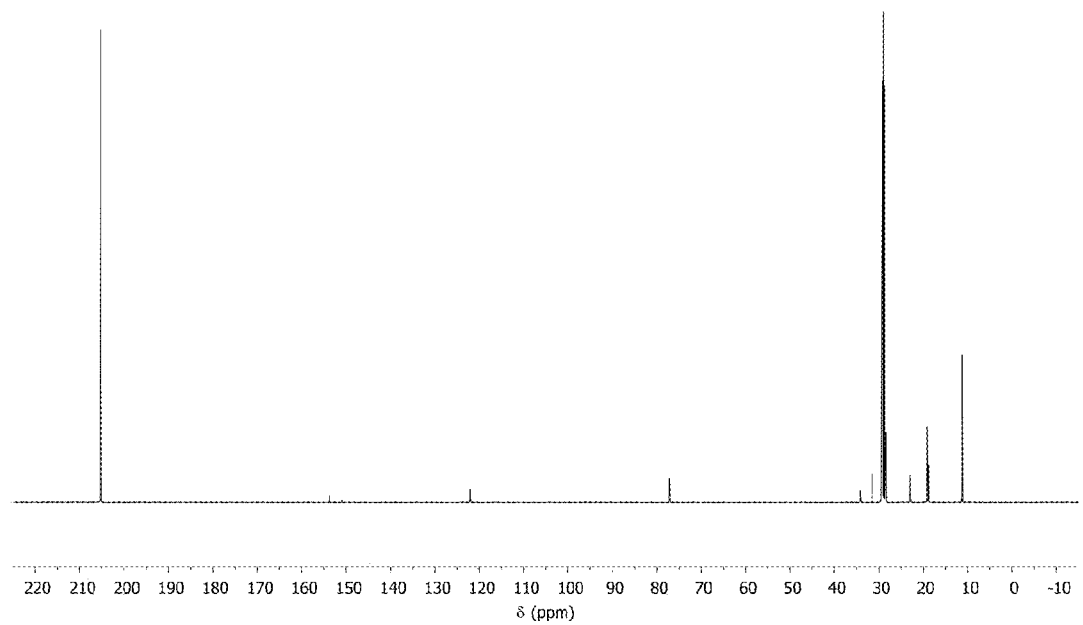
FIG. 23. 1D $^{13}$C NMR spectrum of nitrile-free catalyst Y.

See FIG. 20.

XI-2. Ionization of Cp*RuCl[iPr$_2$PIm']:

In a resealable J. Young tube, the blue powder (8.6 mg, 0.016 mmol) was dissolved in acetone-d$_6$ (0.7 mL), and an initial NMR spectrum was acquired. TlPF$_6$ (7.0 mg, 0.020 mmol) was added to the J. Young NMR tube and rinsed down with additional acetone-d$_6$ (0.1 mL), and the NMR tube was sealed and then placed in a sonicating bath for 1 min. $^1$H NMR (500 MHz, acetone-d$_6$, −20° C.): 7.27 (s, 1H), 3.75 (s, 3H), 2.97-3.00 (d of septet, J=7.1, 7.1 Hz, 2H), 1.73 (d, J=1.5 Hz, 15H), 1.60 (s, 9H), 1.34-1.37 (dd, J=19.8, 7 Hz, 6H), 1.07-1.10 ppm (dd, J=15, 7 Hz, 6H).

See FIGS. 21, 22, 23 and 24.

XI-3. Preparation of Precatalyst Solution A:

In a scintillation vial with a Teflon-lined cap, catalyst X (19.0 mg, 0.0360 mmol) was weighed out and acetone-d$_6$ (500 μL) was added, forming a solution, which was kept in the glovebox, under inert atmosphere. Aliquots of precatalyst solution A were measured from this vial and added to the reaction. NMR data have shown that the catalyst X contained in this solution transforms to the ionized complex (catalyst Y) immediately upon addition to reaction mixtures containing a sufficient amount of TlPF$_6$ (≥1:1 TlPF$_6$: catalyst X) to achieve ionization.

XI-4. Preparation of Precatalyst Solution B:

In a scintillation vial with a Teflon-lined cap, complex mixture (13.2 mg, 0.0251 mmol) was weighed and acetone-d$_6$ (1.00 mL) was added, forming a solution, which was kept in the glovebox, under inert atmosphere. Aliquots of precatalyst solution B were measured from this vial and added to the reaction. NMR data have shown that the catalyst X contained in this solution transforms to the ionized complex (catalyst Y) immediately upon addition to reaction mixtures containing a sufficient amount of TlPF$_6$ (>1:1 TlPF$_6$: catalyst X) to achieve ionization.

XI-5. Treatment to Remove Peroxides from Alkene Samples:

In a scintillation vial outside the glovebox, the alkene (~2-5 g) was weighed out, and was pipetted into a plug containing activated neutral alumina (~100 mg), the filtrate collecting into a resealable scintillation vial. If filtration was performed outside of the glovebox, N$_2$ was bubbled through the sample for 1 minute, after which the vial was sealed and brought into the glovebox. Alkene samples already in the glovebox had been deoxygenated prior to this work. From this point, treated alkenes were isomerized following the same procedure as untreated alkene samples. The following text refers to 'treated' alkenes as alkene samples that have been filtered through an alumina plug as described above to remove peroxides that may be present in the alkenes. 'Untreated' alkenes did not go through the filtering process. Some treated alkene samples showed rate enhancement for isomerization. Presumably, removing the peroxides slows catalyst decomposition.

XII. 0.1 Mol % Catalyst with Commercial, Untreated Alkenes and Alumina-Filtered Treated Alkenes XII.1. Procedure for Isomerization of Untreated[i] 1-Hexene to E-2 and E-3 Hexenes Using 0.1 Mol % Catalyst and 0.15 Mol % TlPF$_6$ at Room Temperature in Acetone-d$_6$.

To a resealable J. Young NMR tube in a glovebox, internal standard (Me$_3$Si)$_4$C (~0.2 mg), TlPF$_6$ (0.3 mg, 0.000859 mmol) and 1-hexene (42.1 mg, 0.500 mmol) were combined with a mixture of deoxygenated acetone-d$_6$ (700 μL), and an initial NMR spectrum was acquired. Back in the glovebox, to this mixture was added an aliquot of precatalyst solution B (20 μL, 0.000500 mmol) and enough acetone-d$_6$ to reach a total volume of 1.0 mL. The reaction was kept at room temperature and monitored at the times given below.

[i]Refer to XI-5 above.

TABLE XII-1

Yields determined by NMR in isomerization of 1-hexene using 0.1 mol % catalyst mixture and 0.1 mol % TlPF$_6$ at room temperature in acetone-d$_6$.

| | Measured integrals in arbitrary units relative to internal standard = 10.0 units and (in bold) derived percent yields of products and amount of starting 1-alkene. | | | | | |
|---|---|---|---|---|---|---|
| Time | 0 min | 15 min | 1 h | 2 h | 4 h | 24 h |
| (5.79 ppm) | 65.8 | 36.5 | 6.88 | 1.60 | 1.32 | 1.07 |
| (4.85-5.01 ppm) | 135.3 | 73.9 | 14.0 | 3.45 | 2.56 | 2.13 |
| units per proton[a] | 66.7 | 36.7 | 6.94 | 1.66 | 1.30 | 1.07 |
| % starting material remaining | 100 | 55.1 | 10.4 | 2.5 | 1.9 | 1.6 |
| (5.35-5.46 ppm)[b] | — | 60.5 | 120.0 | 131.7 | 135.1 | 130.8 |
| (1.60 ppm) | — | 90.9 | 180.1 | 195.1 | 193.4 | 181.4 |
| units per proton[c] | — | 30.3 | 59.6 | 64.6 | 64.5 | 57.7 |
| % of E-2 | 0 | 45.3 | 89.3 | 96.9 | 96.6 | 86.2 |
| (0.94 ppm) | — | — | 2.62 | 4.80 | 9.29 | 31.5 |
| units per proton | — | — | 0.87 | 1.60 | 3.10 | 10.5 |
| % of E-3 | 0 | 0 | 1.3 | 2.4 | 4.6 | 15.7 |

[a]Units calculated by taking the average of the integrations of the two resonances.
[b]Signal is a mixture of vinylic C—H from E-2 and E-3 hexene isomers.
[c]Vinylic proton units for E-2 hexene determined by subtracting proton units of E-3 hexene from total proton units of E-2/E-3 signal.

XII-2. Procedure for Isomerization of Untreated[i] 1-Heptene to E-2 and E-3 Heptanes Using 0.1 Mol % Catalyst and 0.15 Mol % TlPF$_6$ at Room Temperature in Acetone-d$_6$.

To a resealable J. Young tube in a glovebox, internal standard (Me$_3$Si)$_4$C (~0.2 mg), TlPF$_6$ (0.3 mg, 0.000859 mmol) and 1-heptene (49.9 mg, 0.510 mmol) were combined with a mixture of deoxygenated acetone-d$_6$ (700 μL), and an initial NMR spectrum was acquired. Back in the glovebox, to this mixture was added an aliquot of precatalyst solution A (6.9 μL, 0.00050 mmol) and enough acetone-d$_6$ to reach a total volume of 1.0 mL. The reaction was kept at room temperature and monitored at the times given below.

[i]Refer to XI-5 above.

TABLE XII-2

Yields determined by NMR in isomerization of 1-heptene using 0.1 mol % catalyst mixture and 0.1 mol % TlPF$_6$ at room temperature in acetone-d$_6$.

Measured integrals in arbitrary units relative to internal standard = 10.0 units and (in bold) derived percent yields of products and amount of starting 1-alkene.

| Time | 0 min | 15 min | 1 h | 2 h | 3 h | 4 h | 6 h | 31 h |
|---|---|---|---|---|---|---|---|---|
| 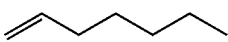 (5.80 ppm) | 54.8 | 26.9 | 6.84 | 2.08 | 1.39 | 1.03 | 1.00 | 1.04 |
| 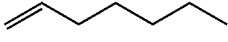 (4.90-4.97 ppm) | 111.2 | 54.6 | 13.9 | 4.36 | 2.36 | 2.09 | 2.04 | 2.06 |
| units per proton[a] | 55.2 | 27.1 | 6.90 | 2.10 | 1.44 | 1.04 | 1.01 | 1.04 |
| % starting material remaining | 100 | 49.1 | 12.5 | 3.8 | 2.6 | 1.9 | 1.8 | 1.9 |
| 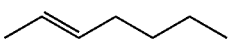 (5.34-5.46 ppm)[b] | — | 51.0 | 97.2 | 107.1 | 108.4 | 106.4 | 105.4 | 103.0 |
| 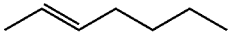 (1.60 ppm) | — | 82.1 | 145.2 | 159.6 | 162.0 | 158.7 | 156.9 | 153.4 |
| units per proton[c] | — | 27.6 | 48.5 | 53.4 | 54.1 | 53.1 | 52.5 | 51.3 |
| % of E-2 | 0 | 49.9 | 87.9 | 96.7 | 98.0 | 96.1 | 95.1 | 93.0 |
| 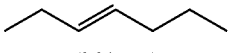 (0.94 ppm) | — | — | 1.07 | 1.51 | 2.18 | 2.70 | 4.22 | 9.33 |
| units per proton | — | — | 0.35 | 0.50 | 0.73 | 0.90 | 1.41 | 3.11 |
| % of E-3 | 0 | 0 | 0.6 | 0.9 | 1.3 | 1.9 | 2.5 | 5.6 |

[a]Units calculated by taking the average of the integrations of the two resonances.
[b]Signal is a mixture of vinylic C—H from E-2 and E-3 heptene isomers.
[b]Vinylic C—H proton units for E-2 heptene determined by subtracting proton units of E-3 heptene from total proton units of E-2/E-3 signal.

XII-3. Procedure for Isomerization of Untreated[i] 1-Octene to E-2, E-3, and E-4 Octenes Using 0.1 Mol % Catalyst and 0.15 Mol % TlPF$_6$ at Room Temperature in Acetone-d$_6$.

To a resealable J. Young tube in a glovebox, internal standard (Me$_3$Si)$_4$C (~0.2 mg), TlPF$_6$ (0.3 mg, 0.000859 mmol) and 1-octene (59.9 mg, 0.534 mmol) were combined with a mixture of deoxygenated acetone-d$_6$ (700 μL), and an initial NMR spectrum was acquired. Back in the glovebox, to this mixture was added an aliquot of precatalyst solution A (6.9 μL, 0.000500 mmol) and enough acetone-d$_6$ to reach a total volume of 1.0 mL. The reaction was kept at room temperature and monitored at the times given below.

[i]Refer to XI-5 above.

TABLE XII-3

Yields determined by NMR in isomerization of 1-octene using 0.1 mol % catalyst mixture and 0.15 mol % TlPF$_6$ at room temperature in acetone-d$_6$.

Measured integrals in arbitrary units relative to internal standard = 10.0 units and (in bold) derived percent yields of products and amount of starting 1-alkene.

| Time | 0 min | 15 min | 1 h | 2 h | 6 h | 24 h | 124 h |
|---|---|---|---|---|---|---|---|
| 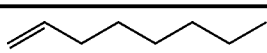 (5.80 ppm) | 47.6 | 39.0 | 33.0 | 28.9 | 26.9 | 20.1 | 14.2 |
| 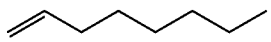 (4.89-4.97 ppm) | 96.3 | 78.9 | 66.7 | 58.3 | 54.1 | 40.9 | 28.6 |
| units per proton[a] | 47.9 | 39.2 | 33.2 | 29.0 | 27.0 | 20.3 | 14.2 |
| % starting material remaining | 100 | 81.9 | 69.3 | 60.6 | 56.3 | 42.3 | 29.6 |

TABLE XII-3-continued

Yields determined by NMR in isomerization of 1-octene using 0.1 mol % catalyst mixture and 0.15 mol % TlPF$_6$ at room temperature in acetone-d$_6$.

Measured integrals in arbitrary units relative to internal standard = 10.0 units and (in bold) derived percent yields of products and amount of starting 1-alkene.

| Time | 0 min | 15 min | 1 h | 2 h | 6 h | 24 h | 124 h |
|---|---|---|---|---|---|---|---|
| 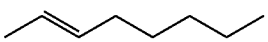  (5.42 ppm)[b] | — | 17.4 | 30.5 | 37.4 | 41.9 | 56.4 | 68.7 |
| (1.60 ppm) | — | 25.7 | 45.0 | 55.2 | 61.5 | 84.0 | 100.4 |
| units per proton[c] | — | 8.61 | 15.1 | 18.6 | 20.7 | 28.1 | 33.9 |
| % of E-2 | 0 | 18.0 | 31.6 | 38.7 | 43.2 | 58.7 | 70.8 |
| 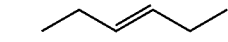  (0.94 ppm) | — | — | — | — | — | — | — |
| units per proton | — | — | — | — | — | — | — |
| % of E-3 | 0 | 0 | 0 | 0 | 0 | 0 | 0 |

[a]Units calculated by taking the average of the integrations of the two resonances.
[b]Signal is a mixture of vinylic C—H protons from internal isomers, although none are present in the above reaction.
[c]Vinylic C—H proton units for E-2 octene determined by subtracting proton units of E-3 octene from total proton units of E-2/E-3 signal.

XII-4. Procedure for Isomerization of Untreated[i] 1-Decene to E-2 and E-3 Decenes Using 0.1 Mol % Catalyst and 0.15 Mol % TlPF$_6$ at Room Temperature in Acetone-d$_6$.

To a resealable J. Young tube in a glovebox, internal standard (Me$_3$Si)$_4$C (~0.2 mg), TlPF$_6$ (0.3 mg, 0.000859 mmol) and 1-decene (70.8 mg, 0.505 mmol) were combined with a mixture of deoxygenated acetone-d$_6$ (700 μL), and an initial NMR spectrum was acquired. Back in the glovebox, to this mixture was added an aliquot of precatalyst solution A (6.9 μL, 0.000500 mmol) and enough acetone-d$_6$ to reach a total volume of 1.0 mL. The reaction was kept at room temperature and monitored at the times given below.

[i]Refer to XI-5 above.

TABLE XII-4

Yields determined by NMR in isomerization of 1-decene using 0.1 mol % catalyst mixture and 0.1 mol % TlPF$_6$ at room temperature in acetone-d$_6$.

Measured integrals in arbitrary units relative to internal standard = 10.0 units and (in bold) derived percent yields of products and amount of starting 1-alkene.

| Time | 0 min | 15 min | 1 h | 2 h | 4 h | 6 h | 24 h |
|---|---|---|---|---|---|---|---|
| 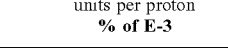  (5.80 ppm) | 42.4 | 36.6 | 33.0 | 31.6 | 30.0 | 29.5 | 26.7 |
| 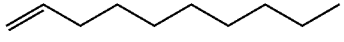  (4.91 ppm) | 85.5 | 73.9 | 66.5 | 63.4 | 60.7 | 59.2 | 53.5 |
| units per proton[a] | 42.6 | 36.8 | 33.1 | 31.7 | 30.2 | 29.6 | 26.7 |
| % starting material remaining | 100 | 86.3 | 77.8 | 74.2 | 70.8 | 61.7 | 55.8 |
| 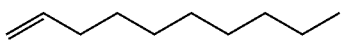  (5.41 ppm)[b] | — | 10.7 | 18.4 | 21.3 | 23.6 | 25.1 | 31.9 |
| 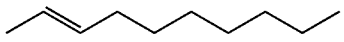  (1.60 ppm) | — | 16.9 | 26.7 | 31.5 | 35.2 | 37.2 | 46.2 |
| units per proton[c] | — | 5.48 | 9.04 | 10.6 | 11.8 | 12.5 | 15.7 |
| % of E-2 | 0 | 12.9 | 21.2 | 22.1 | 24.5 | 26.0 | 32.7 |

TABLE XII-4-continued

Yields determined by NMR in isomerization of 1-decene using 0.1 mol % catalyst mixture and 0.1 mol % TlPF$_6$ at room temperature in acetone-d$_6$.

Measured integrals in arbitrary units relative to internal standard = 10.0 units and (in bold) derived percent yields of products and amount of starting 1-alkene.

| Time | 0 min | 15 min | 1 h | 2 h | 4 h | 6 h | 24 h |
|---|---|---|---|---|---|---|---|
| (0.95 ppm) | | | | | | | |
| units per proton | — | — | — | — | — | — | — |
| % of E-3 | 0 | 0 | 0 | 0 | 0 | 0 | 0 |

[a] Units calculated by taking the average of the integrations of the two resonances.
[b] Signal is a mixture of vinylic C—H internal decene isomers, although these are not present in any detectable quantity within the time points listed above.
[c] Proton units for E-2 decene determined by subtracting proton units of E-3 decene from total proton units of E-2/E-3 signal.

XII-5: Procedure for Isomerization of Treated[i] 1-Hexene to E-2 and E-3 Hexenes Using 0.1 Mol % Catalyst and 0.15 Mol % TlPF$_6$ at Room Temperature in Acetone-d$_6$.

To a resealable J. Young tube in a glovebox, internal standard (Me$_3$Si)$_4$C (~0.2 mg), TlPF$_6$ (0.3 mg, 0.000859 mmol) and alumina-filtered 1-hexene (44.2 mg, 0.525 mmol) were combined with a mixture of deoxygenated acetone-d$_6$ (700 μL), and an initial NMR spectrum was acquired. Back in the glovebox, to this mixture was added an aliquot of precatalyst solution B (20 μL, 0.00050 mmol) and enough acetone-d$_6$ to reach a total volume of 1.0 mL. The reaction was kept at room temperature and monitored at the times given below.

[i] Refer to XI-5 above.

XII-6: Procedure for Isomerization of Treated[i] 1-Heptene to E-2 and E-3 Heptenes Using 0.1 Mol % Catalyst and 0.15 Mol % TlPF$_6$ at Room Temperature in Acetone-d$_6$.

To a resealable J. Young tube in a glovebox, internal standard (Me$_3$Si)$_4$C (~0.2 mg), TlPF$_6$ (0.3 mg, 0.00086 mmol) and alumina-filtered 1-heptene (49.1 mg, 0.500 mmol) were combined with a mixture of deoxygenated acetone-d$_6$ (700 μL), and an initial NMR spectrum was acquired. Back in the glovebox, to this mixture was added an aliquot of precatalyst solution B (20 μl, 0.00050 mmol) and enough acetone-d$_6$ to reach a total volume of 1.0 mL. The reaction was kept at room temperature and monitored at the times given below.

[i] Refer to XI-5 above.

TABLE XII-5

Yields determined by NMR in isomerization of 1-hexene using 0.1 mol % catalyst mixture and 0.1 mol % TlPF$_6$ at room temperature in acetone-d$_6$.

Measured integrals in arbitrary units relative to internal standard = 10.0 units and (in bold) derived percent yields of products and amount of starting 1-alkene.

| Time | 0 min | 15 min | 30 min | 1 h | 2 h | 5 h | 7 h |
|---|---|---|---|---|---|---|---|
| (5.79 ppm) | 84.6 | 44.2 | 27.5 | 11.8 | 2.89 | 1.45 | 1.68 |
| (4.85-5.01 ppm) | 172.9 | 89.9 | 55.8 | 24.0 | 5.71 | 2.86 | 3.04 |
| units per proton[a] | 85.5 | 44.6 | 27.7 | 11.9 | 2.87 | 1.44 | 1.60 |
| % starting material remaining | 100.0 | 52.1 | 32.4 | 13.9 | 3.4 | 1.7 | 1.9 |
| (5.35-5.46 ppm)[b] | — | 79.3 | 112.5 | 144.0 | 162.3 | 164.5 | 165.5 |
| (1.60 ppm) | — | 118.5 | 168.8 | 216.0 | 243.1 | 244.2 | 243.2 |
| units per proton[c] | — | 39.6 | 56.3 | 71.7 | 80.3 | 80.3 | 79.5 |
| % of E-2 | — | 46.3 | 65.8 | 83.8 | 93.9 | 93.9 | 93.0 |
| (0.94 ppm) | — | — | — | 1.97 | 5.01 | 9.52 | 13.9 |
| units per proton | — | — | — | 0.66 | 1.67 | 3.17 | 4.63 |
| % of E-3 | 0 | 0 | 0 | 0.8 | 2.0 | 3.7 | 5.4 |

[a] Units calculated by taking the average of the integrations of the two resonances
[b] Signal is a mixture of E-2 and E-3 vinylic C—Hs.
[c] Proton units for E-2 hexene determined by subtracting proton units of E-3 hexene from total proton units of E-2/E-3 signal.

TABLE XII-6

Yields determined by NMR in isomerization of 1-heptene using 0.1 mol % catalyst mixture and 0.1 mol % TlPF$_6$ at room temperature in acetone-d$_6$.

| | Measured integrals in arbitrary units relative to internal standard = 10.0 units and (in bold) derived percent yields of products and amount of starting 1-alkene. | | | | | | | |
|---|---|---|---|---|---|---|---|---|
| Time | 0 min | 15 min | 30 min | 1 h | 2 h | 4 h | 8.5 h | 52 h |
| 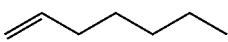 (5.80 ppm) | 34.7 | 29.8 | 26.5 | 22.2 | 19.3 | 16.8 | 15.3 | 13.2 |
| 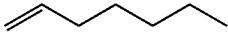 (4.90-4.97 ppm) | 71.2 | 60.5 | 54.0 | 45.2 | 39.3 | 34.2 | 30.8 | 26.9 |
| units per proton[a] | 35.2 | 30.0 | 26.8 | 22.4 | 19.5 | 17.0 | 15.4 | 13.3 |
| % starting material remaining | 100 | 85.2 | 76.1 | 63.6 | 55.4 | 48.2 | 43.8 | 37.8 |
| 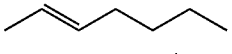 (5.34-5.46 ppm)[b] | — | 12.0 | 19.5 | 27.2 | 33.8 | 38.3 | 42.6 | 45.1 |
| 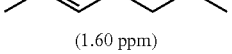 (1.60 ppm) | — | 18.1 | 29.2 | 40.7 | 50.3 | 57.2 | 63.0 | 67.2 |
| units per proton[c] | — | 6.03 | 9.74 | 13.6 | 16.8 | 19.1 | 21.2 | 22.5 |
| % of E-2 | 0 | 17.1 | 27.7 | 38.6 | 47.7 | 54.2 | 60.2 | 63.9 |
| 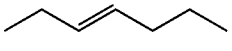 (0.94 ppm) | — | — | — | — | — | — | — | — |
| units per proton | — | — | — | — | — | — | — | — |
| % of E-3 | 0 | 0 | 0 | 0 | 0 | 0 | 0 | 0 |

[a]Units calculated by taking the average of the integrations of the two resonances
[b]Signal is a mixture of E-2 and E-3 heptene isomers.
[c]Vinylic C—H proton units for E-2 heptene determined by subtracting proton units of E-3 heptene from total proton units of E-2/E-3 signal.

XII-7: Procedure for Isomerization of Treated[i] 1-Octene to E-2, E-3, and E-4-Octenes Using 0.1 Mol % Catalyst and 0.1 Mol % TlPF$_6$ at Room Temperature in Acetone-d$_6$.

To a resealable J. Young tube in a glovebox, internal standard (Me$_3$Si)$_4$C (~0.2 mg), TlPF$_6$ (0.3 mg, 0.00143 mmol) and alumina-filtered 1-octene (57.8 mg, 0.515 mmol) were combined with a mixture of deoxygenated acetone-d$_6$ (700 μL), and an initial NMR spectrum was acquired. Back in the glovebox, to this mixture was added an aliquot of precatalyst solution A (6.9 μL, 0.00050 mmol) and enough acetone-d$_6$ to reach a total volume of 1.0 mL. The reaction was kept at room temperature and monitored at the times given below.

[i]Refer to XI-5 above.

TABLE XII-7

Yields determined by NMR in isomerization of 1-octene using 0.1 mol % catalyst mixture and 0.1 mol % TlPF$_6$ at room temperature in acetone-d$_6$.

| | Measured integrals in arbitrary units relative to internal standard = 10.0 units and (in bold) derived percent yields of products and amount of starting 1-alkene. | | | | | | | |
|---|---|---|---|---|---|---|---|---|
| Time | 0 min | 15 min | 30 min | 1 h | 2 h | 4 h | 24 h | 72 h |
| 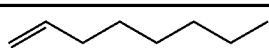 (5.80 ppm) | 59.0 | 10.4 | 2.28 | 1.13 | 1.07 | 1.09 | 0.84 | 0.71 |
| 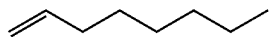 (4.89-4.97 ppm) | 118.3 | 21.3 | 4.82 | 2.51 | 2.38 | 2.23 | 1.71 | 1.38 |
| units per proton[a] | 59.1 | 10.5 | 2.35 | 1.19 | 1.13 | 1.10 | 0.85 | 0.70 |
| % starting material remaining | 100 | 17.8 | 4.0 | 2.0 | 1.9 | 1.9 | 1.4 | 1.2 |

TABLE XII-7-continued

Yields determined by NMR in isomerization of 1-octene using 0.1 mol % catalyst mixture and 0.1 mol % TlPF$_6$ at room temperature in acetone-d$_6$.

Measured integrals in arbitrary units relative to internal standard = 10.0 units and (in bold) derived percent yields of products and amount of starting 1-alkene.

| Time | 0 min | 15 min | 30 min | 1 h | 2 h | 4 h | 24 h | 72 h |
|---|---|---|---|---|---|---|---|---|
| 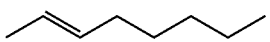 (1.60 ppm) | — | 144.4 | 167.6 | 168.1 | 164.9 | 160.8 | 136.5 | 112.2 |
| units per proton | | 48.1 | 55.9 | 56.0 | 55.0 | 53.3 | 45.5 | 37.4 |
| % of E-2 | — | 81.4 | 94.6 | 94.8 | 93.0 | 90.3 | 77.0 | 63.3 |
| 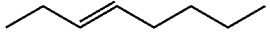 (0.94 ppm) | — | — | 3.38 | 3.91 | 8.13 | 11.2 | 33.3 | 46.6 |
| units per proton | — | — | 1.13 | 1.30 | 2.71 | 3.74 | 11.1 | 15.5 |
| % of E-3 | — | — | 1.9 | 2.2 | 4.6 | 6.3 | 18.8 | 26.3 |

[a]Units calculated by taking the average of the integrations of the two resonances.

XII-8: Procedure for Isomerization of Treated[i] 1-Decene to E-2 and E-3 Decenes Using 0.1 Mol % Catalyst and 0.15 Mol % TlPF$_6$ at Room Temperature in Acetone-d$_6$.

To a resealable J. Young tube in a glovebox, internal standard (Me$_3$Si)$_4$C (~0.2 mg), TlPF$_6$ (0.3 mg, 0.000859 mmol) and alumina-filtered 1-decene (70.1 mg, 0.500 mmol) were combined with a mixture of deoxygenated acetone-d$_6$ (700 μL), and an initial NMR spectrum was acquired. Back in the glovebox, to this mixture was added an aliquot of precatalyst solution B (20 μL, 0.000500 mmol) and enough acetone-d$_6$ to reach a total volume of 1.0 mL. The reaction was kept at room temperature and monitored at the times given below.

[i]Refer to XI-5 above.

TABLE XII-8

Yields determined by NMR in isomerization of 1-decene using 0.1 mol % catalyst mixture and 0.1 mol % TlPF$_6$ at room temperature in acetone-d$_6$.

Measured integrals in arbitrary units relative to internal standard = 10.0 units and (in bold) derived percent yields of products and amount of starting 1-alkene.

| Time | 0 min | 15 min | 30 min | 1 h | 2 h | 4 h | 8.5 h |
|---|---|---|---|---|---|---|---|
| 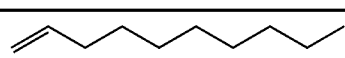 (5.80 ppm) | 69.8 | 46.8 | 31.3 | 15.1 | 4.65 | 1.49 | 1.28 |
| 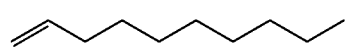 (4.91 ppm) | 142.7 | 94.2 | 63.3 | 30.6 | 9.24 | 3.19 | 2.57 |
| units per proton[a] | 70.6 | 47.0 | 31.5 | 15.2 | 4.64 | 1.54 | 1.28 |
| % starting material remaining | 100 | 66.5 | 44.6 | 21.5 | 6.6 | 2.2 | 1.8 |
|  (1.60 ppm) | — | 75.2 | 118.8 | 164.8 | 198.8 | 206.6 | 204.2 |
| units per proton | — | 25.1 | 39.6 | 54.9 | 66.3 | 68.9 | 68.1 |
| % of E-2 | 0 | 35.5 | 56.1 | 77.8 | 93.8 | 97.5 | 96.4 |
| 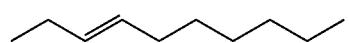 (0.95 ppm) | — | — | — | 1.22 | 2.52 | 4.11 | 7.14 |
| units per proton | — | — | — | 0.41 | 0.84 | 1.37 | 2.38 |
| % of E-3 | 0 | 0 | 0 | 0.6 | 1.2 | 1.9 | 3.4 |

[a]Units calculated by taking the average of the integrations of the two resonances.

XII-9: Procedure for isomerization of treated[i] 4-penten-1-ol to E-3 and E-2 penten-1-ols using 0.5 mol % catalyst and 0.5 mol % TlPF$_6$ at room temperature in acetone-d$_6$.

To a resealable J. Young tube in a glovebox, internal standard (Me$_3$Si)$_4$C (~0.2 mg), TlPF$_6$ (1.0 mg, 0.0029 mmol) and alumina-filtered 4-penten-1-ol (43.5 mg, 0.505 mmol) were combined with a mixture of deoxygenated acetone-d$_6$ (700 μL), and an initial NMR spectrum was acquired. Back in the glovebox, to this mixture was added an aliquot of precatalyst solution B (100 μL, 0.00250 mmol) and enough acetone-d$_6$ to reach a total volume of 1.0 mL. The reaction was kept at room temperature and monitored at the times given below.

[i]Refer to XI-5 above.

XII-10. Procedure for isomerization of treated[i] 1-octene+1 mol % H$_2$O to E-2, E-3, and E-4-octenes using 0.1 mol % catalyst and 0.1 mol % TlPF$_6$ at room temperature in acetone-d$_6$.

To a resealable J. Young tube in a glovebox, internal standard Me$_3$Si)$_4$C (~0.2 mg), TlPF$_6$ (0.3 mg, 0.00143 mmol) and alumina-filtered 1-octene (57.8 mg, 0.515 mmol) were combined with a mixture of deoxygenated acetone-d$_6$ (700 μL), and an initial NMR spectrum was acquired. Back in the glovebox, to this mixture was added an aliquot of precatalyst solution A (6.9 μL, 0.00050 mmol) and enough acetone-d$_6$ to reach a total volume of 1.0 mL. The reaction was kept at room temperature and monitored at the times given below.

[i]Refer to XI-5 above.

TABLE XII-9

Yields determined by NMR in isomerization of 4-penten-1-ol using 0.5 mol % catalyst mixture and 0.5 mol % TlPF$_6$ at room temperature in acetone-d$_6$.

Measured integrals in arbitrary units relative to internal standard = 10.0 units and (in bold) derived percent yields of products and amount of starting 1-alkene.

| Time | 0 min | 15 min | 30 min | 1 h | 5 h | 7 h | 24 h | 48 h |
|---|---|---|---|---|---|---|---|---|
| 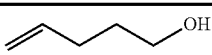 (5.84 ppm) | 144.4 | 89.8 | 47.0 | 4.67 | 3.27 | 2.97 | 3.05 | 3.27 |
| 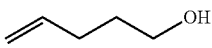 (4.85-5.08 ppm) | 295.4 | 183.1 | 96.2 | 9.22 | 6.32 | 6.42 | 6.23 | 6.06 |
| units per proton[a] | 146.1 | 90.7 | 47.6 | 4.64 | 3.22 | 3.09 | 3.08 | 3.15 |
| % starting material remaining | 100 | 62.1 | 32.5 | 3.2 | 2.2 | 2.1 | 2.1 | 2.2 |
| 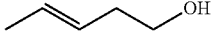 (5.35-5.46 ppm)[b] | — | 113.3 | 198.1 | 284.6 | 274.8 | 266.1 | 265.9 | 265.7 |
| units per proton[c] | — | 56.7 | 99.0 | 141.9 | 137.4 | 133.0 | 133.0 | 132.9 |
| % yield product | 0 | 38.8 | 67.8 | 97.1 | 94.0 | 91.1 | 91.0 | 90.9 |
| 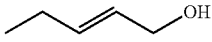 (0.96 ppm) | — | — | — | 2.19 | 6.49 | 5.83 | 6.18 | 6.02 |
| units per proton | — | — | — | 0.73 | 2.16 | 1.94 | 2.06 | 2.01 |
| % of isomer | 0 | 0 | 0 | 0.5 | 1.5 | 1.3 | 1.4 | 1.4 |
| 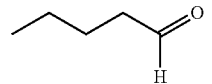 (9.72 ppm) | — | — | — | — | 4.85 | 6.04 | 7.53 | 7.61 |
| units per proton | — | — | — | — | 4.85 | 6.04 | 7.53 | 7.61 |
| % of aldehyde | 0 | 0 | 0 | 0 | 3.3 | 4.1 | 5.2 | 5.2 |

[a]Units calculated by taking the average of the integrations of the two resonances.
[b]Signal is a mixture of E-3- and E-2-penten-1-ol isomers.
[c]Vinylic C—H proton units for E-3-penten-1-ol determined by subtracting proton units of E-2-penten-1-ol from total proton units of E-3/E-2 signal.

TABLE XII-10

Yields determined by NMR in isomerization of 1-octene + 1 mol % H₂O using 0.1 mol % catalyst mixture and 0.1 mol % TlPF₆ at room temperature in acetone-d₆.

Measured integrals in arbitrary units relative to internal standard = 10.0 units and (in bold) derived percent yields of products and amount of starting 1-alkene.

| Time | 0 min | 15 min | 1 h | 2 h | 4 h | 7.5 h | 29 h | 57.5 h |
|---|---|---|---|---|---|---|---|---|
| 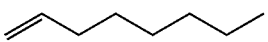 (5.80 ppm) | 47.9 | 35.3 | 20.4 | 11.9 | 4.36 | 1.59 | 1.13 | 0.93 |
| 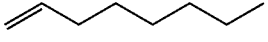 (4.89-4.97 ppm) | 96.9 | 71.8 | 41.2 | 23.8 | 8.93 | 2.99 | 1.86 | 1.43 |
| units per proton[a] | 48.2 | 35.6 | 20.5 | 11.9 | 4.41 | 1.54 | 1.03 | 0.82 |
| % starting material remaining | 100 | 73.9 | 42.5 | 24.7 | 9.2 | 3.2 | 2.1 | 1.7 |
| 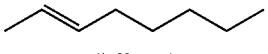 (1.60 ppm) | — | 39.9 | 55.6 | 109.8 | 130.9 | 139.8 | 137.3 | 136.4 |
| units per proton | — | 13.3 | 18.5 | 36.6 | 43.6 | 46.6 | 45.8 | 45.5 |
| % of E-2 | — | 27.6 | 38.5 | 75.9 | 90.5 | 96.6 | 94.9 | 94.3 |
| 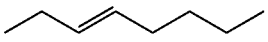 (0.94 ppm) | — | — | — | — | 1.32 | 2.14 | 3.05 | 4.02 |
| units per proton | — | — | — | — | 0.44 | 0.71 | 1.02 | 1.34 |
| % of E-3 | 0 | 0 | 0 | 0 | 0.9 | 1.5 | 2.1 | 2.8 |

[a]Units calculated by taking the average of the integrations of the two resonances XIII. 0.5 Mol % Catalyst with Commercial, Untreated Alkenes and Alumina-Filtered Treated Alkenes.

XIII-1. Procedure for Isomerization of Treated[i] 1-Hexene to E-2 and E-3 Hexenes Using 0.5 Mol % Catalyst and 0.5 Mol % TlPF₆ at Room Temperature in Acetone-d₆.

To a resealable J. Young tube in a glovebox, internal standard (Me₃Si)₄C (~0.2 mg), TlPF₆ (1 mg, 0.0029 mmol) and alumina-filtered 1-hexene (42.1 mg, 0.500 mmol) were combined with a mixture of deoxygenated acetone-d₆ (700 μL), and an initial NMR spectrum was acquired. Back in the glovebox, to this mixture was added an aliquot of catalyst solution B (100 μL, 0.00250 mmol) and enough acetone-d₆ to reach a total volume of 1.0 mL. The reaction was kept at room temperature and monitored at the times given below.

[i]Refer to XI-5 above.

TABLE XIII-1

Yields determined by NMR in isomerization of 1-hexene using 0.5 mol % catalyst mixture and 0.5 mol % TlPF₆ at room temperature in acetone-d₆.
Measured integrals in arbitrary units relative to internal standard = 10.0 units and (in bold) derived percent yields of products and amount of starting 1-alkene.

| Time | 0 min | 15 min | 30 min | 1 h |
|---|---|---|---|---|
| 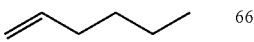 (5.79 ppm) | 66.0 | 2.14 | 1.43 | 1.36 |
| 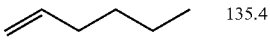 (4.85-5.01 ppm) | 135.4 | 4.17 | 2.46 | 2.60 |
| units per proton[a] | 66.9 | 2.11 | 1.33 | 1.33 |
| % starting material remaining | 100 | 3.2 | 2.0 | 2.0 |
| 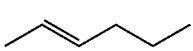 (5.35-5.46 ppm)[b] | — | 131.8 | 131.8 | 131.8 |
| 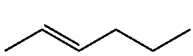 (1.60 ppm) | — | 197.7 | 194.5 | 189.2 |
| units per proton[c] | — | 64.7 | 64.1 | 62.1 |
| % of E-2 | 0 | 96.7 | 95.9 | 92.7 |
| 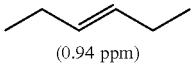 (0.94 ppm) | — | 3.61 | 7.27 | 14.4 |
| units per proton | — | 1.20 | 2.42 | 4.82 |
| % of E-3 | 0 | 1.8 | 3.6 | 7.2 |

[a]Units calculated by taking the average of the integrations of the two resonances.
[b]Signal is a mixture of E-2 and E-3 hexene isomers.
[c]Vinylic C—H proton units for E-2 hexene determined by subtracting proton units of E-3 hexene from total proton units of E-2/E-3 signal XIII-2. Procedure for Isomerization of Untreated[i] 1-Heptene to E-2 and E-3 Heptenes Using 0.5 Mol % Catalyst and 0.5 Mol % TlPF$_6$ at Room Temperature in Acetone-d$_6$.

To a resealable J. Young tube in a glovebox, internal standard (Me$_3$Si)$_4$C (~0.2 mg), TlPF$_6$ (1 mg, 0.0029 mmol) and 1-heptene (49.1 mg, 0.500 mmol) were combined with a mixture of deoxygenated acetone-d$_6$ (700 µL), and an initial NMR spectrum was acquired. Back in the glovebox, to this mixture was added an aliquot of precatalyst solution B (100 µL, 0.00250 mmol) and enough acetone-d$_6$ to reach a total volume of 1.0 mL. The reaction was kept at room temperature and monitored at the times given below.

[i]Refer to XI-5 above.

TABLE XIII-2

Yields determined by NMR in isomerization of 1-heptene using 0.1 mol % catalyst mixture and 0.1 mol % TlPF$_6$ at room temperature in acetone-d$_6$.

| Time | Measured integrals in arbitrary units relative to internal standard = 10.0 units and (in bold) derived percent yields of products and amount of starting 1-alkene. | | | | |
|---|---|---|---|---|---|
| | 0 min | 15 min | 30 min | 1 h | 2 h |
| 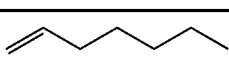 (5.80 ppm) | 40.0 | 1.21 | 0.83 | 0.75 | 0.81 |
| 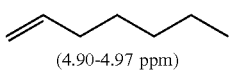 (4.90-4.97 ppm) | 80.9 | 2.31 | 1.55 | 1.55 | 1.55 |
| units per proton[a] | 40.2 | 1.18 | 0.80 | 0.76 | 0.79 |
| % starting material remaining | 100 | 2.9 | 2.0 | 1.9 | 2.0 |
| 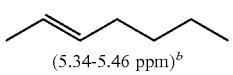 (5.34-5.46 ppm)[b] | — | 78.0 | 79.1 | 79.7 | 80.6 |
| 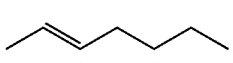 (1.60 ppm) | — | NA | 117.3 | 115.5 | 112.1 |
| units per proton[c] | — | 38.4 | 38.8 | 38.0 | 37.2 |
| % of E-2 | 0 | 95.5 | 96.5 | 94.6 | 92.6 |
| 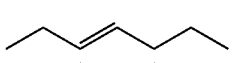 (0.94 ppm) | — | 1.80 | 3.18 | 6.82 | 9.70 |
| units per proton | — | 0.60 | 1.06 | 2.27 | 3.23 |
| % of E-3 | 0 | 1.5 | 2.6 | 5.6 | 8.0 |

[a]Units calculated by taking the average of the integrations of the two resonances.
[b]Signal is a mixture of E-2 and E-3 heptene isomers.
[c]Vinylic C—H proton units for E-2 heptene determined by subtracting proton units of E-3 heptene from total proton units of E-2/E-3 signal.

XIII-3. Procedure for Isomerization of Untreated[i] 1-Octene to E-2, E-3, and E-4 Octenes Using 0.5 Mol % Catalyst and 0.5 Mol % TlPF$_6$ at Room Temperature in Acetone-d$_6$.

To a resealable J. Young tube in a glovebox, internal standard (Me$_3$Si)$_4$C (~0.2 mg), TlPF$_6$ (0.9 mg, 0.0026 mmol) and 1-octene (56.1 mg, 0.500 mmol) were combined with a mixture of deoxygenated acetone-d$_6$ (700 µL), and an initial NMR spectrum was acquired. Back in the glovebox, to this mixture was added an aliquot of precatalyst solution B (100 µL, 0.00250 mmol) and enough acetone-d$_6$ to reach a total volume of 1.0 mL. The reaction was kept at room temperature and monitored at the times given below.

[i]Refer to XI-5 above.

TABLE XIII-3

Yields determined by NMR in isomerization of 1-octene using 0.5 mol % catalyst mixture and 0.5 mol % TlPF$_6$ at room temperature in acetone-d$_6$.

Measured integrals in arbitrary units relative to internal standard = 10.0 units and (in bold) derived percent yields of products and amount of starting 1-alkene.

| Time | 0 min | 15 min | 30 min | 1 h | 2 h | 5 h |
|---|---|---|---|---|---|---|
| (5.80 ppm) | 74.0 | 5.68 | 2.36 | 1.37 | 1.51 | 1.67 |
| (4.89-4.97 ppm) | 150.0 | 11.9 | 4.72 | 2.95 | 2.77 | 2.93 |
| units per proton[a] | 74.5 | 5.82 | 2.36 | 1.42 | 1.45 | 1.57 |
| % starting material remaining | 100 | 7.8 | 3.2 | 1.9 | 1.9 | 2.1 |
| (1.60 ppm) | — | 211.4 | 223.2 | 217.7 | 215.6 | 208.4 |
| units per proton | — | 70.5 | 73.7 | 72.6 | 71.9 | 69.5 |
| % of E-2 | 0 | 94.6 | 99.8 | 97.4 | 96.5 | 93.3 |
| (0.94 ppm) | — | — | 4.01 | 5.41 | 9.79 | 15.4 |
| units per proton | — | — | 1.34 | 1.80 | 3.26 | 5.1 |
| % of E-3 | 0 | 0 | 1.8 | 2.4 | 4.4 | 6.9 |

[a]Units calculated by taking the average of the integrations of the two resonances XIII-4. Procedure for Isomerization of Untreated[i] 1-Decene to E-2 and E-3 Decenes Using 0.5 Mol % Catalyst and 0.5 Mol % TlPF$_6$ at Room Temperature in Acetone-d$_6$.

To a resealable J. Young tube in a glovebox, internal standard (Me$_3$Si)$_4$C (~0.2 mg), TlPF$_6$ (1.0 mg, 0.0029 mmol) and 1-decene (70.2 mg, 0.501 mmol) were combined with a mixture of deoxygenated acetone-d$_6$ (700 μL), and an initial NMR spectrum was acquired. Back in the glovebox, to this mixture was added an aliquot of precatalyst solution B (100 μL, 0.00250 mmol) and enough acetone-d$_6$ to reach a total volume of 1.0 mL. The reaction was kept at room temperature and monitored at the times given below.

[i]Refer to XI-5 above.

TABLE XIII-4

Yields determined by NMR in isomerization of 1-decene using 0.5 mol % catalyst mixture and 0.5 mol % TlPF$_6$ at room temperature in acetone-d$_6$.

Measured integrals in arbitrary units relative to internal standard = 10.0 units and (in bold) derived percent yields of products and amount of starting 1-alkene.

| Time | 0 min | 15 min | 30 min | 1 h | 2 h |
|---|---|---|---|---|---|
| (5.80 ppm) | 44.3 | 5.36 | 1.58 | 0.94 | 0.92 |
| (4.91 ppm) | 89.2 | 10.4 | 3.02 | 1.72 | 1.69 |
| units per proton | 44.5 | 5.29 | 1.55 | 0.90 | 0.88 |
| % starting material remaining | 100 | 11.8 | 3.5 | 2.0 | 2.0 |
| (1.60 ppm) | — | 118.5 | 128.3 | 130.0 | 129.5 |
| units per proton | — | 39.5 | 42.8 | 43.3 | 43.2 |
| % of E-2 | 0 | 88.8 | 96.1 | 97.4 | 97.0 |

TABLE XIII-4-continued

Yields determined by NMR in isomerization of 1-decene using 0.5 mol % catalyst mixture and 0.5 mol % TlPF$_6$ at room temperature in acetone-d$_6$.

| | Measured integrals in arbitrary units relative to internal standard = 10.0 units and (in bold) derived percent yields of products and amount of starting 1-alkene. | | | | |
|---|---|---|---|---|---|
| Time | 0 min | 15 min | 30 min | 1 h | 2 h |
| ⌒=⌒⌒⌒ (0.95 ppm) | — | 0.54 | 2.26 | 2.80 | 4.38 |
| units per proton | — | 0.18 | 0.75 | 0.93 | 1.46 |
| % of E-3 | 0 | 0.4 | 1.7 | 2.1 | 3.3 |

[a] Units calculated by taking the average of the integrations of the two resonances XIII-5. Procedure for Isomerization of Untreated[i] 4-Penten-1-ol to E-3 and E-2 Penten-1-Ols Using 0.5 Mol % Catalyst and 0.5 Mol % TlPF$_6$ at Room Temperature in Acetone-d$_6$.

To a resealable J. Young tube in a glovebox, internal standard (Me$_3$Si)$_4$C (~0.2 mg), TlPF$_6$ (1.0 mg, 0.0029 mmol) and 4-penten-1-ol (43.5 mg, 0.505 mmol) were combined with a mixture of deoxygenated acetone-d$_6$ (700 µL), and an initial NMR spectrum was acquired. Back in the glovebox, to this mixture was added an aliquot of precatalyst solution B (100 µL, 0.00250 mmol) and enough acetone-d$_6$ to reach a total volume of 1.0 mL. The reaction was kept at room temperature and monitored at the times given below.

[i] Refer to XI-5 above.

TABLE XIII-5

Yields determined by NMR in isomerization of 4-penten-1-ol using 0.5 mol % catalyst mixture and 0.5 mol % TlPF$_6$ at room temperature in acetone-d$_6$.

| | Measured integrals in arbitrary units relative to internal standard = 10.0 units and (in bold) derived percent yields of products and amount of starting 1-alkene. | | | | | | | |
|---|---|---|---|---|---|---|---|---|
| Time | 0 min | 15 min | 30 min | 45 min | 1 h | 2 h | 7 h | 24 h |
| ⌒=⌒⌒⌒OH (5.84 ppm) | 60.5 | 26.7 | 7.91 | 1.62 | 1.51 | 2.18 | 1.47 | 1.22 |
| ⌒=⌒⌒⌒OH (4.85-5.08 ppm) | 124.1 | 54.6 | 16.3 | 3.37 | 2.99 | 3.26 | 2.64 | 2.63 |
| units per proton[a] | 61.3 | 27.0 | 8.03 | 1.65 | 1.50 | 1.90 | 1.40 | 1.27 |
| % starting material remaining | 100 | 44.0 | 13.1 | 2.7 | 2.5 | 3.1 | 2.3 | 2.1 |
| ⌒⌒=⌒⌒OH (5.35-5.46 ppm)[b] | — | 70.9 | 107.3 | 119.4 | 118.2 | 117.1 | 111.9 | 111.3 |
| units per proton[c] | — | 35.5 | 53.5 | 59.7 | 59.1 | 58.6 | 56.0 | 55.7 |
| % yield product | 0 | 57.8 | 87.3 | 97.4 | 96.4 | 95.6 | 91.3 | 90.8 |
| ⌒⌒⌒=⌒OH (0.96 ppm) | — | — | 0.43 | 1.35 | 1.81 | 2.68 | 3.21 | 2.63 |
| units per proton | — | — | 0.14 | 0.45 | 0.60 | 0.89 | 1.07 | 0.88 |
| % of isomer | 0 | 0 | 0.2 | 0.7 | 0.9 | 1.5 | 1.7 | 1.4 |
| ⌒⌒⌒CHO (9.72 ppm) | — | — | — | 0.09 | 0.29 | 1.19 | 3.05 | 3.78 |
| units per proton | — | — | — | 0.09 | 0.29 | 1.19 | 3.05 | 3.78 |
| % of aldehyde | 0 | 0 | 0 | 0.1 | 0.5 | 1.9 | 5.0 | 6.2 |

[a] Units calculated by taking the average of the integrations of the two resonances.
[b] Signal is a mixture of E-3-and E-2-penten-1-ol isomers.
[c] Vinylic C—H proton units for E-3-penten-1-ol determined by subtracting proton units of E-2-penten-1-ol from total proton units of E-3/E-2 signal.

XIII-6. Procedure for Isomerization of Untreated[i] 9-Decen-1-ol to E-8 and E-7 Decen-1-Ols Using 0.5 Mol % Catalyst and 0.5 Mol % TlPF$_6$ at Room Temperature in Acetone-d$_6$.

To a resealable J. Young tube in a glovebox, internal standard (Me$_3$Si)$_4$C (~0.2 mg), TlPF$_6$ (1.0 mg, 0.0029 mmol) and 9-decen-1-ol (78.3 mg, 0.501 mmol) were combined with a mixture of deoxygenated acetone-d$_6$ (700 µL), and an initial NMR spectrum was acquired. Back in the glovebox, to this mixture was added an aliquot of precatalyst solution B (100 µL, 0.00250 mmol) and enough acetone-d$_6$ to reach a total volume of 1.0 mL. The reaction was kept at room temperature and monitored at the times given below.

[i]Refer to XI-5 above.

TABLE XIII-6

Yields determined by NMR in isomerization of 9-decen-1-ol using 0.5 mol % catalyst mixture and 0.5 mol % TlPF$_6$ at room temperature in acetone-d6.

| | Measured integrals in arbitrary units relative to internal standard = 10.0 units and (in bold) derived percent yields of products and amount of starting 1-alkene. | | | | | | |
|---|---|---|---|---|---|---|---|
| Time | 0 min | 15 min | 30 min | 1 h | 2 h | 5 h | 7 h |
| ~~~~~OH (5.76-5.84 ppm) | 42.4 | 21.0 | 14.7 | 9.04 | 4.26 | 1.48 | 1.12 |
| ~~~~~OH (4.85-5.02 ppm) | 85.7 | 42.5 | 29.7 | 18.2 | 8.68 | 2.91 | 2.13 |
| units per proton[a] | 42.6 | 21.1 | 14.8 | 9.07 | 4.30 | 1.47 | 1.09 |
| % starting material remaining | 100 | 49.6 | 34.7 | 21.3 | 10.1 | 3.4 | 2.6 |
| ~~~~~OH (1.60 ppm) | — | 44.4 | 59.4 | 67.9 | 79.3 | 83.6 | 84.2 |
| units per proton | — | 22.2 | 29.6 | 33.8 | 39.4 | 41.8 | 42.1 |
| % yield product | 0 | 52.1 | 69.4 | 79.4 | 92.4 | 98.1 | 98.8 |
| ~~~~~OH (0.94 ppm) | — | — | 0.33 | 0.35 | 0.87 | 1.41 | 1.55 |
| units per proton | — | — | 0.11 | .12 | 0.29 | 0.47 | 0.52 |
| % of isomer | 0 | 0 | 0.3 | 0.3 | 0.6 | 1.1 | 1.2 |
| ~~~~~CHO (9.72 ppm) | — | — | — | — | — | — | — |
| units per proton | — | — | — | — | — | — | — |
| % of aldehyde | 0 | 0 | 0 | 0 | 0 | 0 | 0 |

[a]Units calculated by taking the average of the integrations of the two resonances.

XIII-7. Procedure for isomerization of untreated[i] 4-penten-1-ol tert-butyldimethyl silyl ether to E-3 and E-2 penten-1-ol tertbutyldimethyl silyl ethers using 0.5 mol % catalyst and 0.5 mol % TlPF$_6$ at room temperature in acetone-d$_6$.

To a resealable J. Young tube in a glovebox, internal standard (Me$_3$Si)$_4$C (~0.2 mg), TlPF$_6$ (0.9 mg, 0.0026 mmol) and 4-penten-1-ol tertbutyldimethylsilylether (100.2 mg, 0.500 mmol) were combined with a mixture of deoxygenated acetone-d$_6$ (700 µL), and an initial NMR spectrum was acquired. Back in the glovebox, to this mixture was added an aliquot of precatalyst solution B (100 µL, 0.00250 mmol) and enough acetone-d$_6$ to reach a total volume of 1.0 mL. The reaction was kept at room temperature and monitored at the times given below.

[i]Refer to XI-5 above.

TABLE XIII-7

Yields determined by NMR in isomerization of 4-penten-1-ol tert-butyldimethylsilylether using 0.5 mol % catalyst mixture and 0.5 mol % TlPF$_6$ at room temperature in acetone-d$_6$.

| | Measured integrals in arbitrary units relative to internal standard = 10.0 units and (in bold) derived percent yields of products and amount of starting 1-alkene. | | | |
|---|---|---|---|---|
| Time | 0 min | 15 min | 30 min | 1 h |
| 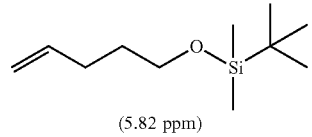 (5.82 ppm) | 82.5 | 2.35 | 2.23 | 2.61 |
| 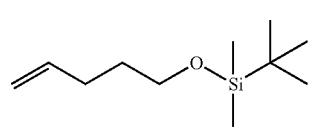 (4.82-5.10 ppm) | 166.7 | 5.39 | 4.52 | 2.99 |
| units per proton[a] | 82.9 | 2.52 | 2.25 | 1.50 |
| % starting material remaining | 100 | 3.0 | 2.7 | 2.5 |
| 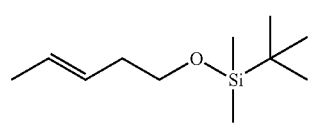 (5.38-5.52 ppm) | — | 155.1 | 163.6 | 158.8 |
| units per proton | — | 77.6 | 81.8 | 79.4 |
| % yield product | 0 | 93.6 | 98.7 | 95.8 |
| 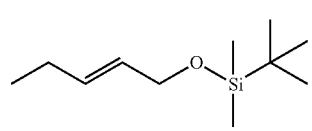 (4.12 ppm) | — | 2.38 | 3.28 | 5.31 |
| units per proton | — | 1.19 | 1.64 | 2.66 |
| % of isomer | 0 | 1.4 | 2.0 | 3.2 |
| 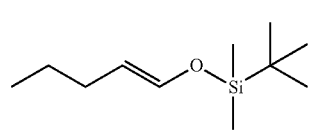 (6.23 ppm) | — | — | — | — |
| units per proton | — | — | — | — |
| % of aldehyde | 0 | 0 | 0 | — |

[a]Units calculated by taking the average of the integrations of the two resonances.

XIII-8. Procedure for isomerization of untreated[i] 9-decen-1-ol tert-butyldimethyl silyl ether to E-8 and E-7 decen-1-ol tert-butyldimethyl silyl ethers using 0.5 mol % catalyst and 0.5 mol % TlPF$_6$ at room temperature in acetone-d$_6$.

To a resealable J. Young tube in a glovebox, internal standard (Me$_3$Si)$_4$C (~0.2 mg), TlPF$_6$ (0.3 mg, 0.000859 mmol) and 1-9-decen-1-ol tert-butyldimethylsilylether (135.3 mg, 0.500 mmol) were combined with a mixture of deoxygenated acetone-d$_6$ (700 μL), and an initial NMR spectrum was acquired. Back in the glovebox, to this mixture was added an aliquot of precatalyst solution B (100 μL, 0.00250 mmol) and enough acetone-d$_6$ to reach a total volume of 1.0 mL. The reaction was kept at room temperature and monitored at the times given below.

[i]Refer to XI-5 above.

TABLE XIII-8

Yields determined by NMR in isomerization of 9-decen-1-ol tert-butyldimethylsilylether using 0.5 mol % catalyst mixture and 0.5 mol % TlPF$_6$ at room temperature in acetone-d$_6$.

| | Measured integrals in arbitrary units relative to internal standard = 10.0 units and (in bold) derived percent yields of products and amount of starting 1-alkene. | | | |
|---|---|---|---|---|
| Time | 0 min | 15 min | 30 min | 1 h |
| 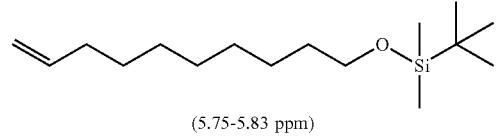 (5.75-5.83 ppm) | 60.7 | 1.84 | 2.38 | 1.60 |
| 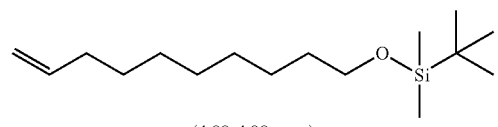 (4.88-4.99 ppm) | 122.3 | 2.80 | 2.71 | 2.46 |
| units per proton$^a$ | 60.9 | 1.62 | 1.86 | 1.42 |
| % starting material remaining | 100 | 2.7 | 3.0 | 2.3 |
| 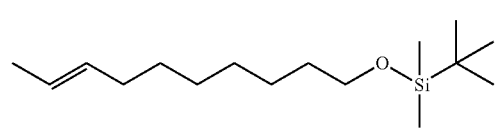 [SMILES: C/C=C/CCCCCCCO[Si](C)(C)C(C)(C)C] (1.61 ppm) | — | 169.8 | 164.3 | 157.1 |
| units per proton | — | 56.6 | 54.8 | 52.4 |
| % yield product | 0 | 92.9 | 90.0 | 86.0 |
| 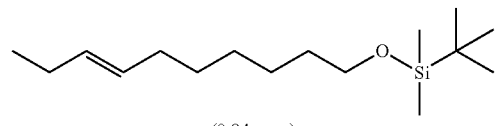 (0.94 ppm) | — | 9.20 | 12.6 | 18.2 |
| units per proton | — | 3.07 | 4.20 | 6.07 |
| % of isomer | 0 | 5.0 | 6.9 | 10.0 |
| 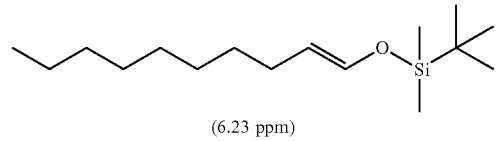 (6.23 ppm) | — | — | — | — |
| units per proton | — | — | — | — |
| % of enol ether | 0 | 0 | 0 | 0 |

$^a$Units calculated by taking the average of the integrations of the two resonances.

XIV: Comparisons with Nitrile Catalyst.

XIV-1. Procedure for isomerization of treated$^i$ 1-hexene to E-2 and E-3 hexenes using 0.5 mol % catalyst and 0.5 mol % TlPF$_6$ at room temperature in acetone-d$_6$.

To a resealable J. Young tube in a glovebox, internal standard (Me$_3$Si)$_4$C (~0.2 mg), TlPF$_6$ (1 mg, 0.0029 mmol) and alumina-filtered 1-hexene (42.1 mg, 0.500 mmol) were combined with a mixture of deoxygenated acetone-d$_6$ (700 μL), and an initial NMR spectrum was acquired. Back in the glovebox, to this mixture was added an aliquot of precatalyst solution B (100 μL, 0.00250 mmol) and enough acetone-d$_6$ to reach a total volume of 1.0 mL. The reaction was kept at room temperature and monitored at the times given below.

$^i$Refer to XI-5 above.

TABLE XIV-1

Yields determined by NMR in isomerization of 1-hexene using 0.5 mol % catalyst mixture and 0.5 mol % TlPF$_6$ at room temperature in acetone-d$_6$. Measured integrals in arbitrary units relative to internal standard = 10.0 units and (in bold) derived percent yields of products and amount of starting 1-alkene.

| Time | 0 min | 15 min | 30 min | 1 h |
|---|---|---|---|---|
| 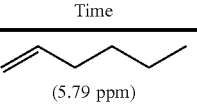 (5.79 ppm) | 66.0 | 2.14 | 1.43 | 1.36 |
| 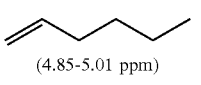 (4.85-5.01 ppm) | 135.4 | 4.17 | 2.46 | 2.60 |

TABLE XIV-1-continued

Yields determined by NMR in isomerization of 1-hexene using 0.5 mol % catalyst mixture and 0.5 mol % TlPF$_6$ at room temperature in acetone-d$_6$. Measured integrals in arbitrary units relative to internal standard = 10.0 units and (in bold) derived percent yields of products and amount of starting 1-alkene.

| Time | 0 min | 15 min | 30 min | 1 h |
|---|---|---|---|---|
| units per proton[a] | 66.9 | 2.11 | 1.33 | 1.33 |
| % starting material remaining | 100 | 3.2 | 2.0 | 2.0 |
| 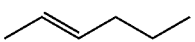 (5.35-5.46 ppm)[b] | — | 131.8 | 131.8 | 131.8 |
| 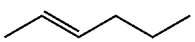 (1.60 ppm) | — | 197.7 | 194.5 | 189.2 |
| units per proton[c] | — | 64.7 | 64.1 | 62.1 |
| % of E-2 | 0 | 96.7 | 95.9 | 92.7 |
| 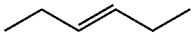 (0.94 ppm) | — | 3.61 | 7.27 | 14.4 |
| units per proton | — | 1.20 | 2.42 | 4.82 |
| % of E-3 | 0 | 1.8 | 3.6 | 7.2 |

[a]Units calculated by taking the average of the integrations of the two resonances.
[b]Signal is a mixture of E-2 and E-3 hexene isomers.
[c]Vinylic C—H proton units for E-2 hexene determined by subtracting proton units of E-3 hexene from total proton units of E-2/E-3 signal XIV-2. Procedure for isomerization of treated[i] 1-hexene to E-2 and E-3 hexenes using 0.5 mol % 1+3 at room temperature in acetone-d$_6$.

To a resealable J. Young tube in a glovebox, internal standard (Me$_3$Si)$_4$C (~0.2 mg) and alumina-filtered 1-hexene (42.1 mg, 0.500 mmol) were combined with a mixture of deoxygenated acetone-d$_6$ (700 μL), and an initial NMR spectrum was acquired. Back in the glovebox, to this mixture was added an aliquot of precatalyst solution B (100 μL, 0.00250 mmol) and enough acetone-d$_6$ to reach a total volume of 1.0 mL. The reaction was kept at room temperature and monitored at the times given below.

[i]Refer to XI-5 above.

TABLE XIV-2

Yields determined by NMR in isomerization of 1-hexene using 0.5 mol % 1 + 3 at room temperature in acetone-d$_6$. Measured integrals in arbitrary units relative to internal standard = 10.0 units and (in bold) derived percent yields of products and amount of starting 1-alkene.

| Time | 0 min | 15 min | 1 h | 5 h | 21 h* | 24 h* | 48 h | 72 h | 96 h |
|---|---|---|---|---|---|---|---|---|---|
| (5.79 ppm) | 42.2 | 40.5 | 38.8 | 32.7 | 17.1 | 16.5 | 9.64 | 5.94 | 4.28 |
| (4.85-5.01 ppm) | 86.9 | 82.9 | 79.4 | 67.1 | 35.6 | 33.5 | 19.7 | 11.9 | 8.48 |
| units per proton[a] | 42.8 | 41.0 | 39.2 | 33.1 | 17.5 | 16.6 | 9.75 | 5.95 | 4.26 |
| % starting material remaining | 100 | 95.7 | 91.7 | 77.4 | 40.8 | 38.8 | 22.8 | 13.9 | 10.0 |
| (5.35-5.46 ppm)[b] | — | 2.78 | 5.89 | 18.1 | 39.6 | 44.1 | 64.7 | 71.9 | 75.8 |
| (1.60 ppm) | — | 4.15 | 8.99 | 27.6 | 61.7 | 66.9 | 97.5 | 107.6 | 112.4 |
| units per proton[c] | — | 1.39 | 2.97 | 9.05 | 20.1 | 22.0 | 32.2 | 35.6 | 37.4 |
| % of E-2 | 0 | 3.2 | 6.9 | 21.1 | 46.9 | 51.4 | 75.2 | 83.2 | 87.3 |
| 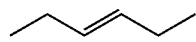 (0.94 ppm) | — | — | — | — | 0.61 | 0.82 | 1.40 | 1.71 | 1.92 |
| units per proton | — | — | — | — | 0.20 | 0.27 | 0.47 | 0.57 | 0.64 |
| % of E-3 | 0 | 0 | 0 | 0 | 0.5 | 0.6 | 1.1 | 1.3 | 1.5 |

[a]Units calculated by taking the average of the integrations of the two resonances.
[b]Signal is a mixture of E-2 and E-3 hexene isomers.
[c]Vinylic C—H proton units for E-2 hexene determined by subtracting proton units of E-3 hexene from total proton units of E-2/E-3 signal.

XIV-3. Procedure for isomerization of treated[i] 1-hexene to E-2 and E-3 hexenes using 0.5 mol % cl969 at room temperature in acetone-d$_6$.

To a resealable J. Young tube in a glovebox, internal standard (Me$_3$Si)$_4$C (~0.2 mg) and alumina-filtered 1-hexene (42.1 mg, 0.500 mmol) were combined with a mixture of deoxygenated acetone-d$_6$ (700 μL), and an initial NMR spectrum was acquired. Back in the glovebox, to this mixture was added an aliquot of precatalyst solution B (100 μL, 0.00250 mmol) and enough acetone-d$_6$ to reach a total volume of 1.0 mL. The reaction was kept at room temperature and monitored at the times given below.

[i]Refer to XI-5 above.

TABLE XIV-3

Yields determined by NMR in isomerization of 1-hexene using 0.5 mol % 1 + 3 at room temperature in acetone-$d_6$.
Measured integrals in arbitrary units relative to internal standard = 10.0 units and (in bold) derived percent yields of products and amount of starting 1-alkene.

| Time | 0 min | 72 h | 96 h | 120 h | 144 h | 191 h | 216 h | 240 h |
|---|---|---|---|---|---|---|---|---|
| (5.79 ppm) | 56.6 | 16.8 | 11.3 | 7.82 | 5.40 | 3.06 | 2.36 | 1.96 |
| (4.85-5.01 ppm) | 117.1 | 33.9 | 22.8 | 15.7 | 10.9 | 6.12 | 4.85 | 3.96 |
| units per proton[a] | 57.6 | 16.9 | 11.4 | 7.84 | 5.43 | 3.06 | 2.39 | 1.97 |
| % starting material remaining | 100 | 29.4 | 19.7 | 13.6 | 9.4 | 5.3 | 4.2 | 3.4 |
| (5.35-5.46 ppm)[b] | — | 81.8 | 93.2 | 101.1 | 104.5 | 111.7 | 111.0 | 112.9 |
| (1.60 ppm) | — | 121.5 | 138.6 | 150.7 | 155.8 | 165.5 | 164.4 | 167.2 |
| units per proton[c] | — | 40.5 | 45.7 | 49.6 | 51.5 | 54.8 | 54.4 | 55.3 |
| % of E-2 | 0 | 70.3 | 79.3 | 86.2 | 89.5 | 95.1 | 94.5 | 96.0 |
| (0.94 ppm) | — | 2.42 | 2.67 | 2.77 | 3.35 | 4.07 | 4.44 | 4.92 |
| units per proton | — | 0.81 | 0.89 | 0.92 | 1.12 | 1.36 | 1.48 | 1.64 |
| % of E-3 | 0 | 1.4 | 1.5 | 1.6 | 1.9 | 2.4 | 2.6 | 2.8 |

[a] Units calculated by taking the average of the integrations of the two resonances.
[b] Signal is a mixture of E-2 and E-3 hexene isomers.
[c] Vinylic C—H proton units for E-2 hexene determined by subtracting proton units of E-3 hexene from total proton units of E-2/E-3 signal.

XIV-4. Procedure for isomerization of treated[i] 1-hexene to E-2 and E-3 hexenes using 0.1 mol % catalyst and 0.15 mol % TlPF$_6$ at 40° C. in acetone-$d_6$.

To a resealable J. Young tube in a glovebox, internal standard (Me$_3$Si)$_4$C (~0.2 mg), TlPF$_6$ (1 mg, 0.0029 mmol) and alumina-filtered 1-hexene (42.1 mg, 0.500 mmol) were combined with a mixture of deoxygenated acetone-$d_6$ (700 μL), and an initial NMR spectrum was acquired. Back in the glovebox, to this mixture was added an aliquot of catalyst solution B (100 μL, 0.00250 mmol) and enough acetone-$d_6$ to reach a total volume of 1.0 mL. The reaction was kept at 40° C. in the NMR probe for the first 2 h and monitored at the times given below. After 2 h, the tube was kept in a 40° C. bath except for NMR acquisitions.

[i] Refer to XI-5 above.

TABLE XIV-4

Yields determined by NMR in isomerization of 1-hexene using 0.1 mol % catalyst mixture and 0.15 mol % TlPF$_6$ at 40° C. in acetone-$d_6$.
Measured integrals in arbitrary units relative to internal standard = 10.0 units and (in bold) derived percent yields of products and amount of starting 1-alkene.

| Time | 0 min | 15 min | 30 min | 45 min | 1 h | 1.5 h | 2 h | 4 h | 6 h | 24 h |
|---|---|---|---|---|---|---|---|---|---|---|
| (5.79 ppm) | 61.2 | 30.7 | 14.2 | 7.26 | 4.20 | 2.09 | 1.66 | 1.35 | 1.41 | 1.35 |
| (4.85-5.01 ppm) | 125.4 | 62.2 | 28.6 | 14.7 | 8.54 | 4.12 | 3.32 | 2.77 | 2.85 | 2.77 |
| units per proton[a] | 62.0 | 30.9 | 14.3 | 7.31 | 4.23 | 2.08 | 1.66 | 1.36 | 1.42 | 1.37 |
| % starting material remaining | 100 | 49.8 | 23.0 | 11.8 | 6.8 | 3.3 | 2.7 | 2.2 | 2.3 | 2.2 |
| (5.35-5.46 ppm)[b] | — | 65.3 | 95.6 | 109.8 | 115.4 | 121.9 | 122.3 | 120.6 | 122.1 | 118.5 |
| (1.60 ppm) | — | 98.3 | 143.5 | 164.1 | 171.5 | 181.2 | 180.7 | 177.7 | 178.4 | 168.8 |
| units per proton[c] | — | 32.7 | 47.5 | 54. | 57.0 | 59.9 | 59.3 | 58.3 | 58.3 | 54.7 |
| % of E-2 | 0 | 52.7 | 76.6 | 87.8 | 91.8 | 96.6 | 95.7 | 94.0 | 94.0 | 88.3 |
| (0.94 ppm) | — | — | 1.77 | 2.34 | 2.92 | 4.78 | 5.50 | 8.78 | 11.6 | 18.2 |

TABLE XIV-4-continued

Yields determined by NMR in isomerization of 1-hexene using 0.1 mol % catalyst mixture and 0.15 mol % TlPF$_6$ at 40° C. in acetone-d$_6$.
Measured integrals in arbitrary units relative to internal standard = 10.0 units and (in bold) derived percent yields of products and amount of starting 1-alkene.

| Time | 0 min | 15 min | 30 min | 45 min | 1 h | 1.5 h | 2 h | 4 h | 6 h | 24 h |
|---|---|---|---|---|---|---|---|---|---|---|
| units per proton | — | — | 0.59 | 0.78 | 0.97 | 1.59 | 1.83 | 2.93 | 3.87 | 6.07 |
| % of E-3 | 0 | 0 | 0.9 | 1.3 | 1.6 | 2.6 | 3.0 | 4.7 | 6.2 | 9.8 |

[a]Units calculated by taking the average of the integrations of the two resonances.
[b]Signal is a mixture of E-2 and E-3 hexene isomers.
[c]Vinylic C—H proton units for E-2 hexene determined by subtracting proton units of E-3 hexene from total proton units of E-2/E-3 signal XIV-5. Procedure for isomerization of treated[i] 1-hexene to E-2 and E-3 hexenes using 0.1 mol % 1+3 at room temperature in acetone-d$_6$.

To a resealable J. Young tube in a glovebox, internal standard (Me$_3$Si)$_4$C (~0.2 mg) and alumina-filtered 1-hexene (42.1 mg, 0.500 mmol) were combined with a mixture of deoxygenated acetone-d$_6$ (700 μL), and an initial NMR spectrum was acquired. Back in the glovebox, to this mixture was added an aliquot of precatalyst solution B (20 μL, 0.00250 mmol) and enough acetone-d$_6$ to reach a total volume of 1.0 mL. The reaction was kept at room temperature and monitored at the times given below.
[i]Refer to XI-5 above.

TABLE XIV-5

Yields determined by NMR in isomerization of 1-hexene using 0.1 mol % 1 + 3 at 40° C. in acetone-d$_6$.
Measured integrals in arbitrary units relative to internal standard = 10.0 units and (in bold) derived percent yields of products and amount of starting 1-alkene.

| Time | 0 min | 5 h | 24 h | 48 h | 72 h | 96 h |
|---|---|---|---|---|---|---|
| (5.79 ppm) | 91.4 | 83.3 | 83.0 | 81.2 | 80.0 | |
| (4.85-5.01 ppm) | 187.8 | 170.2 | 169.9 | 165.7 | 166.8 | |
| units per proton[a] | 92.7 | 84.2 | 85.0 | 82.0 | 81.7 | |
| % starting material remaining | 100 | 90.8 | 91.6 | 88.5 | 88.1 | |
| (5.35-5.46 ppm)[b] | — | 12.6 | 14.6 | 16.6 | 19.0 | |
| (1.60 ppm) | — | 18.6 | 21.0 | 23.8 | 26.7 | |
| units per proton[c] | — | 6.25 | 7.12 | 8.10 | 9.20 | |
| % of E-2 | 0 | 6.8 | 7.7 | 8.8 | 9.9 | |

TABLE XIV-5-continued

Yields determined by NMR in isomerization of 1-hexene using 0.1 mol % 1 + 3 at 40° C. in acetone-d$_6$.
Measured integrals in arbitrary units relative to internal standard = 10.0 units and (in bold) derived percent yields of products and amount of starting 1-alkene.

| Time | 0 min | 5 h | 24 h | 48 h | 72 h | 96 h |
|---|---|---|---|---|---|---|
| (0.94 ppm) | — | — | — | — | — | |
| units per proton | — | — | — | — | — | |
| % of E-3 | 0 | 0 | 0 | 0 | 0 | |

[a]Units calculated by taking the average of the integrations of the two resonances.
[b]Signal is a mixture of E-2 and E-3 hexene isomers.
[c]Vinylic C—H proton units for E-2 hexene determined by subtracting proton units of E-3 hexene from total proton units of E-2/E-3 signal.

XIV-6. Procedure for isomerization of treated[i] 1-hexene to E-2 and E-3 hexenes using 0.25 mol % catalyst and 0.25 mol % TlPF$_6$ at room temperature (24° C.) in acetone-d$_6$.

To a resealable J. Young tube in a glovebox, internal standard (Me$_3$Si)$_4$C (~0.2 mg), TlPF$_6$ (0.5 mg, 0.0014 mmol) and alumina-filtered 1-hexene (42.1 mg, 0.500 mmol) were combined with a mixture of deoxygenated acetone-d$_6$ (700 μL), and an initial NMR spectrum was acquired. Back in the glovebox, to this mixture was added an aliquot of catalyst solution B (50 μL, 0.00125 mmol) and enough acetone-d$_6$ to reach a total volume of 1.0 mL. The reaction was kept at room temperature for about 2 min and then was inserted in the NMR probe set at 24° C. and monitored at the times given below.
[i]Refer to XI-5 above.

TABLE XIV-6

Yields determined by NMR in isomerization of 1-hexene using 0.25 mol % catalyst mixture and 0.25 mol % TlPF$_6$ at 24° C. in acetone-d$_6$.
Measured integrals in arbitrary units relative to internal standard = 10.0 units and (in bold) derived percent yields of products and amount of starting 1-alkene.

| Time | 0 min | 3 min | 6 min | 8 min | 11 min | 14 min | 16 min | 19 min | 21 min | 24 min | 27 min | 29 min | 32 min |
|---|---|---|---|---|---|---|---|---|---|---|---|---|---|
| (5.79 ppm) | 73.2 | 43.5 | 34.8 | 25.4 | 18.8 | 13.2 | 9.11 | 6.16 | 4.71 | 3.51 | 2.73 | 2.38 | 1.92 |
| (4.85-5.01 ppm) | 149.3 | 97.7 | 71.3 | 52.1 | 38.1 | 26.6 | 18.5 | 12.7 | 9.69 | 7.09 | 5.41 | 4.45 | 3.97 |
| units per proton[a] | 73.9 | 46.0 | 35.2 | 25.7 | 18.9 | 13.3 | 9.18 | 6.26 | 4.78 | 3.53 | 2.72 | 2.30 | 1.95 |
| % starting material remaining | 100 | 62.2 | 47.6 | 34.8 | 25.6 | 17.9 | 12.4 | 8.5 | 6.5 | 4.8 | 3.7 | 3.1 | 2.6 |

TABLE XIV-6-continued

Yields determined by NMR in isomerization of 1-hexene using 0.25 mol % catalyst mixture and 0.25 mol % TlPF$_6$ at 24° C. in acetone-d$_6$.
Measured integrals in arbitrary units relative to internal standard = 10.0 units and (in bold) derived percent yields of products and amount of starting 1-alkene.

| Time | 0 min | 3 min | 6 min | 8 min | 11 min | 14 min | 16 min | 19 min | 21 min | 24 min | 27 min | 29 min | 32 min |
|---|---|---|---|---|---|---|---|---|---|---|---|---|---|
| 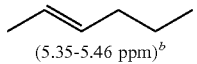 (5.35-5.46 ppm)[b] | — | 44.6 | 75.4 | 94.7 | 109.2 | 119.8 | 127.6 | 131.5 | 137.4 | 138.4 | 139.5 | 140.8 | 142.6 |
| 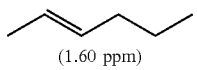 (1.60 ppm) | — | 72.0 | 113.9 | 143.3 | 163.7 | 180.6 | 191.8 | 199.8 | 207.5 | 208.5 | 210.5 | 212.3 | 215.0 |
| units per proton[c] | — | 23.2 | 37.8 | 47.6 | 54.6 | 59.7 | 63.4 | 64.3 | 68.4 | 68.6 | 69.3 | 69.9 | 70.7 |
| % of E-2 | 0 | 31.3 | 51.2 | 64.4 | 73.9 | 80.7 | 85.8 | 87.1 | 92.5 | 92.8 | 93.8 | 94.5 | 95.6 |
| 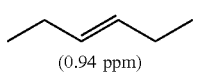 (0.94 ppm) | — | — | — | — | — | 2.31 | 2.65 | 2.96 | 3.40 | 3.72 | 4.01 | 4.42 | 4.95 |
| units per proton | — | — | — | — | — | 0.77 | 0.88 | 0.99 | 1.13 | 1.24 | 1.34 | 1.47 | 1.65 |
| % of E-3 | 0 | 0 | 0 | 0 | 0 | 1.0 | 1.2 | 1.3 | 1.5 | 1.7 | 1.8 | 2.0 | 2.2 |

[a]Units calculated by taking the average of the integrations of the two resonances.
[b]Signal is a mixture of E-2 and E-3 hexene isomers.
[c]Vinylic C—H proton units for E-2 hexene determined by subtracting proton units of E-3 hexene from total proton units of E-2/E-3 signal.

Figure 25:
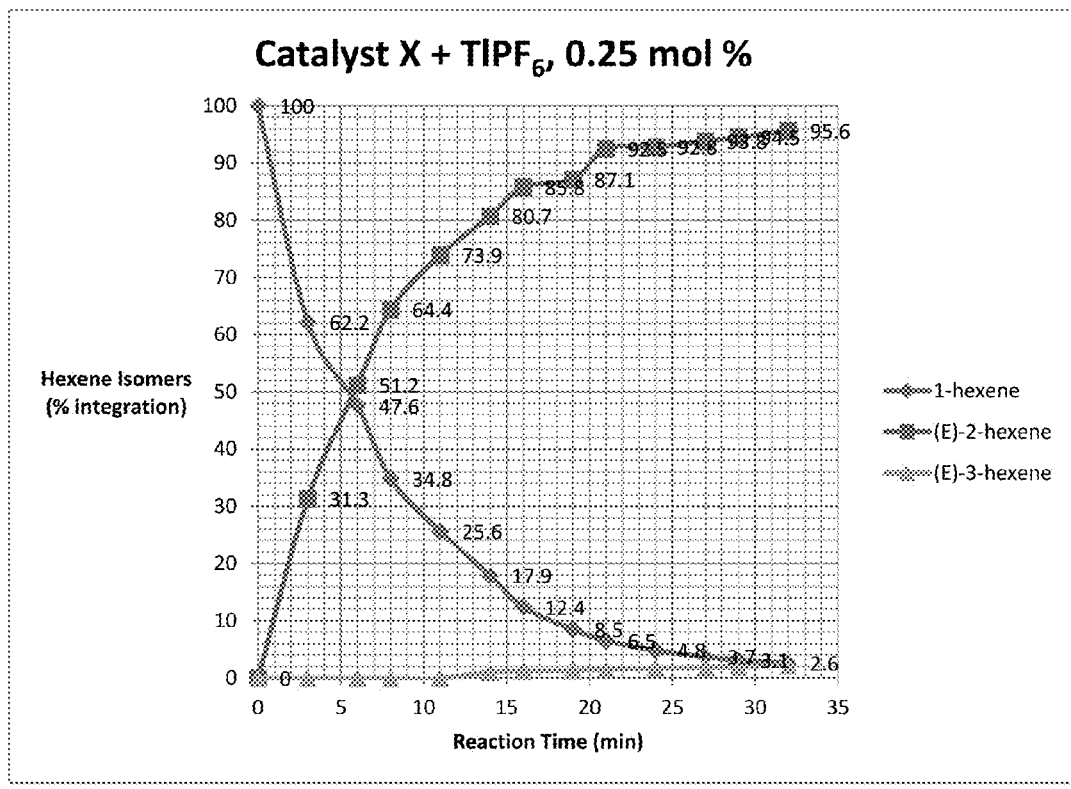
FIG. 25. Plot of percent yield of products and percent starting 1-hexene remaining as a function of reaction time, using nitrile-free catalyst Y. Sample was kept at room temperature (~24° C.) both while mixing and in the NMR probe during acquisition of NMR spectra. The lines connecting data points are not created using an equation but are intended as a visual aid.

See FIG. 25.

XIV-7. Procedure for isomerization of treated[i] 1-hexene to E-2 and E-3 hexenes using 0.25 mol % 1+3 at room temperature in acetone-d$_6$.

To a resealable J. Young tube in a glovebox, internal standard (Me$_3$Si)$_4$C (~0.2 mg) and alumina-filtered 1-hexene (42.1 mg, 0.500 mmol) were combined with a mixture of deoxygenated acetone-d$_6$ (700 μL), and an initial NMR spectrum was acquired. Back in the glovebox, to this mixture was added an aliquot of precatalyst solution B (50 μL, 0.00125 mmol) and enough acetone-d$_6$ to reach a total volume of 1.0 mL. The reaction was kept at room temperature and monitored at the times given below.

[i]Refer to XI-5 above.

TABLE XIV-7

Yields determined by NMR in isomerization of 1-hexene using 0.25 mol % 1 + 3 at room temperature in acetone-d$_6$.
Measured integrals in arbitrary units relative to internal standard = 10.0 units and (in bold) derived percent yields of products and amount of starting 1-alkene.

| Time | 0 min | 30 min | 24 h | 48 h | 72 h |
|---|---|---|---|---|---|
| 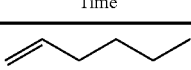 (5.79 ppm) | 43.3 | 42.0 | 27.2 | 19.7 | 15.5 |
| 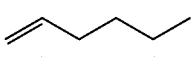 (4.85-5.01 ppm) | 89.1 | 86.4 | 55.3 | 39.8 | 31.2 |
| units per proton[a] | 43.9 | 42.6 | 27.4 | 19.8 | 15.6 |
| % starting material remaining | 100 | 97.0 | 62.5 | 45.1 | 35.5 |
| 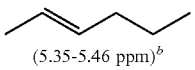 (5.35-5.46 ppm)[b] | — | 1.81 | 33.1 | 47.1 | 56.5 |
| 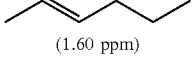 (1.60 ppm) | — | 2.74 | 49.4 | 69.9 | 83.6 |
| units per proton[c] | — | 0.91 | 16.5 | 23.4 | 27.8 |
| % of E-2 | 0 | 2.1 | 37.6 | 53.3 | 63.3 |
| 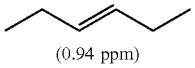 (0.94 ppm) | — | — | — | — | 1.46 |

TABLE XIV-7-continued

Yields determined by NMR in isomerization of 1-hexene using 0.25 mol % 1 + 3 at room temperature in acetone-$d_6$.
Measured integrals in arbitrary units relative to internal standard = 10.0 units and (in bold) derived percent yields of products and amount of starting 1-alkene.

| Time | 0 min | 30 min | 24 h | 48 h | 72 h |
|---|---|---|---|---|---|
| units per proton | — | — | — | — | 0.49 |
| % of E-3 | 0 | 0 | 0 | 0 | 1.1 |

[a] Units calculated by taking the average of the integrations of the two resonances.
[b] Signal is a mixture of E-2 and E-3 hexene isomers.
[c] Vinylic C—H proton units for E-2 hexene determined by subtracting proton units of E-3 hexene from total proton units of E-2/E-3 signal.

Figure 26:
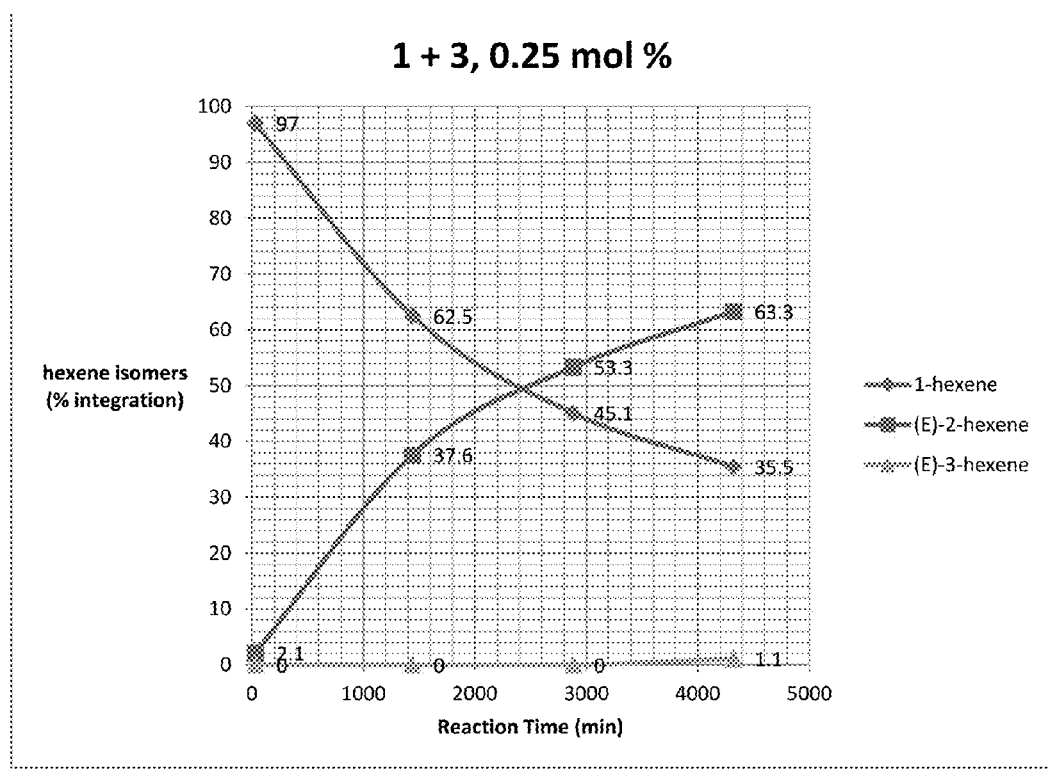
FIG. 26. Plot of percent yield of products and percent starting 1-hexene remaining as a function of reaction time, using nitrile-bearing catalyst reported in *J. Am. Chem. Soc.* (2014), 136, 1226. Sample was kept at room temperature (~24° C.) both while mixing and between NMR acquisitions, whereas in the NMR probe during a few minutes of NMR spectra acquisition, the temperature was 30° C. The lines connecting data points are not created using an equation but are intended as a visual aid.

See FIG. 26.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An alkene isomerization catalyst of Formula I, Formula II, Formula III, Formula IV, or a combination thereof:

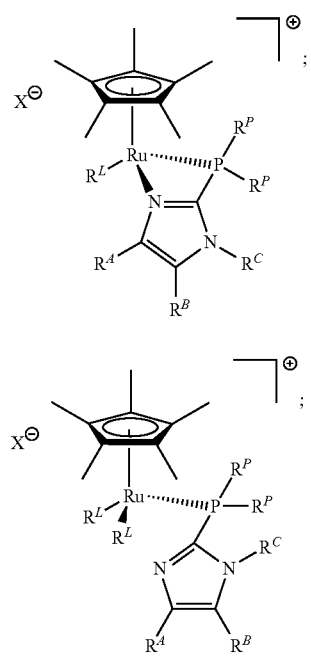

wherein
each $R^P$ is independently a branched $(C_3-C_{10})$-alkyl, $(C_3-C_{10})$-cycloalkyl, $(C_3-C_{15})$-alkenyl, $(C_2-C_{12})$-alkynyl, heterocyclyl, or an optionally substituted aryl or heteroaryl;
each $R^L$ is independently a neutral or anionic ligand, or is absent, provided that at least one $R^L$ is not absent when the catalyst is a catalyst of Formula II or Formula IV;
each $R^A$, $R^B$ and $R^C$ is independently hydrogen, a branched or linear $(C_1-C_{20})$-alkyl, $(C_3-C_{10})$-cycloalkyl, $(C_3-C_{15})$-alkenyl, $(C_2-C_{12})$-alkynyl, heterocyclyl, or an optionally substituted aryl or heteroaryl; and
$X^-$ is a counterion.

2. The catalyst of claim 1 wherein $R^P$ is iso-propyl, iso-butyl, tent-butyl or 1-adamantyl.

3. The catalyst of claim 1 wherein $R^L$ is alkyl nitrile, cycloalkyl nitrile, aryl nitrile, heteroaryl nitrile, heterocycloalkyl nitrile, alkylcarbonyl, CO, alkylamine, alkenylamine, arylamine, amide, alkanol, water, $(C_3-C_{15})$-alkenol, cycloalkanol, aryl alcohol, ketone, ether, aldehyde, alkene, halo, carboxylate, sulfonyl, sulfonate, phosphonyl, phosphinyl, or $N_2$.

4. The catalyst of claim 3 wherein $R^L$ is carbonyl, CO, alkylamine, alkenylamine, arylamine, amide, alkanol, water, $(C_3-C_{15})$-alkenol, cycloalkanol, aryl alcohol, ketone, ether, aldehyde, alkene, halo, carboxylate, sulfonyl, sulfonate, phosphonyl, phosphinyl, or N₂.

5. The catalyst of claim 3 wherein $R^L$ is acetonitrile, acetone or THF.

6. The catalyst of claim 1 wherein X⁻ is an inorganic halide, CF₃SO₃⁻, BF₄⁻, BPh₄⁻, B(C₆F₅)₄⁻, or B[C₆H₃-3,5-(CF₃)₂]₄⁻.

7. The catalyst of claim 6 wherein X⁻ is PF₆⁻.

8. The catalyst of claim 1 wherein the catalyst is a mixture of Formula I and Formula II or a mixture of Formula III and Formula IV.

9. The catalyst of claim 1 wherein the catalyst is formula 1:

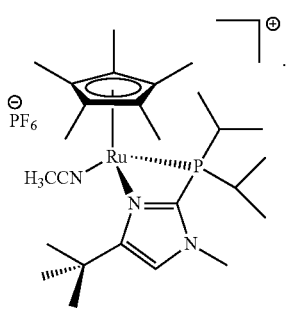

(1)

10. The catalyst of claim 1 wherein the catalyst is formula 3:

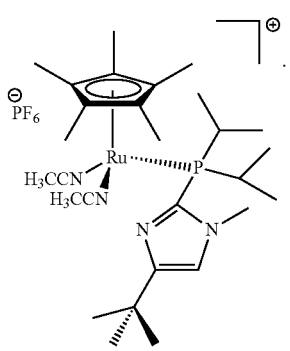

(3)

11. A catalyst comprising a mixture of formula 1 and formula 3:

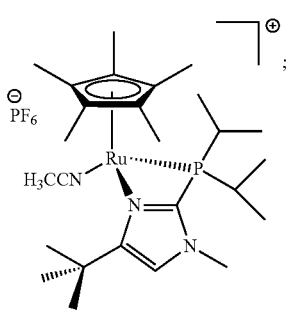

(1)

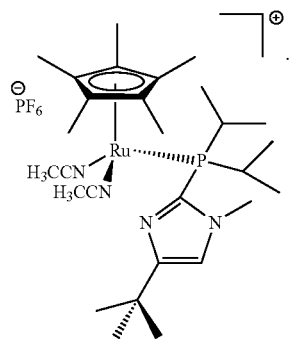

(3)

12. The catalyst of claim 11 wherein the ratio of formula 1 to formula 3 is from about 1:2 to about 1:5.

13. The catalyst of claim 1 wherein the catalyst is formula 8:

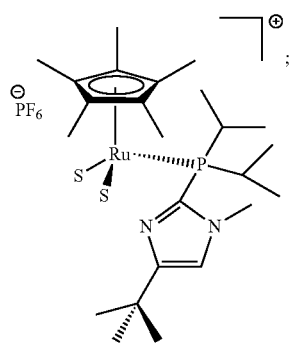

(8)

wherein each S is independently solvent, N₂, or absent, provided that at least one S is not absent.

14. The catalyst of claim 1 wherein the catalyst is formula 9:

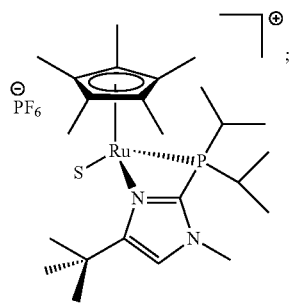

(9)

wherein S is solvent, N₂, or absent.

15. The catalyst of claim 1 wherein the catalyst is a mixture of formula 8 and formula 9:

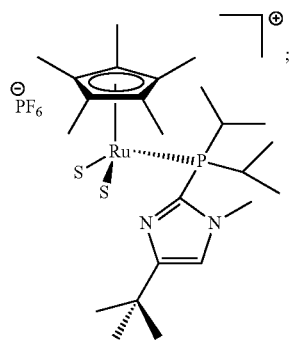

(8)

-continued

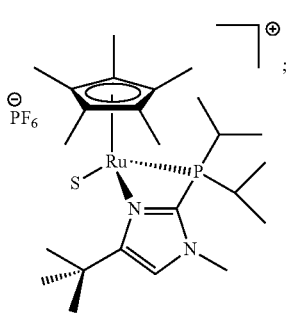

(9)

wherein each S is independently solvent, N₂, or absent, provided that at least one S of formula 8 is not absent.

16. A method of isomerizing a 1-alkene to an E-2-alkene comprising contacting a 1-alkene in a reaction mixture with an effective amount of a catalyst of Formula I, Formula II, Formula III, Formula IV, or a combination thereof:

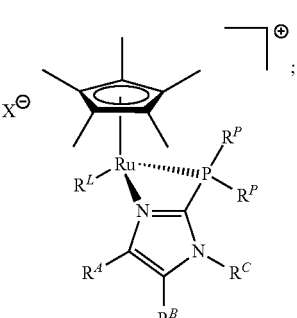

(I)

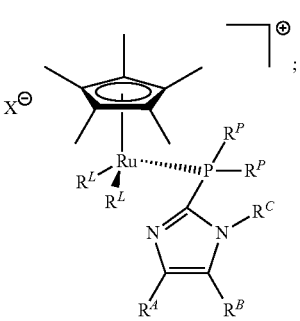

(II)

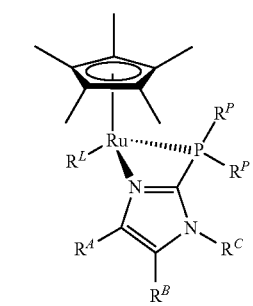

(III)

-continued

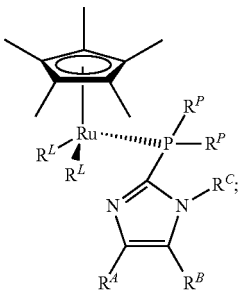

(IV)

wherein each $R^P$ is independently a branched $(C_3-C_{10})$-alkyl, $(C_3-C_{10})$-cycloalkyl, $(C_3-C_{15})$-alkenyl, $(C_2-C_{12})$-alkynyl, heterocyclyl, or an optionally substituted aryl or heteroaryl;

each $R^L$ is independently a neutral or anionic ligand, or is absent, provided that at least one $R^L$ is not absent when the catalyst is a catalyst of Formula II or Formula IV;

each $R^A$, $R^B$ and $R^C$ is independently hydrogen, a branched or linear $(C_1-C_{20})$-alkyl, $(C_3-C_{10})$-cycloalkyl, $(C_3-C_{15})$-alkenyl, $(C_2-C_{12})$-alkynyl, heterocyclyl, or an optionally substituted aryl or heteroaryl; and $X^-$ is a counterion;

wherein the reaction mixture optionally includes a suitable solvent, and the method is carried out for a period of time sufficient to convert at least about 70% of the 1-alkene to an E-2-alkene.

17. The method of claim 16 wherein the reaction mixture comprises about 0.01 mol % to about 20 mol % of the catalyst.

18. The method of claim 16 wherein the temperature of the reaction mixture is about 20° C. to about 100° C.

19. The method of claim 18 wherein the catalyst is a mixture of Formula I and Formula II or a mixture of Formula III and Formula IV.

20. The method of claim 16 wherein $R^L$ is alkylcarbonyl, CO, alkylamine, alkenylamine, arylamine, amide, alkanol, water, $(C_3-C_{15})$-alkenol, cycloalkanol, aryl alcohol, ketone, ether, aldehyde, alkene, halo, carboxylate, sulfonyl, sulfonate, phosphonyl, phosphinyl, or N₂.

21. The catalyst of claim 1 wherein $X^-$ an alkoxide, a carboxylate, a sulfonate, a borate, a phosphate, or an inorganic halide.

22. The method of claim 16 wherein $X^-$ an alkoxide, a carboxylate, a sulfonate, a borate, a phosphate, or an inorganic halide.

* * * * *